US005952208A

United States Patent [19]
Darzins et al.

[11] Patent Number: 5,952,208
[45] Date of Patent: Sep. 14, 1999

[54] DSZ GENE EXPRESSION IN PSEUDOMONAS HOSTS

[75] Inventors: Aldis Darzins; Lei Xi; John D. Childs; Daniel J. Monticello; Charles H. Squires, all of The Woodlands, Tex.

[73] Assignee: Energy BioSystems Corporation, The Woodlands, Tex.

[21] Appl. No.: 08/851,088

[22] Filed: May 5, 1997

Related U.S. Application Data

[63] Continuation-in-part of application No. 08/835,185, Apr. 7, 1997, abandoned.
[51] Int. Cl.$^6$ .............................. C12P 7/22; C12S 1/12; C12N 15/78
[52] U.S. Cl. .................. 435/156; 435/252.34; 435/282
[58] Field of Search .............................. 935/252, 34, 282, 935/156

[56] References Cited

U.S. PATENT DOCUMENTS

| | | | |
|---|---|---|---|
| 4,562,156 | 12/1985 | Isbister et al. | 435/253 |
| 5,002,888 | 3/1991 | Kilbane, II | 435/262 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,870 | 10/1994 | Monticello et al. | 435/282 |
| 5,607,857 | 3/1997 | Grossman et al. | 435/282 |
| 5,733,773 | 3/1998 | Squires et al. | 435/252.3 |

FOREIGN PATENT DOCUMENTS

WO 96/17940  6/1996  WIPO.

OTHER PUBLICATIONS

Kilbane, J.J. (1989) Tibtech 7, 97–101.
Constanti, M., et al., "Desulphurization of dibenzothiophene by bacteria," *World Journal of Microbiology & Biotechnology* 10:510–516 (1994).
Klubeck, B, et al., "Characterization of soil bacteria that desulphurize organic sulphur compounds," *Microbios* 88:223–236 (1996).
Labes, M., et al., "A new family of RSF1010–derived expression and lac–fusion broad–host–range vectors for Gram–negative bacteria," *Gene* 89:37–46 (1990).
Gallardo, M.E., et al., "Designing Recombinant Pseudomonas Strains to Enhance Biodesulfurization," *Journal of Bacteriology* 179(22):7156–7160 (1997).
Darzins, A., "Expression of the Desulfurization (dsz) Genes from *Rhodococcus erythropolis* IGTS8 in Heterologous Bacterial Hosts," Abstracts of the 97th ASM Meeting, Miami Beach, Florida, May 4–8, 1997, Abstract 0–105.
Gundlach, E.R. et al., "The Fate of Amoco Cadiz Oil" *Science*, 221: 122–129 (1983).
Monticello, D.J. and Finnerty, W.R., "Microbial Desulfurization of Fossil Fuels," *Ann. Rev. Microbiol.* 39: 371–389 (1985).

Kilbane II, J.J., "Sulfer–Specific Microbial Metabolism of Organic Compounds," *Resour. Cons. Recycl.* 3: 69–79 (1990).
Hartdegan, F.J. et al., "Microbial Desulfurization of Petroleum: Developments in genetic engineering have led to the possibility of a bioprocess route to clean up sulfer in oil," *Chem. Eng. Progress*: 63–67 (May 1984).
Figurski, D.H. and Helinski, D.R., "Replication of an origin–containing derivative of plasmid RK2dependent on a plasmid function provided in trans," *Proc. Nat. Acad. Sci. USA*, 76(4): 1648–1652 (Apr. 1979).
Vogelstein, B. and Gillespie, D., "Preparative and analytical purification of DNA from agarose," *Proc., Natl. Acad. Sci. USA*, 76(2): 615–619 (Feb. 1979).
Monticello, D.J. et al., "IGT's Third International Symposium on Gas, Oil, Coal and Environmental Biotechnology," Practical Considerations in Biodesulfurization on Petroleum, New Orleans, LA (Dec. 3–5, 1990).
Omori, T. et al., "Desulfurization of Dibenzothiophene by Corynebacterium sp. Strain SY1," *Appl. Env. Microbiol.*, 58(3) : 911–915 (Mar. 1992).
Izumi, Y. et al., Selective Desulfurization of Dibenzothiophene by *Rhodococcus erythropolis* D–1, *Appl. Env. Microbiol.*, 60(1): 223–226 (1994).
Lee, M.K. et al., "Sulfer–Specific Microbial Desulfurization of Sterically Hindered Analogs of Dibenzothiophene," *Appl. Environ. Microbiol.*, 61(12): 4362–4366 (Dec. 1995).
Kilbane, J.J. "Biodesulfurization: Future Prospects in Coal Cleaning," *Proc. 7th Ann. Int'l. Pittsburgh Coal Conf.*: 373–382 (Sep. 10–14, 1990).
Gray, K.A., et al., "Molecular mechanisms of biocatalytic desulfurization of fossil fuels," *Nature Biotech.*, 14: 1705–1709 (Dec. 1996).
Altschul, S.F., et al., "Basic Local Alignment Search Tool," *J. Mol. Biol.*, 215: 403–410 (1990).

(List continued on next page.)

*Primary Examiner*—Charles L. Patterson, Jr.
*Attorney, Agent, or Firm*—Hamilton, Brook, Smith & Reynolds, P.C.

[57] ABSTRACT

The present invention provides novel recombinant pseudomonads which contain a heterologous nucleic acid molecule comprising a nucleotide sequence encoding one or more desulfurization enzymes which are components of a biodesulfurization catalyst. The invention also provides a method of desulfurizing a carbonaceous material, such as a fossil fuel, which comprises organosulfur compounds. The method includes the steps of The method comprises the steps of (1) contacting the fossil fuel with an aqueous phase containing a recombinant biocatalyst which is capable of cleaving carbon-sulfur bonds and, optionally, a flavoprotein, thereby forming a fossil fuel and aqueous phase mixture; (2) maintaining the mixture under conditions sufficient for cleavage of the carbon-sulfur bonds of the organosulfur molecules by the biocatalyst, thereby resulting in a fossil fuel having a reduced organic sulfur content; and (3) separating the fossil fuel having a reduced organic sulfur content from the resulting aqueous phase.

53 Claims, 28 Drawing Sheets

OTHER PUBLICATIONS

Harris, R. and Knowles, C.J., "Isolation and Growth of a Pseudomonas Species that Utilizes Cyanide as a Source of Nitrogen," *J. Gen Microbiol.*, 129: 1005–1011 (1983).

Vieria, J. and Messing, J. "The pUC plasmids, an M13mp7–derived system for insertion mutagenesis and sequencing with synthetic universal primers," *Gene 19*: 259–268 (1982).

Frazee, R.W., et al., "Cloning, Sequencing, and Expression of the *Pseudomonas putida* Protocatechuate 3,4–Dioxygenase Genes," *J. Bacteriol.*, 175(19): 6194–6202 (Oct. 1993).

Hale, K. et al., "Multifunctional Regoulation of the Biological Effects of TNF–β By The Soluble Type I and Type II TNF Receptors," *Cytokine*, 7(1): 26–38 (1995).

Birboim, H.C. and Doly, J., a rapid alkline extraction procedure for screening recombinant plasmid DNA, *Nuc. Acids Res.*, 7(6): 1513–1523 (1979).

Yen, K.–W., "Construction of Cloning Cartridges for Development of Expression Vectors in Gram–Negative Bacteria," *J. Bacteriol.* 173: 5328–5335 (Sep. 1991).

Zenno, S. and Saigo, K., "Identification of the Genes Encoding NAD(P)–H–Flavin Oxidoreductases That Are Similar in Sequence to *Escherichia Coli* Fre in Four Species of Luminous Bacteria: Photohabdus Luminescens, *Vibrio fischeri, Vibrio harveyi,* and *Vibrio orientalis,*" *J. Bacteriol.* 176(12): 3544–3551, (1994).

```
ATG ACT CAA CAA CGA CAA ATG CAT CTG GCC GGT TTC TCG GCC GGC AAT GTG ACT CAT          60
Met Thr Gln Gln Arg Gln Met His Leu Ala Gly Phe Phe Ser Ala Gly Asn Val Thr His
                                      30

GCA CAT GGG GCG TGG CGG CAC ACG GAC GCG TCG AAT GAC TTT CTG TCG GGG AAG TAC TAC    120
Ala His Gly Ala Trp Arg His Thr Asp Ala Ser Asn Asp Phe Leu Ser Gly Lys Tyr Tyr
                    90                                      150

CAA CAC ATC GCC CGT ACT CTG GAG CGC GGC AAG TTC GAT CTG TTT CTG CCT GAC GGG        180
Gln His Ile Ala Arg Thr Leu Glu Arg Gly Lys Phe Asp Leu Phe Leu Pro Asp Gly Gly
                                      210

TTG GCC GTC GAG GAC AGC TAC GGG GAC AGT GGC AAC CTG GAC ACC GGT GTC GGC CTG GGC CAG    240
Leu Ala Val Glu Asp Ser Tyr Gly Asp Ser Val Ala Asn Leu Asp Thr Gly Val Gly Leu Gly Gln
                    270                                      300

GGT GCA GTC GCC TTG GAG CCG GCC AGT GTG GTC GCA ACC ATG GCC GTG ACC GAG CAC        300
Gly Ala Val Ala Leu Glu Pro Ala Ser Val Val Ala Thr Met Ala Ala Val Thr Glu His
                                      330

CTG GGT CTT GGG GCA ACC ATT TCG GCG ACC TAC TAT CCC CCG TAT CAC GTT GCT CGG GTG    360
Leu Gly Leu Gly Ala Thr Ile Ser Ala Thr Tyr Tyr Pro Pro Tyr His Val Ala Arg Val
                    390                                      420

TTC GCC ACG CTC GAT CAG TTG TCA GGG GGT CGG GTG TCC TGG AAC GTC GTC ACC TCG CTC
Phe Ala Thr Leu Asp Gln Leu Ser Gly Gly Arg Val Ser Trp Asn Val Val Thr Ser Leu
```

FIGURE 1A

```
AAC GCT GAA GCG CGC AAC TTC GGC ATT AAT CAG CAT CTG GAA CAC GAC GCC CGC TAT
Asn Asp Ala Glu Ala Arg Asn Phe Gly Ile Asn Gln His Leu Glu His Asp Ala Arg Tyr
                                    450                                      480

GAC CGC GCC GAT GAG TTC TTG GAA GCG GTC AAG AAA CTC TGG AAC AGC TGG GAC GAG GAC
Asp Arg Ala Asp Glu Phe Leu Glu Ala Val Lys Lys Leu Trp Asn Ser Trp Asp Glu Asp
                                    510                                      540

GCC CTC GTG CTG GAC AAG GCG GCC GGC GTG TTC GCC GAT CCC GCG AAG GTG CAC TAC GTC
Ala Leu Val Leu Asp Lys Ala Ala Gly Val Phe Ala Asp Pro Ala Lys Val His Tyr Val
                                    570                                      600

GAT CAC CAC GGG GAG TGG CTG AAT GTG CGC GGA CCT CTG CAG GTA CCG CGT TCA CCT CAG
Asp His His Gly Glu Trp Leu Asn Val Arg Gly Pro Leu Gln Val Pro Arg Ser Pro Gln
                                    630                                      660

GGT GAG CCG GTG ATC CTG CAG GCC CTG TCG CCC CGG GGT CGG CGC TTC GCC GGG AAG
Gly Glu Pro Val Ile Leu Gln Ala Leu Ser Pro Arg Gly Arg Arg Phe Ala Gly Lys
                                    690                                      720

TGG GCC GAG GTC TTC AGT CTT GCA CCC AAC CTC GAG ATG CAG GCC ACC TAC CAG
Trp Ala Glu Val Phe Ser Leu Ala Pro Asn Leu Glu Met Gln Ala Thr Tyr Gln
                                    750                                      780

GGC ATC AAA GCC GAG GTC GAC GCT GCG GGG CGC GAT CCC GAT CAG ACG AAA ATC TTC ACC
Gly Ile Lys Ala Glu Val Asp Ala Ala Gly Arg Asp Pro Asp Gln Thr Lys Ile Phe Thr
                                    810                                      840
```

```
                                                         870                                    900
GCC GTG ATG CCG GTA CTC GGC GAA AGC CAG GCG GTG GCA CAG GAA CGA CTG GAA TAT CTC
Ala Val Met Pro Val Leu Gly Glu Ser Gln Ala Val Ala Gln Glu Arg Leu Glu Tyr Leu 930                                    960
AAC AGT CTG GTC CAT CCG GAA GTG GGA CTG TCG ACG CTA TCC AGT CAC ACC GGC ATC AAC
Asn Ser Leu Val His Pro Glu Val Gly Leu Ser Thr Leu Ser Ser His Thr Gly Ile Asn 990                                   1020
CTG GCG TAC CCT CTC GAC ACT CCG ATC AAG GAC ATC CTG CGG GAT CTG CAG GAT CGG
Leu Ala Tyr Pro Leu Asp Thr Pro Ile Lys Asp Ile Leu Arg Asp Leu Gln Asp Arg 1050                                   1080
AAT GTC CCG ACG CAA CTG CAC ATG TTC GCC GCA ACG CAC AGC GAA GAG CTC ACG CTG
Asn Val Pro Thr Gln Leu His Met Phe Ala Ala Thr His Ser Glu Glu Leu Thr Leu 1110                                   1140
GCG GAA ATG GGT CGG TAT GGA ACC AAC GTG GGG TTC GTT CCT CAG TGG GCC GGT ACC
Ala Glu Met Gly Arg Tyr Gly Thr Asn Val Gly Phe Val Pro Gln Trp Ala Gly Thr 1170                                   1200
GGG GAG CAG ATC GCT GAC GAG CTG ATC CGC CAC TTC GAG GGC GCC GCG GAT GGT TTC
Gly Glu Gln Ile Ala Asp Glu Leu Ile Arg His Phe Glu Gly Ala Ala Asp Gly Phe 1230                                   1260
ATC ATC TCT CCG GCC TTC CTG CCG GGC TCC TAC GAC GAG TTC GTC GAC CAG GTG GTT CCG
Ile Ile Ser Pro Ala Phe Leu Pro Gly Ser Tyr Asp Glu Phe Val Asp Gln Val Val Pro
```

```
GTT CTG CAG GAT CGC GGC TAC TTC CGC ACC GAG TAC CAG GGC AAC ACT CTG CGC GAC CAC
Val Leu Gln Asp Arg Gly Tyr Phe Arg Thr Glu Tyr Gln Gly Asn Thr Leu Arg Asp His
                                     1290                              1320

TTG GGT CTG CGC GTA CCA CAA CTG CAA GGA CAA CCT TCA TGA
Leu Gly Leu Arg Val Pro Gln Leu Gln Gly Gln Pro Ser *
                     1350
```

FIGURE 1D

```
ATG ACA AGC CGC GTC GAC CCC GCA AAC CCC GGT TCA GAA CTC GAT TCC GCC ATC CGC GAC   60
Met Thr Ser Arg Val Asp Pro Ala Asn Pro Gly Ser Glu Leu Asp Ser Ala Ile Arg Asp

ACA CTG ACC TAC AGC AAC TGC CCG GTA CCC AAC GCT CTG CTC ACG GCA TCG GAA TCG GGC  120
Thr Leu Thr Tyr Ser Asn Cys Pro Val Pro Asn Ala Leu Leu Thr Ala Ser Glu Ser Gly

TTC CTC GAC GCC GCC GGC ATC GAA CTC GAC GTC CTC AGC GGC CAG CAG GGC ACG GTT CAT  180
Phe Leu Asp Ala Ala Gly Ile Glu Leu Asp Val Leu Ser Gly Gln Gln Gly Thr Val His

TTC ACC TAC GAC CAG CCT GCC TAC ACC CGT TTT GGG GGT GAG ATC CCG CCA CTG CTC AGC  240
Phe Thr Tyr Asp Gln Pro Ala Tyr Thr Arg Phe Gly Gly Glu Ile Pro Pro Leu Leu Ser

GAG GGG TTG CGG GCA CCT GGG CGC ACG CGT CTA CTC GGC ATC ACC CCG CTC TTG GGG CGC  300
Glu Gly Leu Arg Ala Pro Gly Arg Thr Arg Leu Leu Gly Ile Thr Pro Leu Leu Gly Arg

CAG GGC TTT GTC CGC GAC GAC AGC CCG ATC ACA GCG GCC GAC CTT GCC GGA CGT  360
Gln Gly Phe Val Arg Asp Asp Ser Pro Ile Thr Ala Ala Asp Leu Ala Gly Arg

CGA ATC GGC GTC TCG GCC GCA ATT CGC ATC CTG CGC GGC CAG CTG CGG CGA TAC CTC  420
Arg Ile Gly Val Ser Ala Ala Ile Arg Ile Leu Arg Gly Gln Leu Arg Gly Asp Tyr Leu
```

FIGURE 2A

GAG TTG GAT CCC TGG CGG CAA ACG CTG GTA GCC CTG GGC TCG TGG GAG GCG CGC GCC TTG
Glu Leu Asp Pro Trp Arg Gln Thr Leu Val Ala Leu Gly Ser Trp Glu Ala Arg Ala Leu
                                                                              480

TTG CAC ACC CTT GAG CAC GGT GAA CTG GGT GTG GAC GAC GTC GAG CTG GTG CCG ATC AGC
Leu His Thr Leu Glu His Gly Glu Leu Gly Val Asp Asp Val Glu Leu Val Pro Ile Ser
                                                                              540

AGT CCT GGT GTC GAT GTT CCC GCT GAG CAG CTC GAA GAA TCG GCG ACC GTC AAG GGT GCG
Ser Pro Gly Val Asp Val Pro Ala Glu Gln Leu Glu Glu Ser Ala Thr Val Lys Gly Ala
                                                                              600

GAC CTC TTT CCC GAT GTC GCC CGC GGT CAG CAG GCC GCG GTG TTG GCC AGC GGA GAC GTT GAC
Asp Leu Phe Pro Asp Val Ala Arg Gly Gln Gln Ala Ala Val Leu Ala Ser Gly Asp Val Asp
                                                                                  660

GCC CTG TAC AGT TGG CTG CCC TGG GCC TTG GAG CTC CAA GCC ACC GGG GCC CGC CCA GTG
Ala Leu Tyr Ser Trp Leu Pro Trp Ala Leu Glu Leu Gln Ala Thr Gly Ala Arg Pro Val
                                                                              720

GTG GAT CTC GGC CTC GAT GAG CGC AAT GCC TAC GCC AGT GTG TGG ACG GTC AGC AGC GGG
Val Asp Leu Gly Leu Asp Glu Arg Asn Ala Tyr Ala Ser Val Trp Thr Val Ser Ser Gly
                                                                              780

CTG GTT CGC CAG CGA CCT GGC CTT GTT CAA CGA CTG GTC GAC GCC GCC GTC GAC GCC GGG
Leu Val Arg Gln Arg Pro Gly Leu Val Gln Arg Leu Val Asp Ala Ala Val Asp Ala Gly
                                                                              840

FIGURE 2B

```
                                                  870                                           900
CTG TGG GCA CGC GAT CAT TCC GAC GCG GTG ACC AGC CTG CAC GCC GCG AAC CTG GGC GTA
Leu Trp Ala Arg Asp His Ser Asp Ala Val Thr Ser Leu His Ala Ala Asn Leu Gly Val 930                                           960
TCG ACC GGA GCA GTA GGC CAG GGC TTC GGC GCC GAC TTC CAG CAG CGT CTG GTT CCA CGC
Ser Thr Gly Ala Val Gly Gln Gly Phe Gly Ala Asp Phe Gln Gln Arg Leu Val Pro Arg 990                                          1020
CTG GAT CAC GAC GCC CTC GCC CTC CTG GAG CGC ACA CAG CAA TTC CTC ACC AAC AAC
Leu Asp His Asp Ala Leu Ala Leu Leu Glu Arg Thr Gln Gln Phe Leu Thr Asn Asn 1050                                          1080
TTG CTG CAG GAA CCC GTC GCC CTC GAT CAG TGG GCG GCT CCG GAA TTT CTG AAC AAC AGC
Leu Leu Gln Glu Pro Val Ala Leu Asp Gln Trp Ala Ala Pro Glu Phe Leu Asn Asn Ser

CTC AAT CGC CAC CGA TAG
Leu Asn Arg His Arg  *
```

FIGURE 2C

```
                                                    30                                             60
ATG ACA CTG TCA CCT GAA AAG CAG CAC CGA CCA CGC GAC GCC GAC AAC GAT CCC
Met Thr Leu Ser Pro Glu Lys Gln His Arg Pro Arg Asp Ala Asp Asn Asp Pro 90                                            120
GTC GCG GTT GCC CGT GGG CTA GCC GAA AAG TGG CGA GCC ACC GCC GTC GAT CGC
Val Ala Val Ala Arg Gly Leu Ala Glu Lys Trp Arg Ala Thr Ala Val Asp Arg 150                                            180
GCC GGG GGT TCG GCA ACA GCC GAG CGC GAA GAC CTG CGC GCG AGC GCG CTG CTC
Ala Gly Gly Ser Ala Thr Ala Glu Arg Glu Asp Leu Arg Ala Ser Ala Leu Leu 210                                            240
CTC GTC CCG CGC GAA TAC GGC GGC GCA GAC GGA TGG CCC ACC GCC ATC GAG GTC GTC
Leu Val Pro Arg Glu Tyr Gly Gly Ala Asp Trp Pro Thr Ala Ile Glu Val Val 270                                            300
CGC GAA ATC GCG GCA GCC GAT GGA TCT TTG GGA CAC CTG TTC GGA TAC CAC CTC ACC AAC
Arg Glu Ile Ala Ala Ala Asp Gly Ser Leu Gly His Leu Phe Gly Tyr His Leu Thr Asn 330                                            360
GCC CCG ATG ATC GAA CTG ATC GGC TCG CAG GAA CAA GAA CAC CTG TAC ACC CAG ATC
Ala Pro Met Ile Glu Leu Ile Gly Ser Gln Glu Gln Glu His Leu Tyr Thr Gln Ile 390                                            420
GCG CAG AAC AAC TGG ACC GGA AAT GCC TCC AGC GAG AAC AAC AGC CAC GTG CTG GAC
Ala Gln Asn Asn Trp Thr Gly Asn Ala Ser Ser Glu Asn Asn Ser His Val Leu Asp

FIGURE 3A
```

```
                                                                                           480
TGG AAG GTC AGC GCC ACC CCG ACC GAA GAC GGC TAC GTG CTC AAT GGC ACG AAG CAC
Trp Lys Val Ser Ala Thr Pro Thr Glu Asp Gly Tyr Val Leu Asn Gly Thr Lys His
                                    450

540
TTC TGC AGC GGC GCC AAG GGG TCG GAC CTG TTC GTG GGC GTC CAG GAT GAT
Phe Cys Ser Gly Ala Lys Gly Ser Asp Leu Phe Val Gly Val Gln Asp Asp
                                510

600
TCT CCG CAG CAG GGT GCG ATC ATT GCT GCC ATC CCG ACA TCG CGG GCT GGC GTT ACG
Ser Pro Gln Gln Gly Ala Ile Ile Ala Ala Ile Pro Thr Ser Arg Ala Gly Val Thr
                                    570

660
CCC AAC GAC GAC TGG GCC GCC ATC GGC ATG CGG CAG ACC GAC AGC GGT TCC ACG GAC TTC
Pro Asn Asp Asp Trp Ala Ala Ile Gly Met Arg Gln Thr Asp Ser Gly Ser Thr Asp Phe
                                        630

720
CAC AAC GTC AAG GTC GAG CCT GAC GAA GTG CTG GGC GCG CCC AAC GCC TTC GTT CTC GCC
His Asn Val Lys Val Glu Pro Asp Glu Val Leu Gly Ala Pro Asn Ala Phe Val Leu Ala
                                        690

780
TTC ATA CAA TCC GAG CGC GGC AGC CTC TTC GCG CCC ATA GCG CAA TTG ATC TTC GCC AAC
Phe Ile Gln Ser Glu Arg Gly Ser Leu Phe Ala Pro Ile Ala Gln Leu Ile Phe Ala Asn
                                        750

840
GTC TAT CTG GGG ATC GCC CAC GGC GCA CTC GAT GCC GCC AGG GAG TAC ACC CGT ACC CAG
Val Tyr Leu Gly Ile Ala His Gly Ala Leu Asp Ala Ala Arg Glu Tyr Thr Arg Thr Gln
                                        810
```

FIGURE 3B

```
GCG AGG CCC TGG ACA CCG GCC GGT ATT CAA CAG GCA ACC GAG GAT CCC TAC ACC ATC CGC
Ala Arg Pro Trp Thr Pro Ala Gly Ile Gln Gln Ala Thr Glu Asp Pro Tyr Thr Ile Arg
                                        870                                 900

TCC TAC GGT GAG TTC ACC ATC GCA TTG CAG GGA GCT GAC GCC CGT GAA GCG GCC
Ser Tyr Gly Glu Phe Thr Ile Ala Leu Gln Gly Ala Asp Ala Arg Glu Ala Ala
                        930                                 960

CAC CTG CTG CAG ACG GTG TGG GAC AAG GGC GAC GCG CTC ACC CCC GAG GAC CGC GGC GAA
His Leu Leu Gln Thr Val Trp Asp Lys Gly Asp Ala Leu Thr Pro Glu Asp Arg Gly Glu
                                        990                                1020

CTG ATG GTG AAG GTC TCG GGA GTC AAA GCG TTG GCC ACC AAC GCC GCC CTC AAC ATC AGC
Leu Met Val Lys Val Ser Gly Val Lys Ala Leu Ala Thr Asn Ala Ala Leu Asn Ile Ser
                        1050                                1080

AGC GGC GTC TTC GAG GTG ATC GGC GCG CGC GGA ACA CAT CCC AGG TAC GGT TTC GAC CGC
Ser Gly Val Phe Glu Val Ile Gly Ala Arg Gly Thr His Pro Arg Tyr Gly Phe Asp Arg
                                        1110                                1200

TTC TGG CGC AAC GTG CGC ACC CAC TCC CTG CAC GAC CCG GTG TCC TAC TAC AAG ATC GCC GAC
Phe Trp Arg Asn Val Arg Thr His Ser Leu His Asp Pro Val Ser Tyr Tyr Lys Ile Ala Asp
                        1170

GTC GGC AAG CAC ACC TTG AAC GGT CAA TAC CCG ATT CCC GGC TTC ACC TCC TGA
Val Gly Lys His Thr Leu Asn Gly Gln Tyr Pro Ile Pro Gly Phe Thr Ser *
                        1230
```

FIGURE 3C

```
ATG ACC GAT CCA CGT CAG CTG CAC CTG GCC GGA TTC TTC TGT GCC GGC AAC GTC ACG CAC     60
Met Thr Asp Pro Arg Gln Leu His Leu Ala Gly Phe Phe Cys Ala Gly Asn Val Thr His

GCC CAC GGA GCG TGG CGC CAC GCC GAC TCC AAC GGC TTC CTC ACC AAG GAG TAC TAC        120
Ala His Gly Ala Trp Arg His Ala Asp Ser Asn Gly Phe Leu Thr Lys Glu Tyr Tyr

CAG CAG ATT GCC CGC ACG CTC GAG CGC GGC AAG TTC GAC CTG CTG TTC CCC GAC GCG        180
Gln Gln Ile Ala Arg Thr Leu Glu Arg Gly Lys Phe Asp Leu Leu Phe Pro Asp Ala

CTC GCC GTG TGG GAC AGC TAC GGT GAC AAT CTG GTA ATC GCC GCG ACC GGT CTG CAA        240
Leu Ala Val Trp Asp Ser Tyr Gly Asp Asn Leu Val Ile Ala Ala Thr Gly Leu Gln

GGC GCG GTG ATG CTG GAG CCC GGC GTA ATC GCC GCG ATG GCC TCG GTG ACC GAA CAT        300
Gly Ala Val Met Leu Glu Pro Gly Val Ile Ala Ala Met Ala Ser Val Thr Glu His

CTG GGG CTG GGC GCC ACC ATT TCC ACC TAC TAC CCG CCC TAC CAT GTA GCC CGG GTC        360
Leu Gly Leu Gly Ala Thr Ile Ser Thr Tyr Tyr Pro Pro Tyr His Val Ala Arg Val

GTC GCT TCG CTG GAC CAG CTG TCC TCC GGG CGA GTG TCG TGG AAC GTG GTC ACC TCG CTC    420
Val Ala Ser Leu Asp Gln Leu Ser Ser Gly Arg Val Ser Trp Asn Val Val Thr Ser Leu
```

FIGURE 4A

```
AGC AAT GCA GAG GCG CGC AAC TTC GGC GAT GAA CAT CTC GAC CAT GAT GCC CGC TAC
Ser Asn Ala Glu Ala Arg Asn Phe Gly Asp Glu His Leu Asp His Asp Ala Arg Tyr
                                            450                              490

GAT CGC GCC GAT GAA TTC CTC GAG GTC CGC AAG CTC TGG AAC AGC TGG GAT CGC GAT
Asp Arg Ala Asp Glu Phe Leu Glu Val Arg Lys Leu Trp Asn Ser Trp Asp Arg Asp
                                            510                              540

GCG CTG ACA CTC GAC AAG GCA ACC GGC CAG TTC GCC GAT CCG GCT AAG GTG TAC ATC
Ala Leu Thr Leu Asp Lys Ala Thr Gly Gln Phe Ala Asp Pro Ala Lys Val Tyr Ile
                                            570                              600

GAC CAC CGC GGC GAA TGG CTC AAC GTA CGG GGG CCG CTT CAG GTG CCG CGC TCC CCC CAG
Asp His Arg Gly Glu Trp Leu Asn Val Arg Gly Pro Leu Gln Val Pro Arg Ser Pro Gln
                                            630                              660

GGC GAG CCT GTC ATT CTG CAG GCC GGG CTT TCG GCG CGG GGC AAG CGC TTC GCC GGG CGC
Gly Glu Pro Val Ile Leu Gln Ala Gly Leu Ser Ala Arg Gly Lys Arg Phe Ala Gly Arg
                                            690                              720

TGG GCG GAC GCG GTG TTC ACG ATT TCG CCC AAT CTG GAC ATC ATG CAG GCC ACG TAC CGC
Trp Ala Asp Ala Val Phe Thr Ile Ser Pro Asn Leu Asp Ile Met Gln Ala Thr Tyr Arg
                                            750                              780

GAC ATA AAG GCG CAG GTC GAG GCC GGA CGC GAT CCC GAG CAG GTC AAG GTG TTT GCC
Asp Ile Lys Ala Gln Val Glu Ala Gly Arg Asp Pro Glu Gln Val Lys Val Phe Ala
                                            810                              840
```

FIGURE 4B

```
GCG GTG ATG CCG ATC CTC GGC GAG ACC GAG GCG ATC GCC AGG CAG CGT CTC GAA TAC ATA
Ala Val Met Pro Ile Leu Gly Glu Thr Glu Ala Ile Ala Arg Gln Arg Leu Glu Tyr Ile
                                   870                              900

AAT TCG CTG GTG CAT CCC GAA GTC GGG CTT TCT ACG TTG TCC AGC CAT GTC GGG GTC AAC
Asn Ser Leu Val His Pro Glu Val Gly Leu Ser Thr Leu Ser Ser His Val Gly Val Asn
                                   930                              960

CTT GCC GAC TAT TCG CTC GAT ACC CCG GAA GTC CTG ACC GAG GTC CTG GGC GAT CTC GCC CAG CGC
Leu Ala Asp Tyr Ser Leu Asp Thr Pro Glu Val Leu Thr Glu Val Leu Gly Asp Leu Ala Gln Arg
                                   990                             1020

AAC GTG CCC ACC CAA CTG GGC ATG TTC GCC AGG ATG TTG CAG GCC GAG ACG CTG ACC GTG
Asn Val Pro Thr Gln Leu Gly Met Phe Ala Arg Met Leu Gln Ala Glu Thr Leu Thr Val
                                  1050                             1080

GGA GAA ATG GGC CGG CGT TAT GGC GCC AAC GTG GGC TTC GTC CCG CAG TGG GCG GGA ACC
Gly Glu Met Gly Arg Arg Tyr Gly Ala Asn Val Gly Phe Val Pro Gln Trp Ala Gly Thr
                                  1110                             1140

CGC GAG CAG ATC GCG GAC CTG ATC GAG ATC CAT TTC AAG GCC GGC GCC GAT GGC TTC
Arg Glu Gln Ile Ala Asp Leu Ile Glu Ile His Phe Lys Ala Gly Ala Asp Gly Phe
                                  1170                             1200

ATC ATC TCG CCG GCG TTC CTG CCC GGA TCT TAC GAG GAA TTC GTC GAT CAG GTG GTG CCC
Ile Ile Ser Pro Ala Phe Leu Pro Gly Ser Tyr Glu Glu Phe Val Asp Gln Val Val Pro
                                  1230                             1260
```

FIGURE 4C

```
ATC CTG CAG CAC CGC GGA CTG TTC CGC ACT GAT TAC GAA GGC CGC ACC CTG CGC AGC CAT
Ile Leu Gln His Arg Gly Leu Phe Arg Thr Asp Tyr Glu Gly Arg Thr Leu Arg Ser His
                                1290                                        1320

CTG GGA CTG CGT GAA CCC GCA TAC CTG GGA GAG TAC GCA TGA
Leu Gly Leu Arg Glu Pro Ala Tyr Leu Gly Glu Tyr Ala  *
                    1350
```

FIGURE 4D

```
ATG ACG ACA GAC ATC CAC CCG GCG AGC GCA TCG TCG CCG GCG CGC GCG ACG ATC   60
Met Thr Thr Asp Ile His Pro Ala Ser Ala Ser Ser Pro Ala Arg Ala Thr Ile

ACC TAC AGC AAC TGC CCC GTG CCT AAT GCC CTG CTC GCC CTC GGC TCA GGT ATT CTG  120
Thr Tyr Ser Asn Cys Pro Val Pro Asn Ala Leu Leu Ala Leu Gly Ser Gly Ile Leu

GAC AGT GCC GGG ATC ACA CTT GCC CTG ACC GGA AAG CAG GGC GAG GTG CAC TTC ACC  180
Asp Ser Ala Gly Ile Thr Leu Ala Leu Thr Gly Lys Gln Gly Glu Val His Phe Thr

TAC GAC CGA GAT GAC TAC ACC CGC TTC GGC GAG ATT CCG CTG ACG CCG GTC AGC GAG GGA  240
Tyr Asp Arg Asp Asp Tyr Thr Arg Phe Gly Glu Ile Pro Leu Thr Pro Val Ser Glu Gly

CTG CGT GCG CCG GGG CGG ACC CGC CTG GGA CTG CTG ACG CCG GTG CTG GGC CGC TGG GGC  300
Leu Arg Ala Pro Gly Arg Thr Arg Leu Gly Leu Leu Thr Pro Val Leu Gly Arg Trp Gly

TAC TTC GTC CGG GAC AGC GCG ATC GCC ACC CCG GCC GAT CTT GCC GCC CGC CGC GTC  360
Tyr Phe Val Arg Asp Ser Ala Ile Arg Thr Pro Ala Asp Leu Ala Gly Arg Arg Val

GGA GTA TCC GAT TCG GCC AGG AGG ATA TTG ACC GGA AGG CTG GGC GAC TAC CGC GAA CTT  420
Gly Val Ser Asp Ser Ala Arg Arg Ile Leu Thr Gly Arg Leu Gly Asp Tyr Arg Glu Leu
```

FIGURE 5A

```
                                                    450                           490
GAT CCC TGG CGG CAG ACC CTG GTC GCG CTG GGG ACA TGG GAG GCG CGT GCC TTG CTG AGC
Asp Pro Trp Arg Gln Thr Leu Val Ala Leu Gly Thr Trp Glu Ala Arg Ala Leu Leu Ser 510                           540
ACG CTC GAG ACG GCG GGG CTT GGC GTC GAC GGC GTC GAG GAC ATC GAG AAC CCG
Thr Leu Glu Thr Ala Gly Leu Gly Val Asp Gly Val Glu Asp Ile Glu Asn Pro 570                           600                           
TTC GTC GAC GTG CCG ACC GAA CGA CTG CAT GCC GCC GGC TCG CTC AAA GGA ACC GAC CTG
Phe Val Asp Val Pro Thr Glu Arg Leu His Ala Ala Gly Ser Leu Lys Gly Thr Asp Leu 630                           660
TTC CCC GAC GTG ACC AGC CAG CAG CTG GCA GTC CTT GAG GAT GAG CGC GAC GCC CTG
Phe Pro Asp Val Thr Ser Gln Gln Leu Ala Val Leu Glu Asp Glu Arg Asp Ala Leu 690                           720
TTC GCG TGG CTT CCC TGG GCG GCC GAG CTC GAG ACC CGC ATC GGT GCA CGG CCG GTC CTA
Phe Ala Trp Leu Pro Trp Ala Ala Glu Leu Glu Thr Arg Ile Gly Ala Arg Pro Val Leu 750                           780
GAC CTC AGC GCA GAC GAC CGC AAT GCC TAT GCG AGC ACC TGG ACG GTG AGC GCC GAG CTG
Asp Leu Ser Ala Asp Asp Arg Asn Ala Tyr Ala Ser Thr Trp Thr Val Ser Ala Glu Leu 810                           840
GTG GAC CGG CAG CCC GAA CTG GTG CAG CGG CTC GTC GAT GCC GTG GTG GAT GCA GGG CGG
Val Asp Arg Gln Pro Glu Leu Val Gln Arg Leu Val Asp Ala Val Val Asp Ala Gly Arg
```

FIGURE 5B

```
                                                                       900
TGG GCC GAG GCC AAT GGC GAT GTC GTC TCC CGC CTG CAC GCC GAT AAC CTC GGT GTC AGT
Trp Ala Glu Ala Asn Gly Asp Val Val Ser Arg Leu His Ala Asp Asn Leu Gly Val Ser

960
CCC GAA AGC GTC CGC CAG GGA TTC GGA GCC GAT TTT CAC CGC CGC CTG ACG CCG CGG CTC
Pro Glu Ser Val Arg Gln Gly Phe Gly Ala Asp Phe His Arg Arg Leu Thr Pro Arg Leu

1020
GAC AGC GAT GCT ATC GCC ATC CTG GAG CGT ACT CAG CGG TTC CTG AAG GAT GCG AAC CTG
Asp Ser Asp Ala Ile Ala Ile Leu Glu Arg Thr Gln Arg Phe Leu Lys Asp Ala Asn Leu

1080
ATC GAT CGG TCG TTG GCG CTC GAT CGG CTG GCT GCA CCT GAA TTC CTC GAA CAA AGT CTC
Ile Asp Arg Ser Leu Ala Leu Asp Arg Trp Ala Ala Pro Glu Phe Leu Glu Gln Ser Leu

1110
TCA CGC CAG GTC GAA GGG CAG ATA GCA TGA
Ser Arg Gln Val Glu Gly Gln Ile Ala *
```

FIGURE 5C

```
ATG AAC GAA CTC GTC AAA GAT CTC GGC CTC AAT CGA TCC GAT CCG ATC GGC GCT GTG CGG      60
Met Asn Glu Leu Val Lys Asp Leu Gly Leu Asn Arg Ser Asp Pro Ile Gly Ala Val Arg
                          30

CGA CTG GCC GCG CAG TGG GGG GCC ACC GCT GTT GAT CGG GAC CGG GCC GGA TCG GCA     120
Arg Leu Ala Ala Gln Trp Gly Ala Thr Ala Val Asp Arg Asp Arg Ala Gly Ser Ala
                          90

ACC GCC GAA CTC GAT CAA CTG CGC GGC CTG AGC GGC CTG CTC TCG CTG ATT CCC GCC GCA     180
Thr Ala Glu Leu Asp Gln Leu Arg Gly Leu Ser Gly Leu Leu Ser Leu Ile Pro Ala Ala
                         150

TAT GGC GGA TCG GGG GCC GAC TGG CCA GAT CAT CTA ACG ACT CTG GAA GTT ATC CGC GCA ACG     240
Tyr Gly Gly Trp Gly Ala Asp Trp Pro Asp His Leu Thr Thr Leu Glu Val Ile Arg Ala Thr
                         210

GTG GAC GGA TCG CTG CTG GCG CAT CTA TTC GGC TAC CAC CTC GGC TGC GTA CCG ATG ATC GAG     300
Val Asp Gly Ser Leu Leu Ala His Leu Phe Gly Tyr His Leu Gly Cys Val Pro Met Ile Glu
                         270

CTG TTC GGC TCG GCG CCA CAA AAG GAA CGG CTG TAC CGC CAG ATC GCA AGC CAT GAT TGG     360
Leu Phe Gly Ser Ala Pro Gln Lys Glu Arg Leu Tyr Arg Gln Ile Ala Ser His Asp Trp
                         330

CGG GTC GGG AAT GCG TCG AGC GAA AAC AGC CAC GTG CTC GAG TGG AAG CTT GCC GCC     420
Arg Val Gly Asn Ala Ser Ser Glu Asn Ser His Val Leu Glu Trp Lys Leu Ala Ala
                         390
```

FIGURE 6A

```
ACC GCC GTC GAT GAT GGC GGG TTC GTC AAC CTC GCG AAG CAC TTC TGC AGC GGC GCC   480
Thr Ala Val Asp Asp Gly Gly Phe Val Asn Leu Ala Lys His Phe Cys Ser Gly Ala

AAA AGC TCC GAC CTG CTC ATC GTG TTC GGC ATC CAG GAC GAA TCC CCC CTG CGC GGC   540
Lys Ser Ser Asp Leu Leu Ile Val Phe Gly Val Ile Gln Asp Glu Ser Pro Leu Arg Gly

GCG ATC ATC ACC GCG GTC ATT CCC ACC GAC CGG GCC GGT GTT CAG ATC AAT GAC GAC TGG   600
Ala Ile Ile Thr Ala Val Ile Pro Thr Asp Arg Ala Gly Val Gln Ile Asn Asp Asp Trp

CGC GCA ATC GGG ATG CGC CAG ACC GAC AGC GGC AGC GCC GAA TTT CGC GAC GTC CGA GTC   660
Arg Ala Ile Gly Met Arg Gln Thr Asp Ser Gly Ser Ala Glu Phe Arg Asp Val Arg Val

TAC CCA GAC GAG ATC TTG GGG GCA CCA AAC TCA GTC GTT GAG GCG TTC ACA AGC AAC   720
Tyr Pro Asp Glu Ile Leu Gly Ala Pro Asn Ser Val Val Glu Ala Phe Thr Ser Asn

CGC GGC AGC CTG TGG ACG CCG GCG ATT CAG TCG ATC TTC TCG AAC GTT TAT CTG GGG CTC   780
Arg Gly Ser Leu Trp Thr Pro Ala Ile Gln Ser Ile Phe Ser Asn Val Tyr Leu Gly Leu

GCG CGT GGC GCG CTC GAG GCG GCA GCG GAT TAC ACC CGG ACC CAG AGC CGC CCC TGG ACA   840
Ala Arg Gly Ala Leu Glu Ala Ala Ala Asp Tyr Thr Arg Thr Gln Ser Arg Pro Trp Thr
```

FIGURE 6B

```
CCC GCC GGC GTG GCG AAG GCG ACA GAG GAT CCC CAC ATC ATC GCC ACC TAC GGT GAA CTG
Pro Ala Gly Val Ala Lys Ala Thr Glu Asp Pro His Ile Ile Ala Thr Tyr Gly Glu Leu
                                       870                                   900

GCG ATC GCG CTC CAG GGC GCC GAG GCG CGC GCC GAG GTC GCG CTG TTG CAA CAG
Ala Ile Ala Leu Gln Gly Ala Glu Ala Arg Ala Ala Arg Glu Val Ala Leu Leu Gln Gln
                                       930                                   960

GCG TGG GAC AAG GGC GAT GCG ACG GTG CCC GAA GAG CGC GGC CAG CTG ATG GTG AAG GTT
Ala Trp Asp Lys Gly Asp Ala Val Thr Pro Glu Glu Arg Gly Gln Leu Met Val Lys Val
                                       990                                  1020

TCG GGT GTG AAG GCC CTC TCG ACG AAG GCC CTC GAC ATC ACC AGC CGT ATT TTC GAG
Ser Gly Val Lys Ala Leu Ser Thr Lys Ala Leu Asp Ile Thr Ser Arg Ile Phe Glu
                                      1050                                  1080

ACA ACG GGC TCG CGA TCG ACG CAT CCC AGA TAC GGA TTC GAT CGG TTC TGG CGT AAC ATC
Thr Thr Gly Ser Arg Ser Thr His Pro Arg Tyr Gly Phe Asp Arg Phe Trp Arg Asn Ile
                                      1110                                  1140

CGG ACT CAT ACG CTG CAC GAT CCG GTA TCG TAT AAA ATC GTC GAT GTG GGG AAC TAC ACG
Arg Thr His Thr Leu His Asp Pro Val Ser Tyr Lys Ile Val Asp Val Gly Asn Tyr Thr
                                      1170                                  1200

CTC AAC GGG ACA TTC CCG GTT CCC GGA TTT ACG TCA
Leu Asn Gly Thr Phe Pro Val Pro Gly Phe Thr Ser
                                      1230
```

FIGURE 6C

```
       BamHI SpeI Bsu361        BseRI             BsmI    SphI SnaBI   PacI   SpeI   HindIII
5' GATCCACTAGTCCTGAGGACATCCATGAGGAGATAACCGATGTCTGACAAGCCGAATGCCGATGCTACGTATTAATTAAACTAGTA   3'
3'     GTGATCAGGACTCCTGTAGGTACTCCTCTATTGGCTACAGACTGTTCGGCTTACGGCTACGATGCATAATTAATTTGATCATTCCA   5'
                                    MetSerAspLysProAsnAla
```

FIGURE 18

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 1359 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1359

(xi) SEQUENCE DESCRIPTION: SEQ ID NO:1:

```
ATG ACT CAA CAA CGA CAA ATG CAT CTG GCC GGT TTC TTC TCG GCC GGC        48
Met Thr Gln Gln Arg Gln Met His Leu Ala Gly Phe Phe Ser Ala Gly
 1               5                  10                  15

AAT GTG ACT CAT GCA CAT GGG GCG TGG CGG CAC ACG GAC GCG TCG AAT        96
Asn Val Thr His Ala His Gly Ala Trp Arg His Thr Asp Ala Ser Asn
            20                  25                  30

GAC TTT CTG TCG GGG AAG TAC TAC CAA CAC ATC GCC CGT ACT CTG GAG       144
Asp Phe Leu Ser Gly Lys Tyr Tyr Gln His Ile Ala Arg Thr Leu Glu
        35                  40                  45

CGC GGC AAG TTC GAT CTG TTG TTT CTG CCT GAC GGG TTG GCC GTC GAG       192
Arg Gly Lys Phe Asp Leu Leu Phe Leu Pro Asp Gly Leu Ala Val Glu
 50                  55                  60

GAC AGC TAC GGG GAC AAC CTG GAC ACC GGT GTC GGC CTG GGC GGG CAG       240
Asp Ser Tyr Gly Asp Asn Leu Asp Thr Gly Val Gly Leu Gly Gly Gln
 65                  70                  75                  80

GGT GCA GTC GCC TTG GAG CCG GCC AGT GTG GTC GCA ACC ATG GCC GCG       288
Gly Ala Val Ala Leu Glu Pro Ala Ser Val Val Ala Thr Met Ala Ala
                85                  90                  95

GTG ACC GAG CAC CTG GGT CTT GGG GCA ACC ATT TCG GCG ACC TAC TAT       336
Val Thr Glu His Leu Gly Leu Gly Ala Thr Ile Ser Ala Thr Tyr Tyr
            100                 105                 110

CCC CCG TAT CAC GTT GCT CGG GTG TTC GCG ACG CTC GAT CAG TTG TCA       384
Pro Pro Tyr His Val Ala Arg Val Phe Ala Thr Leu Asp Gln Leu Ser
        115                 120                 125

GGG GGT CGG GTG TCC TGG AAC GTC GTC ACC TCG CTC AAC GAC GCT GAA       432
Gly Gly Arg Val Ser Trp Asn Val Val Thr Ser Leu Asn Asp Ala Glu
```

-continued

|  |  | 130 |  |  |  | 135 |  |  |  | 140 |  |  |  |  |  |
|---|---|---|---|---|---|---|---|---|---|---|---|---|---|---|---|

```
GCG CGC AAC TTC GGC ATT AAT CAG CAT CTG GAA CAC GAC GCC CGC TAT        480
Ala Arg Asn Phe Gly Ile Asn Gln His Leu Glu His Asp Ala Arg Tyr
145             150                 155                 160

GAC CGC GCC GAT GAG TTC TTG GAA GCG GTC AAG AAA CTC TGG AAC AGC        528
Asp Arg Ala Asp Glu Phe Leu Glu Ala Val Lys Lys Leu Trp Asn Ser
                165                 170                 175

TGG GAC GAG GAC GCC CTC GTG CTG GAC AAG GCG GCC GGC GTG TTC GCC        576
Trp Asp Glu Asp Ala Leu Val Leu Asp Lys Ala Ala Gly Val Phe Ala
            180                 185                 190

GAT CCC GCG AAG GTG CAC TAC GTC GAT CAC CAC GGG GAG TGG CTG AAT        624
Asp Pro Ala Lys Val His Tyr Val Asp His His Gly Glu Trp Leu Asn
        195                 200                 205

GTG CGC GGA CCT CTG CAG GTA CCG CGT TCA CCT CAG GGT GAG CCG GTG        672
Val Arg Gly Pro Leu Gln Val Pro Arg Ser Pro Gln Gly Glu Pro Val
210                 215                 220

ATC CTG CAG GCC GGC CTG TCG CCC CGG GGT CGG CGC TTC GCC GGG AAG        720
Ile Leu Gln Ala Gly Leu Ser Pro Arg Gly Arg Arg Phe Ala Gly Lys
225                 230                 235                 240

TGG GCC GAG GCC GTC TTC AGT CTT GCA CCC AAC CTC GAG GTG ATG CAG        768
Trp Ala Glu Ala Val Phe Ser Leu Ala Pro Asn Leu Glu Val Met Gln
                245                 250                 255

GCC ACC TAC CAG GGC ATC AAA GCC GAG GTC GAC GCT GCG GGG CGC GAT        816
Ala Thr Tyr Gln Gly Ile Lys Ala Glu Val Asp Ala Ala Gly Arg Asp
            260                 265                 270

CCC GAT CAG ACG AAA ATC TTC ACC GCC GTG ATG CCG GTA CTC GGC GAA        864
Pro Asp Gln Thr Lys Ile Phe Thr Ala Val Met Pro Val Leu Gly Glu
        275                 280                 285

AGC CAG GCG GTG GCA CAG GAA CGA CTG GAA TAT CTC AAC AGT CTG GTC        912
Ser Gln Ala Val Ala Gln Glu Arg Leu Glu Tyr Leu Asn Ser Leu Val
    290                 295                 300

CAT CCG GAA GTG GGA CTG TCG ACG CTA TCC AGT CAC ACC GGC ATC AAC        960
His Pro Glu Val Gly Leu Ser Thr Leu Ser Ser His Thr Gly Ile Asn
305                 310                 315                 320

CTG GCG GCG TAC CCT CTC GAC ACT CCG ATC AAG GAC ATC CTG CGG GAT       1008
Leu Ala Ala Tyr Pro Leu Asp Thr Pro Ile Lys Asp Ile Leu Arg Asp
                325                 330                 335

CTG CAG GAT CGG AAT GTC CCG ACG CAA CTG CAC ATG TTC GCC GCC GCA       1056
Leu Gln Asp Arg Asn Val Pro Thr Gln Leu His Met Phe Ala Ala Ala
            340                 345                 350

ACG CAC AGC GAA GAG CTC ACG CTG GCG GAA ATG GGT CGG CGC TAT GGA       1104
Thr His Ser Glu Glu Leu Thr Leu Ala Glu Met Gly Arg Arg Tyr Gly
        355                 360                 365

ACC AAC GTG GGG TTC GTT CCT CAG TGG GCC GGT ACC GGG GAG CAG ATC       1152
Thr Asn Val Gly Phe Val Pro Gln Trp Ala Gly Thr Gly Glu Gln Ile
    370                 375                 380

GCT GAC GAG CTG ATC CGC CAC TTC GAG GGC GGC GCC GCG GAT GGT TTC       1200
Ala Asp Glu Leu Ile Arg His Phe Glu Gly Gly Ala Ala Asp Gly Phe
385                 390                 395                 400

ATC ATC TCT CCG GCC TTC CTG CCG GGC TCC TAC GAC GAG TTC GTC GAC       1248
Ile Ile Ser Pro Ala Phe Leu Pro Gly Ser Tyr Asp Glu Phe Val Asp
                405                 410                 415

CAG GTG GTT CCG GTT CTG CAG GAT CGC GGC TAC TTC CGC ACC GAG TAC       1296
Gln Val Val Pro Val Leu Gln Asp Arg Gly Tyr Phe Arg Thr Glu Tyr
            420                 425                 430

CAG GGC AAC ACT CTG CGC GAC CAC TTG GGT CTG CGC GTA CCA CAA CTG       1344
Gln Gly Asn Thr Leu Arg Asp His Leu Gly Leu Arg Val Pro Gln Leu
        435                 440                 445

CAA GGA CAA CCT TCA                                                    1359
Gln Gly Gln Pro Ser
```

450

(2) INFORMATION FOR SEQ ID NO:2:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Gln Gln Arg Gln Met His Leu Ala Gly Phe Phe Ser Ala Gly
  1               5                  10                  15

Asn Val Thr His Ala His Gly Ala Trp Arg His Thr Asp Ala Ser Asn
             20                  25                  30

Asp Phe Leu Ser Gly Lys Tyr Tyr Gln His Ile Ala Arg Thr Leu Glu
         35                  40                  45

Arg Gly Lys Phe Asp Leu Leu Phe Leu Pro Asp Gly Leu Ala Val Glu
     50                  55                  60

Asp Ser Tyr Gly Asp Asn Leu Asp Thr Gly Val Gly Leu Gly Gly Gln
 65                  70                  75                  80

Gly Ala Val Ala Leu Glu Pro Ala Ser Val Val Ala Thr Met Ala Ala
                 85                  90                  95

Val Thr Glu His Leu Gly Leu Gly Ala Thr Ile Ser Ala Thr Tyr Tyr
            100                 105                 110

Pro Pro Tyr His Val Ala Arg Val Phe Ala Thr Leu Asp Gln Leu Ser
            115                 120                 125

Gly Gly Arg Val Ser Trp Asn Val Val Thr Ser Leu Asn Asp Ala Glu
        130                 135                 140

Ala Arg Asn Phe Gly Ile Asn Gln His Leu Glu His Asp Ala Arg Tyr
145                 150                 155                 160

Asp Arg Ala Asp Glu Phe Leu Glu Ala Val Lys Lys Leu Trp Asn Ser
                165                 170                 175

Trp Asp Glu Asp Ala Leu Val Leu Asp Lys Ala Ala Gly Val Phe Ala
            180                 185                 190

Asp Pro Ala Lys Val His Tyr Val Asp His His Gly Glu Trp Leu Asn
        195                 200                 205

Val Arg Gly Pro Leu Gln Val Pro Arg Ser Pro Gln Gly Glu Pro Val
    210                 215                 220

Ile Leu Gln Ala Gly Leu Ser Pro Arg Gly Arg Phe Ala Gly Lys
225                 230                 235                 240

Trp Ala Glu Ala Val Phe Ser Leu Ala Pro Asn Leu Glu Val Met Gln
                245                 250                 255

Ala Thr Tyr Gln Gly Ile Lys Ala Glu Val Asp Ala Ala Gly Arg Asp
            260                 265                 270

Pro Asp Gln Thr Lys Ile Phe Thr Ala Val Met Pro Val Leu Gly Glu
        275                 280                 285

Ser Gln Ala Val Ala Gln Glu Arg Leu Glu Tyr Leu Asn Ser Leu Val
    290                 295                 300

His Pro Glu Val Gly Leu Ser Thr Leu Ser Ser His Thr Gly Ile Asn
305                 310                 315                 320

Leu Ala Ala Tyr Pro Leu Asp Thr Pro Ile Lys Asp Ile Leu Arg Asp
                325                 330                 335

Leu Gln Asp Arg Asn Val Pro Thr Gln Leu His Met Phe Ala Ala Ala
            340                 345                 350
```

```
Thr His Ser Glu Glu Leu Thr Leu Ala Glu Met Gly Arg Arg Tyr Gly
        355                 360                 365

Thr Asn Val Gly Phe Val Pro Gln Trp Ala Gly Thr Gly Glu Gln Ile
        370                 375                 380

Ala Asp Glu Leu Ile Arg His Phe Glu Gly Ala Ala Asp Gly Phe
385                 390                 395                 400

Ile Ile Ser Pro Ala Phe Leu Pro Gly Ser Tyr Asp Glu Phe Val Asp
                405                 410                 415

Gln Val Val Pro Val Leu Gln Asp Arg Gly Tyr Phe Arg Thr Glu Tyr
                420                 425                 430

Gln Gly Asn Thr Leu Arg Asp His Leu Gly Leu Arg Val Pro Gln Leu
            435                 440                 445

Gln Gly Gln Pro Ser
        450
```

(2) INFORMATION FOR SEQ ID NO:3:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1095

(xi) SEQUENCE DESCRIPTION: SEQ ID NO:3:

```
ATG ACA AGC CGC GTC GAC CCC GCA AAC CCC GGT TCA GAA CTC GAT TCC      48
Met Thr Ser Arg Val Asp Pro Ala Asn Pro Gly Ser Glu Leu Asp Ser
 1               5                  10                  15

GCC ATC CGC GAC ACA CTG ACC TAC AGC AAC TGC CCG GTA CCC AAC GCT      96
Ala Ile Arg Asp Thr Leu Thr Tyr Ser Asn Cys Pro Val Pro Asn Ala
                20                  25                  30

CTC CTC ACG GCA TCG GAA TCG GGC TTC CTC GAC GCC GCC GGC ATC GAA     144
Leu Leu Thr Ala Ser Glu Ser Gly Phe Leu Asp Ala Ala Gly Ile Glu
            35                  40                  45

CTC GAC GTC CTC AGC GGC CAG CAG GGC ACG GTT CAT TTC ACC TAC GAC     192
Leu Asp Val Leu Ser Gly Gln Gln Gly Thr Val His Phe Thr Tyr Asp
 50                  55                  60

CAG CCT GCC TAC ACC CGT TTT GGG GGT GAG ATC CCG CCA CTG CTC AGC     240
Gln Pro Ala Tyr Thr Arg Phe Gly Gly Glu Ile Pro Pro Leu Leu Ser
 65                  70                  75                  80

GAG GGG TTG CGG GCA CCT GGG CGC ACG CGT CTA CTC GGC ATC ACC CCG     288
Glu Gly Leu Arg Ala Pro Gly Arg Thr Arg Leu Leu Gly Ile Thr Pro
                85                  90                  95

CTC TTG GGG CGC CAG GGC TTC TTT GTC CGC GAC GAC AGC CCG ATC ACA     336
Leu Leu Gly Arg Gln Gly Phe Phe Val Arg Asp Asp Ser Pro Ile Thr
           100                 105                 110

GCG GCC GCC GAC CTT GCC GGA CGT CGA ATC GGC GTC TCG GCC TCG GCA     384
Ala Ala Ala Asp Leu Ala Gly Arg Arg Ile Gly Val Ser Ala Ser Ala
           115                 120                 125

ATT CGC ATC CTG CGC GGC CAG CTG GGC GAC TAC CTC GAG TTG GAT CCC     432
Ile Arg Ile Leu Arg Gly Gln Leu Gly Asp Tyr Leu Glu Leu Asp Pro
           130                 135                 140

TGG CGG CAA ACG CTG GTA GCG CTG GGC TCG TGG GAG GCG CGC GCC TTG     480
Trp Arg Gln Thr Leu Val Ala Leu Gly Ser Trp Glu Ala Arg Ala Leu
145                 150                 155                 160

TTG CAC ACC CTT GAG CAC GGT GAA CTG GGT GTG GAC GAC GTC GAG CTG     528
Leu His Thr Leu Glu His Gly Glu Leu Gly Val Asp Asp Val Glu Leu
```

```
GTG CCG ATC AGC AGT CCT GGT GTC GAT GTT CCC GCT GAG CAG CTC GAA      576
Val Pro Ile Ser Ser Pro Gly Val Asp Val Pro Ala Glu Gln Leu Glu
            180                 185                 190

GAA TCG GCG ACC GTC AAG GGT GCG GAC CTC TTT CCC GAT GTC GCC CGC      624
Glu Ser Ala Thr Val Lys Gly Ala Asp Leu Phe Pro Asp Val Ala Arg
        195                 200                 205

GGT CAG GCC GCG GTG TTG GCC AGC GGA GAC GTT GAC GCC CTG TAC AGT      672
Gly Gln Ala Ala Val Leu Ala Ser Gly Asp Val Asp Ala Leu Tyr Ser
    210                 215                 220

TGG CTG CCC TGG GCC GGG GAG TTG CAA GCC ACC GGG GCC CGC CCA GTG      720
Trp Leu Pro Trp Ala Gly Glu Leu Gln Ala Thr Gly Ala Arg Pro Val
225                 230                 235                 240

GTG GAT CTC GGC CTC GAT GAG CGC AAT GCC TAC GCC AGT GTG TGG ACG      768
Val Asp Leu Gly Leu Asp Glu Arg Asn Ala Tyr Ala Ser Val Trp Thr
                245                 250                 255

GTC AGC AGC GGG CTG GTT CGC CAG CGA CCT GGC CTT GTT CAA CGA CTG      816
Val Ser Ser Gly Leu Val Arg Gln Arg Pro Gly Leu Val Gln Arg Leu
            260                 265                 270

GTC GAC GCG GCC GTC GAC GCC GGG CTG TGG GCA CGC GAT CAT TCC GAC      864
Val Asp Ala Ala Val Asp Ala Gly Leu Trp Ala Arg Asp His Ser Asp
        275                 280                 285

GCG GTG ACC AGC CTG CAC GCC GCG AAC CTG GGC GTA TCG ACC GGA GCA      912
Ala Val Thr Ser Leu His Ala Ala Asn Leu Gly Val Ser Thr Gly Ala
    290                 295                 300

GTA GGC CAG GGC TTC GGC GCC GAC TTC CAG CAG CGT CTG GTT CCA CGC      960
Val Gly Gln Gly Phe Gly Ala Asp Phe Gln Gln Arg Leu Val Pro Arg
305                 310                 315                 320

CTG GAT CAC GAC GCC CTC GCC CTC CTG GAG CGC ACA CAG CAA TTC CTG     1008
Leu Asp His Asp Ala Leu Ala Leu Leu Glu Arg Thr Gln Gln Phe Leu
                325                 330                 335

CTC ACC AAC AAC TTG CTG CAG GAA CCC GTC GCC CTC GAT CAG TGG GCG     1056
Leu Thr Asn Asn Leu Leu Gln Glu Pro Val Ala Leu Asp Gln Trp Ala
            340                 345                 350

GCT CCG GAA TTT CTG AAC AAC AGC CTC AAT CGC CAC CGA                 1095
Ala Pro Glu Phe Leu Asn Asn Ser Leu Asn Arg His Arg
        355                 360                 365
```

(2) INFORMATION FOR SEQ ID NO:4:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Ser Arg Val Asp Pro Ala Asn Pro Gly Ser Glu Leu Asp Ser
1               5                  10                  15

Ala Ile Arg Asp Thr Leu Thr Tyr Ser Asn Cys Pro Val Pro Asn Ala
            20                  25                  30

Leu Leu Thr Ala Ser Glu Ser Gly Phe Leu Asp Ala Ala Gly Ile Glu
        35                  40                  45

Leu Asp Val Leu Ser Gly Gln Gln Gly Thr Val His Phe Thr Tyr Asp
    50                  55                  60

Gln Pro Ala Tyr Thr Arg Phe Gly Gly Glu Ile Pro Pro Leu Leu Ser
65                  70                  75                  80

Glu Gly Leu Arg Ala Pro Gly Arg Thr Arg Leu Leu Gly Ile Thr Pro
                85                  90                  95
```

```
Leu Leu Gly Arg Gln Gly Phe Phe Val Arg Asp Asp Ser Pro Ile Thr
            100                 105                 110

Ala Ala Ala Asp Leu Ala Gly Arg Arg Ile Gly Val Ser Ala Ser Ala
            115                 120                 125

Ile Arg Ile Leu Arg Gly Gln Leu Gly Asp Tyr Leu Glu Leu Asp Pro
            130                 135                 140

Trp Arg Gln Thr Leu Val Ala Leu Gly Ser Trp Glu Ala Arg Ala Leu
145                 150                 155                 160

Leu His Thr Leu Glu His Gly Glu Leu Gly Val Asp Val Glu Leu
            165                 170                 175

Val Pro Ile Ser Ser Pro Gly Val Asp Val Pro Ala Glu Gln Leu Glu
            180                 185                 190

Glu Ser Ala Thr Val Lys Gly Ala Asp Leu Phe Pro Asp Val Ala Arg
            195                 200                 205

Gly Gln Ala Ala Val Leu Ala Ser Gly Asp Val Asp Ala Leu Tyr Ser
            210                 215                 220

Trp Leu Pro Trp Ala Gly Glu Leu Gln Ala Thr Gly Ala Arg Pro Val
225                 230                 235                 240

Val Asp Leu Gly Leu Asp Glu Arg Asn Ala Tyr Ala Ser Val Trp Thr
                245                 250                 255

Val Ser Ser Gly Leu Val Arg Gln Arg Pro Gly Leu Val Gln Arg Leu
            260                 265                 270

Val Asp Ala Ala Val Asp Ala Gly Leu Trp Ala Arg Asp His Ser Asp
            275                 280                 285

Ala Val Thr Ser Leu His Ala Ala Asn Leu Gly Val Ser Thr Gly Ala
            290                 295                 300

Val Gly Gln Gly Phe Gly Ala Asp Phe Gln Gln Arg Leu Val Pro Arg
305                 310                 315                 320

Leu Asp His Asp Ala Leu Ala Leu Leu Glu Arg Thr Gln Gln Phe Leu
                325                 330                 335

Leu Thr Asn Asn Leu Leu Gln Glu Pro Val Ala Leu Asp Gln Trp Ala
            340                 345                 350

Ala Pro Glu Phe Leu Asn Asn Ser Leu Asn Arg His Arg
            355                 360                 365

(2) INFORMATION FOR SEQ ID NO:5:

(i) SEQUENCE CHARACTERISTICS:
        (A) LENGTH: 1251 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1095

(xi) SEQUENCE DESCRIPTION: SEQ ID NO:5:

ATG ACA CTG TCA CCT GAA AAG CAG CAC GTT CGA CCA CGC GAC GCC GCC      48
Met Thr Leu Ser Pro Glu Lys Gln His Val Arg Pro Arg Asp Ala Ala
 1               5                  10                  15

GAC AAC GAT CCC GTC GCG GTT GCC CGT GGG CTA GCC GAA AAG TGG CGA      96
Asp Asn Asp Pro Val Ala Val Ala Arg Gly Leu Ala Glu Lys Trp Arg
                20                  25                  30

GCC ACC GCC GTC GAG CGT GAT CGC GCC GGG GGT TCG GCA ACA GCC GAG     144
Ala Thr Ala Val Glu Arg Asp Arg Ala Gly Gly Ser Ala Thr Ala Glu
            35                  40                  45
```

| | |
|---|---|
| CGC GAA GAC CTG CGC GCG AGC GCG CTG CTG TCG CTC CTC GTC CCG CGC<br>Arg Glu Asp Leu Arg Ala Ser Ala Leu Leu Ser Leu Leu Val Pro Arg<br>50          55              60 | 192 |
| GAA TAC GGC GGC TGG GGC GCA GAC TGG CCC ACC GCC ATC GAG GTC GTC<br>Glu Tyr Gly Gly Trp Gly Ala Asp Trp Pro Thr Ala Ile Glu Val Val<br>65              70              75              80 | 240 |
| CGC GAA ATC GCG GCA GCC GAT GGA TCT TTG GGA CAC CTG TTC GGA TAC<br>Arg Glu Ile Ala Ala Ala Asp Gly Ser Leu Gly His Leu Phe Gly Tyr<br>          85              90              95 | 288 |
| CAC CTC ACC AAC GCC CCG ATG ATC GAA CTG ATC GGC TCG CAG GAA CAA<br>His Leu Thr Asn Ala Pro Met Ile Glu Leu Ile Gly Ser Gln Glu Gln<br>          100             105             110 | 336 |
| GAA GAA CAC CTG TAC ACC CAG ATC GCG CAG AAC AAC TGG TGG ACC GGA<br>Glu Glu His Leu Tyr Thr Gln Ile Ala Gln Asn Asn Trp Trp Thr Gly<br>    115             120             125 | 384 |
| AAT GCC TCC AGC GAG AAC AAC AGC CAC GTG CTG GAC TGG AAG GTC AGC<br>Asn Ala Ser Ser Glu Asn Asn Ser His Val Leu Asp Trp Lys Val Ser<br>130             135             140 | 432 |
| GCC ACC CCG ACC GAA GAC GGC GGC TAC GTG CTC AAT GGC ACG AAG CAC<br>Ala Thr Pro Thr Glu Asp Gly Gly Tyr Val Leu Asn Gly Thr Lys His<br>145             150             155             160 | 480 |
| TTC TGC AGC GGC GCC AAG GGG TCG GAC CTG CTG TTC GTG TTC GGC GTC<br>Phe Cys Ser Gly Ala Lys Gly Ser Asp Leu Leu Phe Val Phe Gly Val<br>          165             170             175 | 528 |
| GTC CAG GAT GAT TCT CCG CAG CAG GGT GCG ATC ATT GCT GCC GCT ATC<br>Val Gln Asp Asp Ser Pro Gln Gln Gly Ala Ile Ile Ala Ala Ala Ile<br>          180             185             190 | 576 |
| CCG ACA TCG CGG GCT GGC GTT ACG CCC AAC GAC GAC TGG GCC GCC ATC<br>Pro Thr Ser Arg Ala Gly Val Thr Pro Asn Asp Asp Trp Ala Ala Ile<br>          195             200             205 | 624 |
| GGC ATG CGG CAG ACC GAC AGC GGT TCC ACG GAC TTC CAC AAC GTC AAG<br>Gly Met Arg Gln Thr Asp Ser Gly Ser Thr Asp Phe His Asn Val Lys<br>210             215             220 | 672 |
| GTC GAG CCT GAC GAA GTG CTG GGC GCG CCC AAC GCC TTC GTT CTC GCC<br>Val Glu Pro Asp Glu Val Leu Gly Ala Pro Asn Ala Phe Val Leu Ala<br>225             230             235             240 | 720 |
| TTC ATA CAA TCC GAG CGC GGC AGC CTC TTC GCG CCC ATA GCG CAA TTG<br>Phe Ile Gln Ser Glu Arg Gly Ser Leu Phe Ala Pro Ile Ala Gln Leu<br>          245             250             255 | 768 |
| ATC TTC GCC AAC GTC TAT CTG GGG ATC GCG CAC GGC GCA CTC GAT GCC<br>Ile Phe Ala Asn Val Tyr Leu Gly Ile Ala His Gly Ala Leu Asp Ala<br>          260             265             270 | 816 |
| GCC AGG GAG TAC ACC CGT ACC CAG GCG AGG CCC TGG ACA CCG GCC GGT<br>Ala Arg Glu Tyr Thr Arg Thr Gln Ala Arg Pro Trp Thr Pro Ala Gly<br>          275             280             285 | 864 |
| ATT CAA CAG GCA ACC GAG GAT CCC TAC ACC ATC CGC TCC TAC GGT GAG<br>Ile Gln Gln Ala Thr Glu Asp Pro Tyr Thr Ile Arg Ser Tyr Gly Glu<br>290             295             300 | 912 |
| TTC ACC ATC GCA TTG CAG GGA GCT GAC GCC GCC GCC CGT GAA GCG GCC<br>Phe Thr Ile Ala Leu Gln Gly Ala Asp Ala Ala Ala Arg Glu Ala Ala<br>305             310             315             320 | 960 |
| CAC CTG CTG CAG ACG GTG TGG GAC AAG GGC GAC GCG CTC ACC CCC GAG<br>His Leu Leu Gln Thr Val Trp Asp Lys Gly Asp Ala Leu Thr Pro Glu<br>          325             330             335 | 1008 |
| GAC CGC GGC GAA CTG ATG GTG AAG GTC TCG GGA GTC AAA GCG TTG GCC<br>Asp Arg Gly Glu Leu Met Val Lys Val Ser Gly Val Lys Ala Leu Ala<br>          340             345             350 | 1056 |
| ACC AAC GCC GCC CTC AAC ATC AGC AGC GGC GTC TTC GAG GTGATCGGCG<br>Thr Asn Ala Ala Leu Asn Ile Ser Ser Gly Val Phe Glu<br>          355             360             365 | 1105 |

```
CGCGCGGAAC ACATCCCAGG TACGGTTTCG ACCGCTTCTG GCGCAACGTG CGCACCCACT    1165

CCCTGCACGA CCCGGTGTCC TACAAGATCG CCGACGTCGG CAAGCACACC TTGAACGGTC    1225

AATACCCGAT TCCCGGCTTC ACCTCC                                         1251
```

(2) INFORMATION FOR SEQ ID NO:6:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Leu Ser Pro Glu Lys Gln His Val Arg Pro Arg Asp Ala Ala
 1               5                  10                  15

Asp Asn Asp Pro Val Ala Val Ala Arg Gly Leu Ala Glu Lys Trp Arg
                20                  25                  30

Ala Thr Ala Val Glu Arg Asp Arg Ala Gly Ser Ala Thr Ala Glu
            35                  40                  45

Arg Glu Asp Leu Arg Ala Ser Ala Leu Leu Ser Leu Val Pro Arg
    50                  55                  60

Glu Tyr Gly Gly Trp Gly Ala Asp Trp Pro Thr Ala Ile Glu Val Val
65                  70                  75                  80

Arg Glu Ile Ala Ala Ala Asp Gly Ser Leu Gly His Leu Phe Gly Tyr
                85                  90                  95

His Leu Thr Asn Ala Pro Met Ile Glu Leu Ile Gly Ser Gln Glu Gln
            100                 105                 110

Glu Glu His Leu Tyr Thr Gln Ile Ala Gln Asn Asn Trp Trp Thr Gly
        115                 120                 125

Asn Ala Ser Ser Glu Asn Asn Ser His Val Leu Asp Trp Lys Val Ser
130                 135                 140

Ala Thr Pro Thr Glu Asp Gly Gly Tyr Val Leu Asn Gly Thr Lys His
145                 150                 155                 160

Phe Cys Ser Gly Ala Lys Gly Ser Asp Leu Leu Phe Val Phe Gly Val
                165                 170                 175

Val Gln Asp Asp Ser Pro Gln Gln Gly Ala Ile Ile Ala Ala Ala Ile
            180                 185                 190

Pro Thr Ser Arg Ala Gly Val Thr Pro Asn Asp Asp Trp Ala Ala Ile
        195                 200                 205

Gly Met Arg Gln Thr Asp Ser Gly Ser Thr Asp Phe His Asn Val Lys
210                 215                 220

Val Glu Pro Asp Glu Val Leu Gly Ala Pro Asn Ala Phe Val Leu Ala
225                 230                 235                 240

Phe Ile Gln Ser Glu Arg Gly Ser Leu Phe Ala Pro Ile Ala Gln Leu
                245                 250                 255

Ile Phe Ala Asn Val Tyr Leu Gly Ile Ala His Gly Ala Leu Asp Ala
            260                 265                 270

Ala Arg Glu Tyr Thr Arg Thr Gln Ala Arg Pro Trp Thr Pro Ala Gly
        275                 280                 285

Ile Gln Gln Ala Thr Glu Asp Pro Tyr Thr Ile Arg Ser Tyr Gly Glu
    290                 295                 300

Phe Thr Ile Ala Leu Gln Gly Ala Asp Ala Ala Arg Glu Ala Ala
305                 310                 315                 320

His Leu Leu Gln Thr Val Trp Asp Lys Gly Asp Ala Leu Thr Pro Glu
                325                 330                 335
```

```
                Asp Arg Gly Glu Leu Met Val Lys Val Ser Gly Val Lys Ala Leu Ala
                            340                 345                 350

Thr Asn Ala Ala Leu Asn Ile Ser Ser Gly Val Phe Glu
                            355                 360             365

(2) INFORMATION FOR SEQ ID NO:7:

(i) SEQUENCE CHARACTERISTICS:
          (A) LENGTH: 1362 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: CDS
          (B) LOCATION: 1..1359

(xi) SEQUENCE DESCRIPTION: SEQ ID NO:7:

ATG ACC GAT CCA CGT CAG CTG CAC CTG GCC GGA TTC TTC TGT GCC GGC       48
Met Thr Asp Pro Arg Gln Leu His Leu Ala Gly Phe Phe Cys Ala Gly
 1               5                  10                  15

AAC GTC ACG CAC GCC CAC GGA GCG TGG CGC CAC GCC GAC GAC TCC AAC       96
Asn Val Thr His Ala His Gly Ala Trp Arg His Ala Asp Asp Ser Asn
             20                  25                  30

GGC TTC CTC ACC AAG GAG TAC TAC CAG CAG ATT GCC CGC ACG CTC GAG      144
Gly Phe Leu Thr Lys Glu Tyr Tyr Gln Gln Ile Ala Arg Thr Leu Glu
         35                  40                  45

CGC GGC AAG TTC GAC CTG CTG TTC CTT CCC GAC GCG CTC GCC GTG TGG      192
Arg Gly Lys Phe Asp Leu Leu Phe Leu Pro Asp Ala Leu Ala Val Trp
     50                  55                  60

GAC AGC TAC GGC GAC AAT CTG GAG ACC GGT CTG CGG TAT GGC GGG CAA      240
Asp Ser Tyr Gly Asp Asn Leu Glu Thr Gly Leu Arg Tyr Gly Gly Gln
 65                  70                  75                  80

GGC GCG GTG ATG CTG GAG CCC GGC GTA GTT ATC GCC GCG ATG GCC TCG      288
Gly Ala Val Met Leu Glu Pro Gly Val Val Ile Ala Ala Met Ala Ser
                 85                  90                  95

GTG ACC GAA CAT CTG GGG CTG GGC GCC ACC ATT TCC ACC ACC TAC TAC      336
Val Thr Glu His Leu Gly Leu Gly Ala Thr Ile Ser Thr Thr Tyr Tyr
            100                 105                 110

CCG CCC TAC CAT GTA GCC CGG GTC GTC GCT TCG CTG GAC CAG CTG TCC      384
Pro Pro Tyr His Val Ala Arg Val Val Ala Ser Leu Asp Gln Leu Ser
        115                 120                 125

TCC GGG CGA GTG TCG TGG AAC GTG GTC ACC TCG CTC AGC AAT GCA GAG      432
Ser Gly Arg Val Ser Trp Asn Val Val Thr Ser Leu Ser Asn Ala Glu
    130                 135                 140

GCG CGC AAC TTC GGC TTC GAT GAA CAT CTC GAC CAC GAT GCC CGC TAC      480
Ala Arg Asn Phe Gly Phe Asp Glu His Leu Asp His Asp Ala Arg Tyr
145                 150                 155                 160

GAT CGC GCC GAT GAA TTC CTC GAG GTC GTG CGC AAG CTC TGG AAC AGC      528
Asp Arg Ala Asp Glu Phe Leu Glu Val Val Arg Lys Leu Trp Asn Ser
                165                 170                 175

TGG GAT CGC GAT GCG CTG ACA CTC GAC AAG GCA ACC GGC CAG TTC GCC      576
Trp Asp Arg Asp Ala Leu Thr Leu Asp Lys Ala Thr Gly Gln Phe Ala
            180                 185                 190

GAT CCG GCT AAG GTG CGC TAC ATC GAC CAC CGC GGC GAA TGG CTC AAC      624
Asp Pro Ala Lys Val Arg Tyr Ile Asp His Arg Gly Glu Trp Leu Asn
        195                 200                 205

GTA CGC GGG CCG CTT CAG GTG CCG CGC TCC CCC CAG GGC GAG CCT GTC      672
Val Arg Gly Pro Leu Gln Val Pro Arg Ser Pro Gln Gly Glu Pro Val
    210                 215                 220
```

|  |  |  |  |  |  |  |  |  |  |  |  |  |  |  |  |
|---|---|---|---|---|---|---|---|---|---|---|---|---|---|---|---|
| ATT | CTG | CAG | GCC | GGG | CTT | TCG | GCG | CGG | GGC | AAG | CGC | TTC | GCC | GGG | CGC | 720 |
| Ile | Leu | Gln | Ala | Gly | Leu | Ser | Ala | Arg | Gly | Lys | Arg | Phe | Ala | Gly | Arg |
| 225 |  |  |  |  | 230 |  |  |  |  | 235 |  |  |  |  | 240 |
| TGG | GCG | GAC | GCG | GTG | TTC | ACG | ATT | TCG | CCC | AAT | CTG | GAC | ATC | ATG | CAG | 768 |
| Trp | Ala | Asp | Ala | Val | Phe | Thr | Ile | Ser | Pro | Asn | Leu | Asp | Ile | Met | Gln |
|  |  |  |  | 245 |  |  |  |  | 250 |  |  |  |  | 255 |  |
| GCC | ACG | TAC | CGC | GAC | ATA | AAG | GCG | CAG | GTC | GAG | GCC | GCC | GGA | CGC | GAT | 816 |
| Ala | Thr | Tyr | Arg | Asp | Ile | Lys | Ala | Gln | Val | Glu | Ala | Ala | Gly | Arg | Asp |
|  |  |  | 260 |  |  |  |  | 265 |  |  |  |  | 270 |  |  |
| CCC | GAG | CAG | GTC | AAG | GTG | TTT | GCC | GCG | GTG | ATG | CCG | ATC | CTC | GGC | GAG | 864 |
| Pro | Glu | Gln | Val | Lys | Val | Phe | Ala | Ala | Val | Met | Pro | Ile | Leu | Gly | Glu |
|  |  | 275 |  |  |  |  | 280 |  |  |  |  | 285 |  |  |  |
| ACC | GAG | GCG | ATC | GCC | AGG | CAG | CGT | CTC | GAA | TAC | ATA | AAT | TCG | CTG | GTG | 912 |
| Thr | Glu | Ala | Ile | Ala | Arg | Gln | Arg | Leu | Glu | Tyr | Ile | Asn | Ser | Leu | Val |
| 290 |  |  |  |  | 295 |  |  |  |  | 300 |  |  |  |  |  |
| CAT | CCC | GAA | GTC | GGG | CTT | TCT | ACG | TTG | TCC | AGC | CAT | GTC | GGG | GTC | AAC | 960 |
| His | Pro | Glu | Val | Gly | Leu | Ser | Thr | Leu | Ser | Ser | His | Val | Gly | Val | Asn |
| 305 |  |  |  |  | 310 |  |  |  |  | 315 |  |  |  |  | 320 |
| CTT | GCC | GAC | TAT | TCG | CTC | GAT | ACC | CCG | CTG | ACC | GAG | GTC | CTG | GGC | GAT | 1008 |
| Leu | Ala | Asp | Tyr | Ser | Leu | Asp | Thr | Pro | Leu | Thr | Glu | Val | Leu | Gly | Asp |
|  |  |  |  | 325 |  |  |  |  | 330 |  |  |  |  | 335 |  |
| CTC | GCC | CAG | CGC | AAC | GTG | CCC | ACC | CAA | CTG | GGC | ATG | TTC | GCC | AGG | ATG | 1056 |
| Leu | Ala | Gln | Arg | Asn | Val | Pro | Thr | Gln | Leu | Gly | Met | Phe | Ala | Arg | Met |
|  |  |  | 340 |  |  |  |  | 345 |  |  |  |  | 350 |  |  |
| TTG | CAG | GCC | GAG | ACG | CTG | ACC | GTG | GGA | GAA | ATG | GGC | CGG | CGT | TAT | GGC | 1104 |
| Leu | Gln | Ala | Glu | Thr | Leu | Thr | Val | Gly | Glu | Met | Gly | Arg | Arg | Tyr | Gly |
|  |  | 355 |  |  |  |  | 360 |  |  |  |  | 365 |  |  |  |
| GCC | AAC | GTG | GGC | TTC | GTC | CCG | CAG | TGG | GCG | GGA | ACC | CGC | GAG | CAG | ATC | 1152 |
| Ala | Asn | Val | Gly | Phe | Val | Pro | Gln | Trp | Ala | Gly | Thr | Arg | Glu | Gln | Ile |
|  | 370 |  |  |  |  | 375 |  |  |  |  | 380 |  |  |  |  |
| GCG | GAC | CTG | ATC | GAG | ATC | CAT | TTC | AAG | GCC | GGC | GGC | GCC | GAT | GGC | TTC | 1200 |
| Ala | Asp | Leu | Ile | Glu | Ile | His | Phe | Lys | Ala | Gly | Gly | Ala | Asp | Gly | Phe |
| 385 |  |  |  |  | 390 |  |  |  |  | 395 |  |  |  |  | 400 |
| ATC | ATC | TCG | CCG | GCG | TTC | CTG | CCC | GGA | TCT | TAC | GAG | GAA | TTC | GTC | GAT | 1248 |
| Ile | Ile | Ser | Pro | Ala | Phe | Leu | Pro | Gly | Ser | Tyr | Glu | Glu | Phe | Val | Asp |
|  |  |  |  | 405 |  |  |  |  | 410 |  |  |  |  | 415 |  |
| CAG | GTG | GTG | CCC | ATC | CTG | CAG | CAC | CGC | GGA | CTG | TTC | CGC | ACT | GAT | TAC | 1296 |
| Gln | Val | Val | Pro | Ile | Leu | Gln | His | Arg | Gly | Leu | Phe | Arg | Thr | Asp | Tyr |
|  |  |  | 420 |  |  |  |  | 425 |  |  |  |  | 430 |  |  |
| GAA | GGC | CGC | ACC | CTG | CGC | AGC | CAT | CTG | GGA | CTG | CGT | GAA | CCC | GCA | TAC | 1344 |
| Glu | Gly | Arg | Thr | Leu | Arg | Ser | His | Leu | Gly | Leu | Arg | Glu | Pro | Ala | Tyr |
|  |  | 435 |  |  |  |  | 440 |  |  |  |  | 445 |  |  |  |
| CTG | GGA | GAG | TAC | GCA | TGA |  |  |  |  |  |  |  |  |  |  | 1362 |
| Leu | Gly | Glu | Tyr | Ala |  |  |  |  |  |  |  |  |  |  |  |
|  | 450 |  |  |  |  |  |  |  |  |  |  |  |  |  |  |

(2) INFORMATION FOR SEQ ID NO:8:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:8:

|  |  |  |  |  |  |  |  |  |  |  |  |  |  |  |
|---|---|---|---|---|---|---|---|---|---|---|---|---|---|---|
| Met | Thr | Asp | Pro | Arg | Gln | Leu | His | Leu | Ala | Gly | Phe | Phe | Cys | Ala | Gly |
| 1 |  |  |  | 5 |  |  |  |  | 10 |  |  |  |  | 15 |  |

| Asn | Val | Thr | His | Ala | His | Gly | Ala | Trp | Arg | His | Ala | Asp | Asp | Ser | Asn |
|---|---|---|---|---|---|---|---|---|---|---|---|---|---|---|---|
|  |  |  | 20 |  |  |  |  | 25 |  |  |  |  | 30 |  |  |

| Gly | Phe | Leu | Thr | Lys | Glu | Tyr | Tyr | Gln | Gln | Ile | Ala | Arg | Thr | Leu | Glu |
|---|---|---|---|---|---|---|---|---|---|---|---|---|---|---|---|
|  |  | 35 |  |  |  |  | 40 |  |  |  |  | 45 |  |  |  |

-continued

Arg Gly Lys Phe Asp Leu Leu Phe Leu Pro Asp Ala Leu Ala Val Trp
 50                  55                  60

Asp Ser Tyr Gly Asp Asn Leu Glu Thr Gly Leu Arg Tyr Gly Gly Gln
 65                  70                  75                  80

Gly Ala Val Met Leu Glu Pro Gly Val Val Ile Ala Ala Met Ala Ser
                 85                  90                  95

Val Thr Glu His Leu Gly Leu Gly Ala Thr Ile Ser Thr Thr Tyr Tyr
                100                 105                 110

Pro Pro Tyr His Val Ala Arg Val Val Ala Ser Leu Asp Gln Leu Ser
                115                 120                 125

Ser Gly Arg Val Ser Trp Asn Val Val Thr Ser Leu Ser Asn Ala Glu
    130                 135                 140

Ala Arg Asn Phe Gly Phe Asp Glu His Leu Asp His Asp Ala Arg Tyr
145                 150                 155                 160

Asp Arg Ala Asp Glu Phe Leu Glu Val Val Arg Lys Leu Trp Asn Ser
                165                 170                 175

Trp Asp Arg Asp Ala Leu Thr Leu Asp Lys Ala Thr Gly Gln Phe Ala
                180                 185                 190

Asp Pro Ala Lys Val Arg Tyr Ile Asp His Arg Gly Glu Trp Leu Asn
                195                 200                 205

Val Arg Gly Pro Leu Gln Val Pro Arg Ser Pro Gln Gly Glu Pro Val
    210                 215                 220

Ile Leu Gln Ala Gly Leu Ser Ala Arg Gly Lys Arg Phe Ala Gly Arg
225                 230                 235                 240

Trp Ala Asp Ala Val Phe Thr Ile Ser Pro Asn Leu Asp Ile Met Gln
                245                 250                 255

Ala Thr Tyr Arg Asp Ile Lys Ala Gln Val Glu Ala Ala Gly Arg Asp
                260                 265                 270

Pro Glu Gln Val Lys Val Phe Ala Ala Val Met Pro Ile Leu Gly Glu
                275                 280                 285

Thr Glu Ala Ile Ala Arg Gln Arg Leu Glu Tyr Ile Asn Ser Leu Val
    290                 295                 300

His Pro Glu Val Gly Leu Ser Thr Leu Ser Ser His Val Gly Val Asn
305                 310                 315                 320

Leu Ala Asp Tyr Ser Leu Asp Thr Pro Leu Thr Glu Val Leu Gly Asp
                325                 330                 335

Leu Ala Gln Arg Asn Val Pro Thr Gln Leu Gly Met Phe Ala Arg Met
                340                 345                 350

Leu Gln Ala Glu Thr Leu Thr Val Gly Glu Met Gly Arg Arg Tyr Gly
                355                 360                 365

Ala Asn Val Gly Phe Val Pro Gln Trp Ala Gly Thr Arg Glu Gln Ile
    370                 375                 380

Ala Asp Leu Ile Glu Ile His Phe Lys Ala Gly Gly Ala Asp Gly Phe
385                 390                 395                 400

Ile Ile Ser Pro Ala Phe Leu Pro Gly Ser Tyr Glu Glu Phe Val Asp
                405                 410                 415

Gln Val Val Pro Ile Leu Gln His Arg Gly Leu Phe Arg Thr Asp Tyr
                420                 425                 430

Glu Gly Arg Thr Leu Arg Ser His Leu Gly Leu Arg Glu Pro Ala Tyr
    435                 440                 445

Leu Gly Glu Tyr Ala
    450

(2) INFORMATION FOR SEQ ID NO:9:

(i) SEQUENCE CHARACTERISTICS:
        (A) LENGTH: 1110 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1107

(xi) SEQUENCE DESCRIPTION: SEQ ID NO:9:

```
ATG ACG ACA GAC ATC CAC CCG GCG AGC GCC GCA TCG TCG CCG GCG GCG        48
Met Thr Thr Asp Ile His Pro Ala Ser Ala Ala Ser Ser Pro Ala Ala
 1               5                  10                  15

CGC GCG ACG ATC ACC TAC AGC AAC TGC CCC GTG CCT AAT GCC CTG CTC        96
Arg Ala Thr Ile Thr Tyr Ser Asn Cys Pro Val Pro Asn Ala Leu Leu
             20                  25                  30

GCC GCG CTC GGC TCA GGT ATT CTG GAC AGT GCC GGG ATC ACA CTT GCC       144
Ala Ala Leu Gly Ser Gly Ile Leu Asp Ser Ala Gly Ile Thr Leu Ala
         35                  40                  45

CTG CTG ACC GGA AAG CAG GGC GAG GTG CAC TTC ACC TAC GAC CGA GAT       192
Leu Leu Thr Gly Lys Gln Gly Glu Val His Phe Thr Tyr Asp Arg Asp
     50                  55                  60

GAC TAC ACC CGC TTC GGC GGC GAG ATT CCG CCG CTG GTC AGC GAG GGA       240
Asp Tyr Thr Arg Phe Gly Gly Glu Ile Pro Pro Leu Val Ser Glu Gly
 65                  70                  75                  80

CTG CGT GCG CCG GGG CGG ACC CGC CTG CTG GGA CTG ACG CCG GTG CTG       288
Leu Arg Ala Pro Gly Arg Thr Arg Leu Leu Gly Leu Thr Pro Val Leu
                 85                  90                  95

GGC CGC TGG GGC TAC TTC GTC CGG GGC GAC AGC GCG ATC CGC ACC CCG       336
Gly Arg Trp Gly Tyr Phe Val Arg Gly Asp Ser Ala Ile Arg Thr Pro
            100                 105                 110

GCC GAT CTT GCC GGC CGC CGC GTC GGA GTA TCC GAT TCG GCC AGG AGG       384
Ala Asp Leu Ala Gly Arg Arg Val Gly Val Ser Asp Ser Ala Arg Arg
        115                 120                 125

ATA TTG ACC GGA AGG CTG GGC GAC TAC CGC GAA CTT GAT CCC TGG CGG       432
Ile Leu Thr Gly Arg Leu Gly Asp Tyr Arg Glu Leu Asp Pro Trp Arg
    130                 135                 140

CAG ACC CTG GTC GCG CTG GGG ACA TGG GAG GCG CGT GCC TTG CTG AGC       480
Gln Thr Leu Val Ala Leu Gly Thr Trp Glu Ala Arg Ala Leu Leu Ser
145                 150                 155                 160

ACG CTC GAG ACG GCG GGG CTT GGC GTC GGC GAC GTC GAG CTG ACG CGC       528
Thr Leu Glu Thr Ala Gly Leu Gly Val Gly Asp Val Glu Leu Thr Arg
                165                 170                 175

ATC GAG AAC CCG TTC GTC GAC GTG CCG ACC GAA CGA CTG CAT GCC GCC       576
Ile Glu Asn Pro Phe Val Asp Val Pro Thr Glu Arg Leu His Ala Ala
            180                 185                 190

GGC TCG CTC AAA GGA ACC GAC CTG TTC CCC GAC GTG ACC AGC CAG CAG       624
Gly Ser Leu Lys Gly Thr Asp Leu Phe Pro Asp Val Thr Ser Gln Gln
        195                 200                 205

GCC GCA GTC CTT GAG GAT GAG CGC GCC GAC GCC CTG TTC GCG TGG CTT       672
Ala Ala Val Leu Glu Asp Glu Arg Ala Asp Ala Leu Phe Ala Trp Leu
    210                 215                 220

CCC TGG GCG GCC GAG CTC GAG ACC CGC ATC GGT GCA CGG CCG GTC CTA       720
Pro Trp Ala Ala Glu Leu Glu Thr Arg Ile Gly Ala Arg Pro Val Leu
225                 230                 235                 240

GAC CTC AGC GCA GAC GAC CGC AAT GCC TAT GCG AGC ACC TGG ACG GTG       768
Asp Leu Ser Ala Asp Asp Arg Asn Ala Tyr Ala Ser Thr Trp Thr Val
                245                 250                 255
```

```
AGC GCC GAG CTG GTG GAC CGG CAG CCC GAA CTG GTG CAG CGG CTC GTC      816
Ser Ala Glu Leu Val Asp Arg Gln Pro Glu Leu Val Gln Arg Leu Val
        260                 265                 270

GAT GCC GTG GTG GAT GCA GGG CGG TGG GCC GAG GCC AAT GGC GAT GTC      864
Asp Ala Val Val Asp Ala Gly Arg Trp Ala Glu Ala Asn Gly Asp Val
            275                 280                 285

GTC TCC CGC CTG CAC GCC GAT AAC CTC GGT GTC AGT CCC GAA AGC GTC      912
Val Ser Arg Leu His Ala Asp Asn Leu Gly Val Ser Pro Glu Ser Val
        290                 295                 300

CGC CAG GGA TTC GGA GCC GAT TTT CAC CGC CGC CTG ACG CCG CGG CTC      960
Arg Gln Gly Phe Gly Ala Asp Phe His Arg Arg Leu Thr Pro Arg Leu
305                 310                 315                 320

GAC AGC GAT GCT ATC GCC ATC CTG GAG CGT ACT CAG CGG TTC CTG AAG     1008
Asp Ser Asp Ala Ile Ala Ile Leu Glu Arg Thr Gln Arg Phe Leu Lys
                325                 330                 335

GAT GCG AAC CTG ATC GAT CGG TCG TTG GCG CTC GAT CGG TGG GCT GCA     1056
Asp Ala Asn Leu Ile Asp Arg Ser Leu Ala Leu Asp Arg Trp Ala Ala
            340                 345                 350

CCT GAA TTC CTC GAA CAA AGT CTC TCA CGC CAG GTC GAA GGG CAG ATA     1104
Pro Glu Phe Leu Glu Gln Ser Leu Ser Arg Gln Val Glu Gly Gln Ile
        355                 360                 365

GCA TGA                                                              1110
Ala (2) INFORMATION FOR SEQ ID NO:10:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:10:

Met Thr Thr Asp Ile His Pro Ala Ser Ala Ser Ser Pro Ala Ala
 1               5                  10                  15

Arg Ala Thr Ile Thr Tyr Ser Asn Cys Pro Val Pro Asn Ala Leu Leu
                20                  25                  30

Ala Ala Leu Gly Ser Gly Ile Leu Asp Ser Ala Gly Ile Thr Leu Ala
            35                  40                  45

Leu Leu Thr Gly Lys Gln Gly Glu Val His Phe Thr Tyr Asp Arg Asp
    50                  55                  60

Asp Tyr Thr Arg Phe Gly Gly Glu Ile Pro Pro Leu Val Ser Glu Gly
65                  70                  75                  80

Leu Arg Ala Pro Gly Arg Thr Arg Leu Leu Gly Leu Thr Pro Val Leu
                85                  90                  95

Gly Arg Trp Gly Tyr Phe Val Arg Gly Asp Ser Ala Ile Arg Thr Pro
                100                 105                 110

Ala Asp Leu Ala Gly Arg Val Gly Val Ser Asp Ser Ala Arg Arg
            115                 120                 125

Ile Leu Thr Gly Arg Leu Gly Asp Tyr Arg Glu Leu Asp Pro Trp Arg
    130                 135                 140

Gln Thr Leu Val Ala Leu Gly Thr Trp Glu Ala Arg Ala Leu Leu Ser
145                 150                 155                 160

Thr Leu Glu Thr Ala Gly Leu Gly Val Gly Asp Val Glu Leu Thr Arg
                165                 170                 175

Ile Glu Asn Pro Phe Val Asp Val Pro Thr Glu Arg Leu His Ala Ala
                180                 185                 190

Gly Ser Leu Lys Gly Thr Asp Leu Phe Pro Asp Val Thr Ser Gln Gln
```

```
                195                 200                 205
Ala  Ala  Val  Leu  Glu  Asp  Glu  Arg  Ala  Asp  Ala  Leu  Phe  Ala  Trp  Leu
          210                 215                 220

Pro  Trp  Ala  Ala  Glu  Leu  Glu  Thr  Arg  Ile  Gly  Ala  Arg  Pro  Val  Leu
225                 230                 235                 240

Asp  Leu  Ser  Ala  Asp  Asp  Arg  Asn  Ala  Tyr  Ala  Ser  Thr  Trp  Thr  Val
                    245                 250                 255

Ser  Ala  Glu  Leu  Val  Asp  Arg  Gln  Pro  Glu  Leu  Val  Gln  Arg  Leu  Val
               260                 265                 270

Asp  Ala  Val  Val  Asp  Ala  Gly  Arg  Trp  Ala  Glu  Ala  Asn  Gly  Asp  Val
          275                 280                 285

Val  Ser  Arg  Leu  His  Ala  Asp  Asn  Leu  Gly  Val  Ser  Pro  Glu  Ser  Val
290                 295                 300

Arg  Gln  Gly  Phe  Gly  Ala  Asp  Phe  His  Arg  Arg  Leu  Thr  Pro  Arg  Leu
305                 310                 315                 320

Asp  Ser  Asp  Ala  Ile  Ala  Ile  Leu  Glu  Arg  Thr  Gln  Arg  Phe  Leu  Lys
                    325                 330                 335

Asp  Ala  Asn  Leu  Ile  Asp  Arg  Ser  Leu  Ala  Leu  Asp  Arg  Trp  Ala  Ala
               340                 345                 350

Pro  Glu  Phe  Leu  Glu  Gln  Ser  Leu  Ser  Arg  Gln  Val  Glu  Gly  Gln  Ile
          355                 360                 365

Ala
```

(2) INFORMATION FOR SEQ ID NO:11:

(i) SEQUENCE CHARACTERISTICS:
        (A) LENGTH: 1236 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1236

(xi) SEQUENCE DESCRIPTION: SEQ ID NO:11:

```
ATG  AAC  GAA  CTC  GTC  AAA  GAT  CTC  GGC  CTC  AAT  CGA  TCC  GAT  CCG  ATC      48
Met  Asn  Glu  Leu  Val  Lys  Asp  Leu  Gly  Leu  Asn  Arg  Ser  Asp  Pro  Ile
1                   5                   10                  15

GGC  GCT  GTG  CGG  CGA  CTG  GCC  GCG  CAG  TGG  GGG  GCC  ACC  GCT  GTT  GAT      96
Gly  Ala  Val  Arg  Arg  Leu  Ala  Ala  Gln  Trp  Gly  Ala  Thr  Ala  Val  Asp
               20                  25                  30

CGG  GAC  CGG  GCC  GGC  GGA  TCG  GCA  ACC  GCC  GAA  CTC  GAT  CAA  CTG  CGC     144
Arg  Asp  Arg  Ala  Gly  Gly  Ser  Ala  Thr  Ala  Glu  Leu  Asp  Gln  Leu  Arg
          35                  40                  45

GGC  AGC  GGC  CTG  CTC  TCG  CTG  TCC  ATT  CCC  GCC  GCA  TAT  GGC  GGC  TGG     192
Gly  Ser  Gly  Leu  Leu  Ser  Leu  Ser  Ile  Pro  Ala  Ala  Tyr  Gly  Gly  Trp
     50                  55                  60

GGC  GCC  GAC  TGG  CCA  ACG  ACT  CTG  GAA  GTT  ATC  CGC  GAA  GTC  GCA  ACG     240
Gly  Ala  Asp  Trp  Pro  Thr  Thr  Leu  Glu  Val  Ile  Arg  Glu  Val  Ala  Thr
65                  70                  75                  80

GTG  GAC  GGA  TCG  CTG  GCG  CAT  CTA  TTC  GGC  TAC  CAC  CTC  GGC  TGC  GTA     288
Val  Asp  Gly  Ser  Leu  Ala  His  Leu  Phe  Gly  Tyr  His  Leu  Gly  Cys  Val
                    85                  90                  95

CCG  ATG  ATC  GAG  CTG  TTC  GGC  TCG  GCG  CCA  CAA  AAG  GAA  CGG  CTG  TAC     336
Pro  Met  Ile  Glu  Leu  Phe  Gly  Ser  Ala  Pro  Gln  Lys  Glu  Arg  Leu  Tyr
               100                 105                 110

CGC  CAG  ATC  GCA  AGC  CAT  GAT  TGG  CGG  GTC  GGG  AAT  GCG  TCG  AGC  GAA     384
```

```
                Arg Gln Ile Ala Ser His Asp Trp Arg Val Gly Asn Ala Ser Ser Glu
                                115                 120                 125

AAC AAC AGC CAC GTG CTC GAG TGG AAG CTT GCC GCC ACC GCC GTC GAT              432
Asn Asn Ser His Val Leu Glu Trp Lys Leu Ala Ala Thr Ala Val Asp
        130                 135                 140

GAT GGC GGG TTC GTC CTC AAC GGC GCG AAG CAC TTC TGC AGC GGC GCC              480
Asp Gly Gly Phe Val Leu Asn Gly Ala Lys His Phe Cys Ser Gly Ala
145                 150                 155                 160

AAA AGC TCC GAC CTG CTC ATC GTG TTC GGC GTG ATC CAG GAC GAA TCC              528
Lys Ser Ser Asp Leu Leu Ile Val Phe Gly Val Ile Gln Asp Glu Ser
                165                 170                 175

CCC CTG CGC GGC GCG ATC ATC ACC GCG GTC ATT CCC ACC GAC CGG GCC              576
Pro Leu Arg Gly Ala Ile Ile Thr Ala Val Ile Pro Thr Asp Arg Ala
        180                 185                 190

GGT GTT CAG ATC AAT GAC GAC TGG CGC GCA ATC GGG ATG CGC CAG ACC              624
Gly Val Gln Ile Asn Asp Asp Trp Arg Ala Ile Gly Met Arg Gln Thr
                195                 200                 205

GAC AGC GGC AGC GCC GAA TTT CGC GAC GTC CGA GTC TAC CCA GAC GAG              672
Asp Ser Gly Ser Ala Glu Phe Arg Asp Val Arg Val Tyr Pro Asp Glu
210                 215                 220

ATC TTG GGG GCA CCA AAC TCA GTC GTT GAG GCG TTC GTG ACA AGC AAC              720
Ile Leu Gly Ala Pro Asn Ser Val Val Glu Ala Phe Val Thr Ser Asn
225                 230                 235                 240

CGC GGC AGC CTG TGG ACG CCG GCG ATT CAG TCG ATC TTC TCG AAC GTT              768
Arg Gly Ser Leu Trp Thr Pro Ala Ile Gln Ser Ile Phe Ser Asn Val
                245                 250                 255

TAT CTG GGG CTC GCG CGT GGC GCG CTC GAG GCG GCA GCG GAT TAC ACC              816
Tyr Leu Gly Leu Ala Arg Gly Ala Leu Glu Ala Ala Ala Asp Tyr Thr
                260                 265                 270

CGG ACC CAG AGC CGC CCC TGG ACA CCC GCC GGC GTG GCG AAG GCG ACA              864
Arg Thr Gln Ser Arg Pro Trp Thr Pro Ala Gly Val Ala Lys Ala Thr
                275                 280                 285

GAG GAT CCC CAC ATC ATC GCC ACC TAC GGT GAA CTG GCG ATC GCG CTC              912
Glu Asp Pro His Ile Ile Ala Thr Tyr Gly Glu Leu Ala Ile Ala Leu
        290                 295                 300

CAG GGC GCC GAG GCG GCC GCG CGC GAG GTC GCG GCC CTG TTG CAA CAG              960
Gln Gly Ala Glu Ala Ala Ala Arg Glu Val Ala Ala Leu Leu Gln Gln
305                 310                 315                 320

GCG TGG GAC AAG GGC GAT GCG GTG ACG CCC GAA GAG CGC GGC CAG CTG             1008
Ala Trp Asp Lys Gly Asp Ala Val Thr Pro Glu Glu Arg Gly Gln Leu
                325                 330                 335

ATG GTG AAG GTT TCG GGT GTG AAG GCC CTC TCG ACG AAG GCC GCC CTC             1056
Met Val Lys Val Ser Gly Val Lys Ala Leu Ser Thr Lys Ala Ala Leu
                340                 345                 350

GAC ATC ACC AGC CGT ATT TTC GAG ACA ACG GGC TCG CGA TCG ACG CAT             1104
Asp Ile Thr Ser Arg Ile Phe Glu Thr Thr Gly Ser Arg Ser Thr His
        355                 360                 365

CCC AGA TAC GGA TTC GAT CGG TTC TGG CGT AAC ATC CGG ACT CAT ACG             1152
Pro Arg Tyr Gly Phe Asp Arg Phe Trp Arg Asn Ile Arg Thr His Thr
        370                 375                 380

CTG CAC GAT CCG GTA TCG TAT AAA ATC GTC GAT GTG GGG AAC TAC ACG             1200
Leu His Asp Pro Val Ser Tyr Lys Ile Val Asp Val Gly Asn Tyr Thr
385                 390                 395                 400

CTC AAC GGG ACA TTC CCG GTT CCC GGA TTT ACG TCA                             1236
Leu Asn Gly Thr Phe Pro Val Pro Gly Phe Thr Ser
                405                 410
```

(2) INFORMATION FOR SEQ ID NO:12:

(i) SEQUENCE CHARACTERISTICS:
        (A) LENGTH: 412 amino acids (B) TYPE: amino acid
(D) TOPOLOGY: linear (ii) MOLECULE TYPE: protein (xi) SEQUENCE DESCRIPTION: SEQ ID NO:12:

```
Met Asn Glu Leu Val Lys Asp Leu Gly Leu Asn Arg Ser Asp Pro Ile
 1               5                  10                  15

Gly Ala Val Arg Arg Leu Ala Ala Gln Trp Gly Ala Thr Ala Val Asp
                20                  25                  30

Arg Asp Arg Ala Gly Gly Ser Ala Thr Ala Glu Leu Asp Gln Leu Arg
            35                  40                  45

Gly Ser Gly Leu Leu Ser Leu Ser Ile Pro Ala Ala Tyr Gly Gly Trp
 50                  55                  60

Gly Ala Asp Trp Pro Thr Thr Leu Glu Val Ile Arg Glu Val Ala Thr
 65                  70                  75                  80

Val Asp Gly Ser Leu Ala His Leu Phe Gly Tyr His Leu Gly Cys Val
                85                  90                  95

Pro Met Ile Glu Leu Phe Gly Ser Ala Pro Gln Lys Glu Arg Leu Tyr
            100                 105                 110

Arg Gln Ile Ala Ser His Asp Trp Arg Val Gly Asn Ala Ser Ser Glu
        115                 120                 125

Asn Asn Ser His Val Leu Glu Trp Lys Leu Ala Ala Thr Ala Val Asp
130                 135                 140

Asp Gly Gly Phe Val Leu Asn Gly Ala Lys His Phe Cys Ser Gly Ala
145                 150                 155                 160

Lys Ser Ser Asp Leu Leu Ile Val Phe Gly Val Ile Gln Asp Glu Ser
                165                 170                 175

Pro Leu Arg Gly Ala Ile Ile Thr Ala Val Ile Pro Thr Asp Arg Ala
            180                 185                 190

Gly Val Gln Ile Asn Asp Asp Trp Arg Ala Ile Gly Met Arg Gln Thr
        195                 200                 205

Asp Ser Gly Ser Ala Glu Phe Arg Asp Val Arg Val Tyr Pro Asp Glu
210                 215                 220

Ile Leu Gly Ala Pro Asn Ser Val Val Glu Ala Phe Val Thr Ser Asn
225                 230                 235                 240

Arg Gly Ser Leu Trp Thr Pro Ala Ile Gln Ser Ile Phe Ser Asn Val
                245                 250                 255

Tyr Leu Gly Leu Ala Arg Gly Ala Leu Glu Ala Ala Asp Tyr Thr
            260                 265                 270

Arg Thr Gln Ser Arg Pro Trp Thr Pro Ala Gly Val Ala Lys Ala Thr
        275                 280                 285

Glu Asp Pro His Ile Ile Ala Thr Tyr Gly Glu Leu Ala Ile Ala Leu
290                 295                 300

Gln Gly Ala Glu Ala Ala Ala Arg Glu Val Ala Ala Leu Leu Gln Gln
305                 310                 315                 320

Ala Trp Asp Lys Gly Asp Ala Val Thr Pro Glu Glu Arg Gly Gln Leu
                325                 330                 335

Met Val Lys Val Ser Gly Val Lys Ala Leu Ser Thr Lys Ala Ala Leu
            340                 345                 350

Asp Ile Thr Ser Arg Ile Phe Glu Thr Thr Gly Ser Arg Ser Thr His
        355                 360                 365

Pro Arg Tyr Gly Phe Asp Arg Phe Trp Arg Asn Ile Arg Thr His Thr
370                 375                 380

Leu His Asp Pro Val Ser Tyr Lys Ile Val Asp Val Gly Asn Tyr Thr
```

```
385           390           395           400
Leu Asn Gly Thr Phe Pro Val Pro Gly Phe Thr Ser
                405                 410
```

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AATTATCGAT GAATTCCCGG GCCTGAGGAG ATCTTCGAAC TAGTA          45

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AGCTTACTAG TTCGAAGATC TCCTCAGGCC CGGGAATTCA TCGAT          45

(2) INFORMATION FOR SEQ ID NO:15:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

ATCGGAATTC TCTAGAAGAT CTGATCGTGG AGGATGATTA AATGACAAGC CGCGTCGACC    60

CCGCAAAC                                                                                68

(2) INFORMATION FOR SEQ ID NO:16:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TAATAAGCTT ACTAGTTTAG CGATGTCGGT TCAGAGAATT ATTGAGGAAC TCCGGAGCGT    60

TGGGTACCGG GCAGTTGCTG TAG                                              83

(2) INFORMATION FOR SEQ ID NO:17:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AATTCTAGAG AGGAACTCCA TGCCAATCAA TTGCAAAGCC CGGGACTAGT A        51

(2) INFORMATION FOR SEQ ID NO:18:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AGCTTACTAG TCCCGGGCTT TGCAATTGAT TGGCATGGAG TTCCTCTCTA G        51

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CGATCTAGAG GAGGCTTCAT ATGTTTAAAC TAGTC        35

(2) INFORMATION FOR SEQ ID NO:20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCGAGACTAG TTTAAACATA TGAAGCCTCC TCTAGAT        37

(2) INFORMATION FOR SEQ ID NO:21:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 40..60

(xi) SEQUENCE DESCRIPTION: SEQ ID NO:21:

```
GATCCACTAG TCCTGAGGAC ATCCATGAGG AGATAACCG ATG TCT GAC AAG CCG        54
                                            Met Ser Asp Lys Pro
                                              1               5

AAT GCC GCATGCTACG TATTAATTAA ACTAGTA        87
Asn Ala
```

(2) INFORMATION FOR SEQ ID NO:22:

(i) SEQUENCE CHARACTERISTICS:
        (A) LENGTH: 7 amino acids
        (B) TYPE: amino acid
        (D) TOPOLOGY: linear -continued

```
    (ii) MOLECULE TYPE: protein (xi) SEQUENCE DESCRIPTION: SEQ ID NO:22:

Met Ser Asp Lys Pro Asn Ala
  1               5

(2) INFORMATION FOR SEQ ID NO:23:

(i) SEQUENCE CHARACTERISTICS:
         (A) LENGTH: 87 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:23:

AGCTTACTAG TTTAATTAAT ACGATGCATG CGGCATTCGG CTTGTCAGAC ATCGGTTATC        60

TCCTCATGGA TGTCCTCAGG ACTAGTG                                          87
```

DSZ GENE EXPRESSION IN PSEUDOMONAS HOSTS

RELATED APPLICATIONS

This application is a Continuation-in-part of Ser. No. 08/835,185, filed Apr. 7, 1997, now abandoned the contents of which are incorporated herein by reference in its entirety.

BACKGROUND OF THE INVENTION

The microbial desulfurization of fossil fuels has been an area of active investigation for over fifty years. The object of these investigations has been to develop biotechnology based methods for the pre-combustion removal of sulfur from fossil fuels, such as coal, crude oil and petroleum distillates. The driving forces for the development of desulfurization methods are the increasing levels of sulfur in fossil fuel and the increasingly stringent regulation of sulfur emissions. Monticello et al., "practical Considerations in Biodesulfurization of Petroleum," IGT's 3d Intl. Symp. on Gas, Oil, Coal and Env. Biotech., (Dec. 3–5, 1990) New Orleans, La.

Many biocatalysts and processes have been developed to desulfurize fossil fuels, including those described in U.S. Pat. Nos. 5,356,801, 5,358,870, 5,358,813, 5,198,341, 5,132,219, 5,344,778, 5,104,801 and 5,002,888, incorporated herein by reference. Economic analyses indicate that one limitation in the commercialization of the technology is improving the reaction rates and specific activities of the biocatalysts, such as the bacteria and enzymes that are involved in the desulfurization reactions. The reaction rates and specific activities (sulfur removed/hour/gram of biocatalyst) that have been reported in the literature are much lower than those necessary for optimal commercial technology. Therefore, improvements in the longevity and specific activity of the biocatalyst are desirable.

SUMMARY OF THE INVENTION

The present invention provides novel recombinant pseudomonads which contain a heterologous nucleic acid molecule comprising a nucleotide sequence encoding one or more desulfurization enzymes which are components of a biodesulfurization catalyst. Such enzymes catalyze one or more steps of a biodesulfurization process, for example, the oxidative cleavage of the carbon-sulfur bonds of an organosulfur compound. The invention also includes a method for producing such recombinant organisms.

In one embodiment, the nucleotide sequence which encodes the desulfurization enzyme(s) is derived from a Rhodococcus organism, such as Rhodococcus sp. IGTS8. In another embodiment, the nucleotide sequence is derived from a Sphingomonas organism, such as Sphingomonas sp. strain AD109.

The recombinant organism can be derived from a host organism which does not contain native genes encoding a biodesulfurization catalyst. Such an organism can be, for example, a bacterium which is a species of Pseudomonas. The recombinant organism can also be derived from a host organism which contains native genes encoding a biodesulfurization catalyst. The invention is predicated upon the discovery that pseudomonas hosts possess advantages over other host cells in the desulfurization of fossil fuels.

In a further embodiment, the invention provides a method of desulfurizing a carbonaceous material, such as a fossil fuel, which comprises organosulfur compounds. The method includes the steps of (1) contacting the fossil fuel with an aqueous phase containing a recombinant biocatalyst and, optionally, a flavoprotein, thereby forming a fossil fuel and aqueous phase mixture; (2) maintaining the mixture under conditions sufficient for biocatalysis, thereby resulting in a fossil fuel having a reduced organic sulfur content; and (3) separating the fossil fuel having a reduced organic sulfur content from the resulting aqueous phase.

The invention also provides a method of oxidizing an organic compound. The method comprises the steps of: (1) contacting the organic compound with an aqueous phase containing a recombinant pseudomonad biocatalyst comprising at least one enzyme capable of catalyzing at least one step in the oxidative cleavage of carbon-sulfur bonds, thereby forming an organic compound and aqueous phase mixture; (2) maintaining the mixture of step (1) under conditions sufficient for oxidation of the organic compound by the biocatalyst, thereby resulting in an oxidized organic compound, and, optionally, separating the oxidized organic compound from the aqueous phase.

BRIEF DESCRIPTION OF THE DRAWINGS

FIGS. 1A, 1B, 1C and 1D set forth the DNA sequence and predicted amino acid sequence of open reading frame 1 (ORF-1(R)) of the nucleotide sequence required for desulfurization activity in Rhodococcus sp. strain IGTS8.

FIGS. 2A, 2B and 2C set forth the DNA sequence and predicted amino acid sequence of open reading frame 2 (ORF-2(R)) of the nucleotide sequence required for desulfurization activity in Rhodococcus sp. strain IGTS8.

FIGS. 3A, 3B and 3C set forth the DNA sequence and predicted amino acid sequence of open reading frame 3 (ORF-3(R)) of the nucleotide sequence required for desulfurization activity in Rhodococcus sp. strain IGTS8.

FIGS. 4A, 4B, 4C and 4D set forth the DNA sequence and predicted amino acid sequence of open reading frame 1 (ORF-1(S)) of the nucleotide sequence required for desulfurization activity in Sphingomonas sp. strain AD109.

FIGS. 5A, 5B, and 5C set forth the DNA sequence and predicted amino acid sequence of open reading frame 2 (ORF-2(S)) of the nucleotide sequence required for desulfurization activity in Sphingomonas sp. strain AD109.

FIGS. 6A, GB and 6C set forth the DNA sequence and predicted amino acid sequence of open reading frame 3 (ORF-3(S)) of the nucleotide sequence required for desulfurization activity in Sphingomonas sp. strain AD109.

FIG. 18 sets forth the nucleotide sequence of the frdA linker.

DETAILED DESCRIPTION OF THE INVENTION

Figure 7:
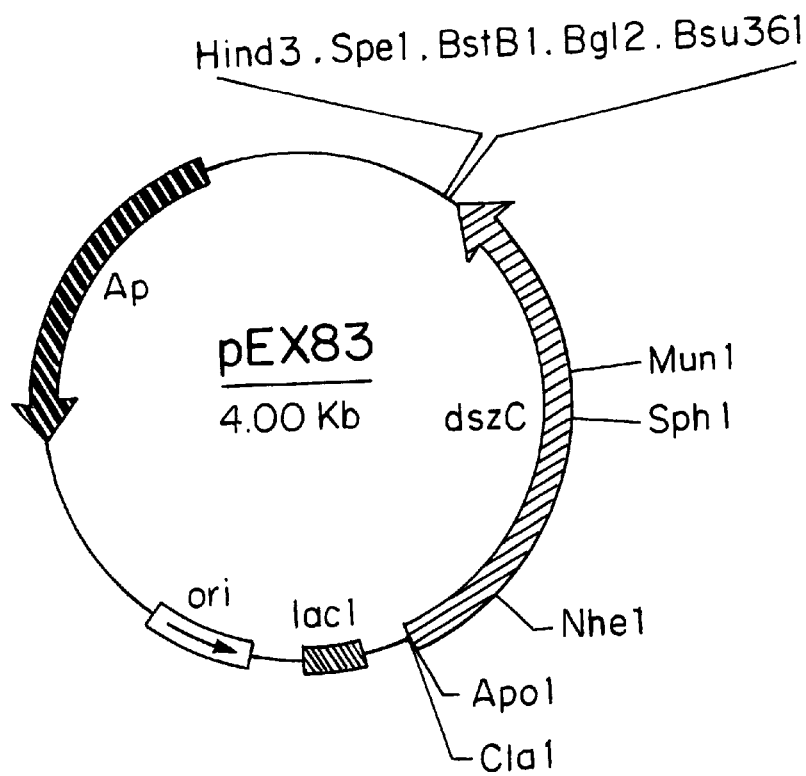
FIG. 7 is a physical map of plasmid pEX83.

The present invention is based upon the successful expression of heterologous biodesulfurization genes in pseudomonad host organisms and the advantages thereof. The resulting recombinant organisms can express a heterologous biocatalyst which catalyzes the oxidative cleavage of the carbon-sulfur bonds of an organosulfur compound. Such organisms, or enzyme preparations derived therefrom, can be utilized as biodesulfurization catalysts in the desulfurization of a carbonaceous material comprising one or more organosulfur compounds, such as a fossil fuel.

In the petroleum extraction and refining arts, the term "organic sulfur" is generally understood as referring to organic molecules having a hydrocarbon framework to which one or more sulfur atoms are covalently joined. These sulfur atoms can be directly bonded to the hydrocarbon framework, e.g., by one or more carbon-sulfur bonds, or can be present in a substituent bonded to the hydrocarbon framework of the molecule, e.g., a sulfate group. The general class of organic molecules having one or more sulfur heteroatoms are sometimes referred to as "organosulfur compounds". The hydrocarbon portion of these compounds can be aliphatic and/or aromatic.

Sulfur-bearing heterocycles, such as substituted and unsubstituted thiophene, benzothiophene, and dibenzothiophene, are known to be stable to conventional desulfurization treatments, such as hydrodesulfurization (HDS). Sulfur-bearing heterocycles can have relatively simple or relatively complex chemical structures. In complex heterocycles, multiple condensed aromatic rings, one or more of which can be heterocyclic, are present. The difficulty of desulfurization generally increases with the structural complexity of the molecule. That is, refractory behavior is particularly accentuated in complex sulfur-bearing heterocycles, such as dibenzothiophene (DBT, $C_{12}H_8S$).

DBT is a sulfur-bearing heterocycle that has a condensed, multiple aromatic ring structure in which a five-membered thiophenic ring is flanked by two six-membered benzo rings. Much of the residual post-HDS organic sulfur in fossil fuel refining intermediates and combustible products is thiophenic sulfur. The majority of this residual thiophenic sulfur is present in DBT and derivatives thereof having one or more alkyl or aryl groups attached to one or more carbon atoms present in one or both flanking benzo rings. DBT itself is accepted as a model compound illustrative of the behavior of the class of compounds encompassing DBT and derivatives thereof in reactions involving thiophenic sulfur (Monticello and Finnerty, *Ann. Rev. Microbiol.*, 39:371–389 (1985)). DBT and derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom (Monticello and Finnerty (1985), supra). Another characteristic of DBT and derivatives thereof is that, following a release of fossil fuel into the environment, these sulfur-bearing heterocycles persist for long periods of time without significant biodegradation. Gundlach et al., *Science* 221:122–129 (1983). Thus, most prevalent naturally occurring microorganisms do not effectively metabolize and break down sulfur-bearing heterocycles.

A fossil fuel that is suitable for desulfurization treatment according to the present invention is one that contains organic sulfur. Such a fossil fuel is referred to as a "substrate fossil fuel". Substrate fossil fuels that are rich in thiophenic sulfur are particularly suitable for desulfurization according to the method described herein. Examples of such substrate fossil fuels include Cerro Negro or Orinoco heavy crude oils; Athabascan tar and other types of bitumen; petroleum refining fractions such as light cycle oil, heavy atmospheric gas oil, and No. 1 diesel oil; and coal-derived liquids manufactured from sources such as Pocahontas #3, Lewis-Stock, Australian Glencoe or Wyodak coal.

Biocatalytic desulfurization (biocatalysis or BDS) is the excision (liberation or removal) of sulfur from organosulfur compounds, including refractory organosulfur compounds such as sulfur-bearing heterocycles, as a result of the oxidative, preferably selective, cleavage of carbonsulfur bonds in said compounds by a biocatalyst. BDS treatment yields the desulfurized combustible hydrocarbon framework of the former refractory organosulfur compound, along with inorganic sulfur substances which can be readily separated from each other by known techniques such as fractional distillation or water extraction. For example, DBT is converted into 2-hydroxybiphenyl (also referred to as "HBP") when subjected to BDS treatment. The present invention provides a biocatalyst of use in a BDS process comprising one or more recombinant pseudomonads that functionally express one or more enzymes that direct, singly or in concert with each other, the removal of sulfur from organosulfur compounds, including sulfur-bearing heterocycles, by the selective cleavage of carbon-sulfur bonds in said compounds; one or more enzymes obtained from such microorganisms; or a mixture of such microorganisms and enzymes.

Suitable sources of the heterologous nucleic acid molecule of the invention are organisms which exhibit biocatalytic desulfurization activity, also referred to as $Dsz^+$ organisms. Several such organisms are known in the art. For example, investigators have reported the genetic modification of naturally-occurring bacteria into mutant strains capable of catabolizing DBT. Kilbane, J. J., *Resour. Cons. Recycl.* 3:69–79 (1990), Isbister, J. D., and R.C. Doyle, U.S. Pat. No. 4,562,156 (1985), and Hartdegan, F. J. et al., *Chem. Eng. Progress*: 63–67 (1984).

Kilbane has reported a mixed bacterial culture which appeared capable of selectively liberating sulfur from DBT by the oxidative pathway. This culture was composed of bacteria obtained from natural sources such as sewage sludge, petroleum refinery wastewater, garden soil, coal tar-contaminated soil, etc., and maintained in culture under conditions of continuous sulfur deprivation in the presence of DBT. The culture was then exposed to the chemical mutagen 1-methyl-3-nitro-l-nitrosoguanidine. The major catabolic product of DBT metabolism by this mutant culture was 2-hydroxybiphenyl; sulfur was released as inorganic water-soluble sulfate, and the hydrocarbon portion of the molecule remained essentially intact as 2-hydroxybiphenyl. Kilbane, J. J., *Resour. Cons. Recycl.*, 3: 69–79 (1990), the teachings of which are incorporated herein by reference.

Kilbane isolated a mutant strain of Rhodococcus from this mixed bacterial culture. This mutant, IGTS8 or ATCC No. 53968, is a particularly preferred source of the heterologous nucleic acid molecule for use with the instant invention. The isolation and characteristics of this mutant are described in detail in J. J. Kilbane, U.S. Pat. No. 5,104,801, the teachings of which are incorporated herein by reference. This microorganism has been deposited at the American Type Culture Collection (ATCC), 12301 Park Lawn Drive, Rockville, Md. U.S.A. 20852 under the terms of the Budapest Treaty, and has been designated as ATCC Deposit No. 53968.

There are at least two possible types of pathways which result in the specific release of sulfur from DBT: oxidative and reductive. Preferably, an oxidative (aerobic) pathway can be followed. Examples of microorganisms that act by this oxidative pathway, preparations of which are suitable for use as the source of recombinant DNA in the present invention include the microbial consortium (a mixture of several microorganisms) disclosed in Kilbane, *Resour. Conserv. Recycl.*, 3:69–79 (1990), the microorganisms disclosed by Kilbane in U.S. Pat. Nos. 5,002,888 (issued Mar. 26, 1991), 5,104,801 (issued Apr. 14, 1992), 5,344,778, 5,132, 219, 5,198,341, 5,356,813 and 5,358,870 [also described in Kilbane (1990), Biodesulfurization: Future Prospects in Coal Cleaning, in *Proc*, 7 *th Ann. Int'l. Pittsburgh Coal Conf.*: 373–382]. Preferred sources of the heterologous nucleic acid molecules of the invention are Rhodococcus sp. IGTS8 (ATCC 53968) and Sphingomonas sp. strain AD109. Other desulfurizing microorganisms which are suitable nucleic acid molecule sources include Corynebacterium sp. strain SY1, as disclosed by Omori et al., *Appl. Env. Microbiol.*, 58:911–915 (1992); *Rhodococcus erythropolis* D-1, as disclosed by Izumi et al., *Appl. Env. Microbiol.*, 60:223–226 (1994); the Arthrobacter strain described by Lee et al., *Appl. Environ. Microbiol.* 61:4362–4366 (1995) and the Rhodococcus strains (ATCC 55309 and ATCC 55310) disclosed by Grossman et al., U.S. Pat. No. 5,607,857, each of which is incorporated herein by reference in its entirety. Each of these microorganisms is believed to produce one or more enzymes (protein biocatalysts) that catalyze one or more reactions in the desulfurization of DBT.

Each of the foregoing microorganisms can serve as the source of recombinant DNA in the present invention because each contains one or more genes encoding one or more enzymes (protein biocatalysts) that carry out the specific chemical reaction(s) by which sulfur is excised from refractory organosulfur compounds. Mutational or genetically engineered derivatives of any of the foregoing microorganisms, as exemplified by the U.S. patents listed above, can also be used as the DNA source, provided that appropriate biocatalytic function is retained.

The genes from Rhodococcus strain sp. IGTS8 which encode the biodesulfurization catalyst have been isolated and cloned, as described in U.S. Pat. No. 5,356,801, the contents of which are incorporated herein by reference. The DNA sequence required for expression of desulfurization activity in Rhodococcus comprises three open reading frames, designated dszA, dszB and dszC. Each of these genes encodes an enzyme, denoted DszA, DszB and DszC, respectively, which catalyzes one or more steps in the desulfurization of DBT. These enzymes have been isolated and characterized (Gray et al., *Nature Biotech.* 14:1705–1709 (1996). The nucleotide sequences of the Rhodococcus desulfurization genes are set forth in FIGS. 1A–1D (ORF-1(R), SEQ ID NO.: 1), FIGS. 2A–2C (ORF-2(R), SEQ ID NO.: 3) and FIGS. 3A–3C (ORF-3(R), SEQ ID NO.: 5). Each of these figures also sets forth the predicted amino acid sequences of the proteins encoded by these nucleotide sequences (ORF-1(R), SEQ ID NO.: 2; ORF-2 (R), SEQ ID NO.: 4 and ORF-3(R), SEQ ID NO.: 6).

Recent experiments, including confirming sequencing of these genes, have raised the possibility that amino acid 56 has been misidentified as an alanine versus a glycine. Thus, SEQ ID NO.: 6, (and, thus, the corresponding codon) includes a 56 G "substitution" variant. In light of the fact that sequencing errors are common in the industry, references to specific sequences herein refer to the native sequences isolated from the host organism.

The isolation and characterization of the desulfurizing organism Sphingomonas sp. strain AD109 (ATCC Deposit No. 55954 on Apr. 21, 1997) are described in copending U.S. patent application Ser. No. 08/851,089 the contents of which are incorporated herein in their entirety. This organism has been isolated as a biologically pure culture by a soil enrichment procedure using 2-(2-hydroxyphenyl) benzenesulfinate (also referred to as "HPBS") as the sole source of sulfur. This organism expresses a collection of desulfurization enzymes which, together, catalyze the conversion of DBT to 2-hydroxybiphenyl and inorganic sulfur. The nucleotide sequence encoding the desulfurization catalyst of this organism includes three open reading frames which exhibit substantial homology with the corresponding nucleotide sequences of Rhodococcus IGTS8. The sequences of these open reading frames are set forth in FIGS. 4A–4D (ORF-1(S), SEQ ID NO.: 7), FIGS. 5A–5C (ORF-2(S), SEQ ID NO.: 9) and FIGS. 6A–6C (ORF-3(S), SEQ ID NO.: 11). FIGS. 4–6 also present the predicted amino acid sequences of the proteins encoded by each of these nucleotide sequences (ORF-1(S), SEQ ID NO.: 8; ORF-2(S),SEQ ID NO.: 10 and ORF-3(S), SEQ ID NO.: 12).

The heterologous nucleic acid molecule of the invention can comprise one or more nucleotide sequences encoding an enzyme which is a component of a biodesulfurization catalyst of a desulfurizing organism. Such an enzyme, also referred to as a "desulfurization enzyme", catalyzes one or more steps in the oxidative cleavage of one or more carbon-sulfur bonds of an organosulfur compound. The heterologous nucleic acid molecule, can, for example, comprise one or more nucleotide sequences which encode a desulfurization enzyme of a Dsz$^+$ organism, such as one or more enzymes having an amino acid sequence as set forth in SEQ ID NO.: 2, SEQ ID NO.: 4, SEQ ID NO.: 6, SEQ ID NO.: 8, SEQ ID NO.: 10 or SEQ ID NO.: 12.

For example, the heterologous nucleic acid molecule can comprise a nucleotide sequence which is identical to a native desulfurization enzyme-encoding sequence of a Dsz$^+$ organism. For example, the heterologous nucleic acid molecule can comprise one or more of the nucleotide sequences set forth in SEQ ID NO.: 1, SEQ ID NO.: 3, SEQ ID NO.: 5, SEQ ID NO.: 7, SEQ ID NO.: 9, and SEQ ID NO.: 11.

The heterologous nucleotide molecule can also comprise one or more nucleotide sequences which result from one or more silent mutations of a desulfurization enzyme-encoding sequence of a Dsz$^+$ organism, such as Rhodococcus IGTS8 or Sphingomonas sp. strain AD109. Such a mutant sequence results from the substitution of one or more codons in the native sequence with a degenerate codon, i.e., a codon encoding the same amino acid residue.

The heterologous nucleic acid molecule can also include a nucleotide sequence which is homologous to the native nucleotide sequence of a desulfurizing organism, for example, a nucleotide sequence which is homologous to one of the sequences set forth in SEQ ID NO.: 1, SEQ ID NO.: 3, SEQ ID NO.: 5, SEQ ID NO.: 7, SEQ ID NO.: 9, and SEQ ID NO.: 11. Preferably the nucleotide sequence exhibits at least about 50% sequence homology or sequence identity with a native sequence, preferably at least about 70% homology, and, more preferably, at least about 80% homology. It is particularly preferred that the nucleotide sequence exhibit at least about 95% sequence homology with, or is essentially or substantially the same as, a native sequence.

The heterologous nucleic acid molecule can comprise a nucleotide sequence which encodes an amino acid sequence variant of one or more desulfurization enzymes of a desulfurizing organism, such as an amino acid sequence variant of one or more of the desulfurization enzymes of Rhodococcus IGTS8 and Sphingomonas sp. strain AD109. Such amino acid variants can be substitution, deletion or insertion mutants. Preparation of mutant nucleotide sequences can be accomplished by methods known in the art as are described in Old, et al., *Principles of Gene Manipulation*, Fourth Edition, Blackwell Scientific Publications (1989), in Ausubel et al., *Current Protocols in Molecular Biology*, Wiley-Interscience, New York (1997) (hereinafter "Ausubel et al.") and in Sambrook et al., *Molecular Cloning: A Laboratory Manual*, third edition, Cold Spring Harbor Laboratory Press (1992) (hereinafter "Sambrook et al."), each of which are incorporated herein by reference.

The amino acid sequence variant preferably exhibits at least about 50% sequence homology to a native desulfurization enzyme of a $Dsz^+$ organism, preferably at least about 70% homology, and more preferably at least about 80% sequence homology in an amino acid alignment. It is particularly preferred that the variant enzyme exhibits at least about 95% sequence homology with, or is essentially the same as, a native desulfurization enzyme. An amino acid alignment can be constructed by methods known in the art, for example, with the aid of a computer program, such as the BLAST program (Altschul et al., *J. Mol. Biol.* 215:403–410 (1990)). For example, the amino acid sequence variant can have an amino acid sequence which is homologous to one of the sequences presented in SEQ ID NO.: 2, SEQ ID NO.: 4, SEQ ID NO.: 6, SEQ ID NO.: 8, SEQ ID NO.: 10 or SEQ ID NO.: 12.

It is preferred to substitute amino acids which are not conserved among the desulfurization enzymes of two or more desulfurizing organisms, such as Rhodococcus IGTS8 and Sphingomonas sp. strain AD109. For example, the amino acid sequence variant encoded by the heterologous nucleic acid molecule preferably retains the amino acid residues which are conserved in the Rhodococcus and Sphingomonas desulfurization enzymes. The heterologous nucleic acid molecule can comprise the corresponding codons which are conserved in one or more of the Rhodococcus and Sphingomonas desulfurization genes, or one or more codons of these genes can be substituted with degenerate codons which encode the conserved amino acids.

The amino acid sequence variant encoded by the heterologous nucleic acid molecule can also result from conservative substitutions of one or more amino acid residues which are conserved in the desulfurization enzymes of two or more desulfurization organisms, such as Rhodococcus IGTS8 and Sphingomonas sp. strain AD109. Conservative substitutions are those in which a first amino acid residue is substituted by a second residue having similar side chain properties. An example of such a conservative substitution is replacement of one hydrophobic residue, such as valine, with another hydrophobic residue, such as leucine.

The amino acid sequence variant can also result from the conservative or nonconservative substitution of one or more amino acid residues which are not conserved in the desulfurization enzymes of two or more desulfurization organisms, such as Rhodococcus IGTS8 and Sphingomonas sp. strain AD109. A non-conservative substitution involves replacing a first residue with a second residue having different side chain properties. An example of a non-conservative substitution is the replacement of a hydrophobic residue, such as valine, with an acidic residue, such as glutamic acid.

The heterologous nucleic acid molecule can also encode an active fragment of one or more desulfurization enzymes. Preferred nucleic acid molecules of this type encode a significant portion of the enzyme and include at least one region, e.g. a series of contiguous conserved amino acid residues, of at least one desulfurization enzyme, which is conserved among two or more $Dsz^+$ organisms, such as Rhodococcus IGTS8 and Sphingomonas sp. strain AD109.

Additional $Dsz^+$ microorganisms suitable as the source of the recombinant DNA can be derived from naturally occurring microorganisms by known techniques. As set forth above, these methods involve culturing preparations of microorganisms obtained from natural sources such as sewage sludge, petroleum refinery wastewater, garden soil, or coal tar-contaminated soil under selective culture conditions in which the microorganisms are grown in the presence of refractory organosulfur compounds such as sulfur-bearing heterocycles as the sole sulfur source; exposing the microbial preparation to chemical or physical mutagens; or a combination of these methods. Such techniques are recounted by Isbister and Doyle in U.S. Pat. No. 4,562,156 (issued Dec. 31, 1985); by Kilbane in Resour. *Conserv. Recycl.*, 3:69–79 (1990), U.S. Pat. Nos. 5,002,888, 5,104,801 and 5,198,341; and by Omori and coworkers in *Appl. Env. Microbiol.*, 58:911–915 (1992), all incorporated herein by reference.

In another embodiment, the recombinant organism contains a heterologous nucleotide sequence which encodes one or more desulfurization enzymes as well as an oxidoreductase, such as a flavoprotein, for example, a flavin reductase. For example, the heterologous nucleotide sequence can encode an oxidoreductase which is native to Sphingomonas sp. strain AD109. The heterologous nucleic acid molecule can also encode the oxidoreductase denoted DszD described in copending U.S. patent application Ser. No. 08/583,118; the flavin reductase from *Vibrio harveyii* described in copending U.S. patent application Ser. No. 08/351,754; or the flavin reductase from Rhodococcus sp. IGTS8, described in copending U.S. patent application Ser. No. 08/735,963. The contents of each of these references is incorporated herein by reference. The heterologous nucleotide sequence can also encode an amino acid variant or an active fragment of one of these oxidoreductases.

The recombinant pseudomonad of the invention can be derived from any pseudomonad which is capable of taking up and expressing heterologous desulfurization genes. The "term pseudomonad", as used herein, refers to any bacterium classified as a Pseudomonas species in Krieg et al., ed., *Bergey's Manual of Systematic Bacteriology*, Williams and Wilkins, Baltimore (1984). In a preferred embodiment, the host organism is resistant to the conditions encountered in a biodesulfurization process. For example, particularly preferred are microorganisms which are resistant to the compounds present in a fossil fuel, such as petroleum, as well as to the high salt concentrations and elevated temperatures which can be encountered in a BDS system. Suitable pseudomonads include *Pseudomonas fluorescens, Burkholderia cepacia, Comomonas testosteroni, Pseudomonas aeruginosa, Pseudomonas aureofaciens, Pseudomonas alcaligenes, Pseudomonas chlororaphis, Pseudomonas denitrifcans, Pseudomonas fluorescens, Pseudomonas mendocina, Pseudomonas oleovorans, Pseudomonas putida, Pseudomonas stutzeri*, and *Sphingomonas paucimobilis*. A preferred host microorganism is a strain of *P. fluorescens*, such as *P. fluorescens* NCIB 11764 and *P. fluorescens* ATCC 13525.

The recombinant organisms of the present invention can be created by various methods by those skilled in the art. Any method for introducing a recombinant plasmid into the organism of choice can be used, and a variety of such methods are described by Sambrook et al. and Ausubel et al. For example, the recombinant plasmid can be introduced via a suitable vector or by electroporation.

The present invention also provides a method for desulfurizing a carbonaceous material which includes organosulfur compounds. The carbonaceous material can be, for example, a fossil fuel, such as petroleum, a petroleum distillate fraction or coal. The method comprises the steps of (1) contacting the carbonaceous material with an aqueous phase containing a recombinant pseudomonad biocatalyst comprising at least one enzyme capable of catalyzing at least one step in the oxidative cleavage of carbon-sulfur bonds, thereby forming a carbonaceous material and aqueous phase mixture; (2) maintaining the mixture of step (1) under conditions sufficient for cleavage of the carbon-sulfur bonds of the organic sulfur molecules by the biocatalyst, thereby resulting in a carbonaceous material having a reduced organic sulfur content; and (3) separating the carbonaceous material having a reduced organic sulfur content from the resulting aqueous phase.

The term "recombinant pseudomonad biocatalyst", as used herein, refers to a recombinant pseudomonad organism which contains a heterologous nucleic acid molecule which encodes one or more desulfurization enzymes, or an enzyme preparation derived therefrom, such as a cell lysate. Preferably, the recombinant organism is as described above, such as a recombinant pseudomonad comprising recombinant DNA derived from a $Dsz^+$ microorganism, such as Rhodococcus sp. IGTS8 or Sphingomonas sp. strain AD109.

Although living microorganisms (e.g., a culture) can be used as the biocatalyst herein, this is not required. Biocatalytic enzyme preparations that are useful in the present invention include microbial lysates, extracts, fractions, subfractions, or purified products obtained by conventional means and capable of carrying out the desired biocatalytic function. In a particularly preferred embodiment, the biocatalyst is overexpressed in the recombinant host cell (such as a cell which contains more than one copy of the gene or genes).

Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the treated fossil fuel which has been depleted of refractory organosulfur compounds.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms is used as the biocatalyst preparation, a suitable culture medium lacking a sulfur source other than sulfur-bearing heterocycles can be inoculated with suitable microorganisms and grown until a desired culture density is reached. The resulting culture can be diluted with additional medium or another suitable buffer, or microbial cells present in the culture can be retrieved e.g., by centrifugation, and resuspended at a greater concentration than that of the original culture. The concentrations of microorganism and enzyme biocatalyst can be adjusted similarly. In this manner, appropriate volumes of biocatalyst preparations having predetermined specific activities and/or concentrations can be obtained.

In the biocatalytic desulfurization stage, the liquid fossil fuel containing sulfur-bearing heterocycles is combined with the biocatalyst and the flavin reductase. The relative amounts of biocatalyst and flavin reductase and liquid fossil fuel can be adjusted to suit particular conditions, or to produce a particular level of residual sulfur in the treated, deeply desulfurized fossil fuel. The amount of biocatalyst preparation to be combined with a given quantity of liquid fossil fuel will reflect the nature, concentration and specific activity of the particular biocatalyst used, as well as the nature and relative abundance of inorganic and organic sulfur compounds present in the substrate fossil fuel and the degree of deep desulfurization sought or considered acceptable.

The method of desulfurizing a fossil fuel of the present invention involves two aspects. First, a host organism or biocatalytic preparation obtained therefrom is contacted with a fossil fuel to be desulfurized. This can be done in any appropriate container, optionally fitted with an agitation or mixing device. The mixture is combined thoroughly and allowed to incubate for a sufficient time to allow for cleavage of a significant number of carbon-sulfur bonds in organosulfur compounds, thereby producing a desulfurized fossil fuel. In one embodiment, an aqueous emulsion or microemulsion is produced with an aqueous culture of the organism or enzyme fraction and the fossil fuel, allowing the organism to propagate in the emulsion while the expressed biocatalyst cleaves carbon-sulfur bonds.

Variables such as temperature, pH, oxidation level, concentration, mixing rate and rate of desulfurization will vary according to the biocatalyst used. Optimal parameters can generally be determined through no more than routine experimentation.

When the fossil fuel is a liquid hydrocarbon, such as petroleum, the desulfurized fossil fuel and the aqueous phase can form an emulsion. The components of such emulsions can be separated by a variety of methods, such as those described in U.S. Pat. No. 5,358,870 and U.S. patent application Ser. No. 08/640,129, which are incorporated herein by reference. For example, some emulsions reverse spontaneously when maintained under stationary conditions for a suitable period of time. Other emulsions can be reversed by adding an additional amount of an aqueous phase. Still other emulsions can be separated by the addition of a suitable chemical agent, such as a demulsifying agent or by employing suitable physical conditions, such as a particular temperature range.

The biocatalyst can be recovered from the aqueous phase, for example, by centrifugation, filtration or lyophilization. When the biocatalyst is a microorganism, the biocatalyst can be resuspended in fresh sulfur-free nutrient medium and/or any fresh microorganism culture as necessary to reconstitute or replenish to the desired level of biocatalytic activity. The biocatalyst can then be reintroduced into the reaction system.

Several suitable techniques for monitoring the rate and extent of desulfurization are well-known and readily available to those skilled in the art. Baseline and time course samples can be collected from the incubation mixture, and prepared for a determination of the residual organic sulfur in the fossil fuel.

The disappearance of sulfur from organosulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

Without being limited to any particular mechanism or theory, it is believed that the pathway of the desulfurization reaction in Rhodococcus sp. IGTS8, and possibly in other Dsz+ organisms, is set forth below:

of dibenzothiophene to dibenzothiophene-5,5-dioxide (dibenzothiophene sulfone), and the enzymes of SEQ ID NO.: 1 and SEQ ID NO.: 7 catalyze the oxidation of dibenzothiophene-5,5-dioxide to 2-(2-hydroxyphenyl)

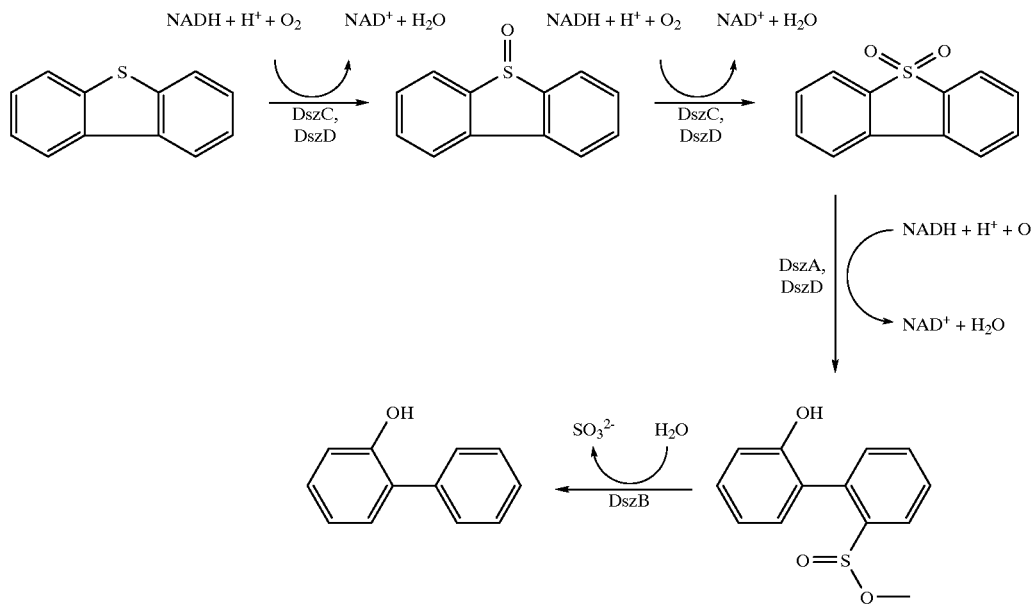

Here the flavin reductase provides an electron transport chain which delivers, via $FMNH_2$, the reducing equivalents from NADH (or other electron donor) to the enzymes DszC (or Sox C) and/or DszA (or Sox A). The enzyme DszC is responsible for the biocatalysis of the oxidation reaction of DBT to $DBTO_2$. The enzyme DszA is responsible for the reaction of $DBTO_2$ to 2-(2-hydroxyphenyl)benzenesulfinate (HPBS). The enzyme DszB catalyzes the conversion of HPBS to 2-hydroxybiphenyl and inorganic sulfur.

As such, it is particularly preferred to add the cofactor, FMN, to the reaction medium as well as an electron donor, NADH.

Another method of use of the recombinant Pseudomonas organisms of the invention is as catalysts for the oxidation of organic compounds. The method comprises the steps of (1) contacting the organic compound with an aqueous phase containing a recombinant pseudomonad biocatalyst comprising at least one enzyme capable of catalyzing at least one step in the oxidative cleavage of carbon-sulfur bonds, thereby forming an organic compound and aqueous phase mixture; (2) maintaining the mixture of step (1) under conditions sufficient for biocatalytic oxidation of the organic compound by the biocatalyst, thereby resulting in an oxidized organic compound, and, optionally, (3) separating the oxidized organic compound from the aqueous phase. In one embodiment, the organic compound is a heteroorganic compound, such as an organonitrogen compound or an organosulfur compound. In one embodiment, the organic compound is an organosulfur compound which is a component of a fossil fuel, such as petroleum or a petroleum distillate fraction. In a second embodiment, the organic compound is a substituted or unsubstituted indole, as described in U.S. Provisional patent Application Ser. No. 60/020,563, filed Jul. 2, 1996, which is incorporated herein by reference.

The enzymes having the amino acid sequence set forth in SEQ ID NO.: 6 and SEQ ID NO.: 12 catalyze the oxidation benzenesulfinate. In one embodiment the biocatalyst comprises an enzyme of SEQ ID NO.: 6 or SEQ ID NO.: 12, or a mutant, homologue or active fragment thereof; the organosulfur compound is substituted or unsubstituted dibenzothiophene; and the oxidized organosulfur compound is a substituted or unsubstituted dibenzothiophene-5,5-dioxide. In another embodiment the biocatalyst comprises an enzyme of SEQ ID NO.: 6 or SEQ ID NO.: 12, and an enzyme of SEQ ID NO.: 1 or SEQ ID NO.: 7; or a mutant, homologue or fragment thereof; the organosulfur compound is a substituted or unsubstituted dibenzothiophene; and the oxidized organosulfur compound is a substituted or unsubstituted 2-(2-hydroxyphenyl)benzenesulfinate. In yet another embodiment, the biocatalyst comprises the enzyme encoded by SEQ ID NO.: 1 or SEQ ID NO.: 7 or a mutant, homologue or active fragment thereof; the organosulfur compound is a substituted or unsubstituted dibenzothiophene-5,5-dioxide; and the oxidized organosulfur compound is a substituted or unsubstituted 2-(2-hydroxyphenyl)benzenesulfinate.

The oxidized organosulfur compound can, optionally, be further processed, for example, via a non-biological process or an enzyme-catalyzed reaction. In one embodiment, the oxidized organosulfur compound is desulfurized in a process employing suitable desulfurization enzymes from an organism other than a Sphingomonas.

The invention will now be further illustrated by way of the following examples.

EXAMPLES

General Materials and Methods

Bacterial strains and plasmids *E. coli* DH10β (F⁻ mcrA Δ (mrr-hsdRMS-mcrBC)φ80dlacZΔM15 ΔlacX74 deoR recA1 endA1 araD139 Δ (ara, leu)7697 galU galK lambda⁻ rpsL nupG; Gibco-BRL, Gaithersburg, Md.) was used as the cloning host. *Pseudomonas fluorescens* ATCC 13525

(American Type Culture Collection, Rockville, Md.) and *P. fluorescens* NCIB 11764 (Harris and Knowles, *J. Gen. Microbiol.* 129: 1005–1011 (1983)) were used as typical expression hosts for the Rhodococcus IGTS8 dsz genes.

Plasmids pUC18 and pUC19 were used as cloning vectors (Ap$^R$; Vieria and Messing, *Gene* 19: 259–268 (1982)). The IncQ based, broad-host range expression plasmid pEXY10 containing the salicylate inducible P$_G$ promoter is derived from plasmid pRWF113 (Frazee et al., *J. Bacteriol.* 175 6194–6202, (1993)), a derivative of plasmid pKMY319 (Yen, K.-W., *J. Bacteriol.* 173:5328–5335, (1991)). The construction of pEXY10 is detailed in Example 1. The fre gene was obtained from plasmid pfFRI (Zenno, S. and Saigo, K., *J. Bacteriol.* 176:3544–3551, (1994)). The source of the Rhodococcus erythropolis IGTS8 flavin reductase gene, frdA, was plasmid pEBC615. Plasmid pEBC443, which was used in the construction of pDA121, contains the dszA gene in the tac expression vector pT3X12 (Hale et al., *Cytokine* 7 :26–38 (1995)).

Media and Reagents

LB and 2YT media were routinely used to propagate *E. coli* and *P. fluorescens*. Luria broth (LB) is 1k tryptone (Difco), 0.5% yeast extract (Difco) and 0.5% NaCl. 2YT medium is 1.6% tryptone, 1% yeast extract and 0.5% NaCl. Basal salts minimal medium (BSM-glucose) contained the following (per liter) phosphate buffer, 100 mmol (pH 7.2); glucose, 20g: NH$_4$Cl, 2g; MgCl$_2$ 6H$_2$O, 644 mg; MnCl$_2$ 4H$_2$O, 33 mg; (NH4)$_6$MO$_7$O$_{24}$ 4H$_2$O, 0.09 mg; and EDTA, 1.25 mg. When required, the sulfur source was 2 mM MgSO$_4$. For solid media, agar or agarose was added a concentration of 1.5%. Dibenzothiophene (DBT) and dibenzothiophene sulfone (DBTO$_2$) were made up in acetonitrile as 50 mM stock solutions.

To screen for presence of the dsz genes, tetracycline-resistant P. fluorescens transconjugants were tested for the ability to produce clearing zones on a BSM Glucose DBTO$_2$ plate (final DBTO$_2$ concentration=400 μM)

The antibiotic concentrations for *E. coli* were as follows: ampicillin, 100 μg/ml; tetracycline, 15 μg/ml. The antibiotic concentrations for Pseudomonas were as follows: tetracycline, 30 μg/ml. For selection of Pseudomonas drug-resistant transconjugants, plate mating mixtures were plated on either Pseudomonas Isolation Agar (PIA; Difco) supplemented with tetracycline (300 μg/ml) or on BSM Glucose plates containing tetracycline.

DNA Methods

Restriction enzymes and T4 DNA ligase were purchased from New England Biolabs, Inc. (Beverly, Mass.) and used as recommended by the supplier. Small scale plasmid preparations from *E. coli* were carried out as described by Birboim and Doly (*Nuc. Acids Res.* 7:1513–1523 (1979)). Larger scale DNA preparations were carried out with Midiprep columns from Qiagen (Chatsworth, Calif.). DNA fragments were purified from agarose gels after electrophoretic separation by the method of Vogelstein and Gillespie (*Proc. Natl. Acad. Sci. USA* 76:615–619 (1979)). DNA fragments were cloned into vectors by using techniques described by Sambrook, et al. (Sambrook, J., Fritsch, E. F., and Maniatis, T., eds., *In Molecular Cloning: A Laboratory Manual.* Cold Spring Harbor Laboratory Press, 1992).

DNA samples were sequenced by SeqWright (Houston, Tex.) using a dye-terminator cycling sequencing kit from Perkin Elmer and the 373A and 377 ABI automatic DNA sequencer. The sequence was extended by synthesizing overlapping oligonucleotides to previously read sequence. The synthesized oligonucleotides were used as primers for continuing sequence reactions. Sequencing reads were assembled and edited to 99.990% accuracy using Genecode's Sequencher, version 3.0 computer software. DNA and protein sequence analysis was performed with the MacVector software program (Oxford Molecular Group, Campbell, Calif.).

Genetic Procedures

Plasmid DNA was introduced into *E. coli* DH10β by electroporation. Competent ElectroMAX DH10β (Gibco-BRL, Gaithersburg, Md.) were used according to the manufacturer's suggestions. Recombinant broad-host range plasmids were introduced into Pseudomonas and other gram-negative strains either by electroporation using standard techniques or by triparental plate matings with pRK2013 (Figurski and Helinski, *Proc. Natl. Acad. Sci. USA* 76:1648–1652 (1979)) as the mobilizing plasmid.

Preparation of cell-free extracts

Cells grown in the appropriate medium were concentrated to an optical density at 600 nm of 50 by centrifugation and resuspended in 25 mM phosphate buffer, pH 7.4, containing 100 mM NaCl, 0.5 mM dithiothreitol (DTT), and 1 mM phenylmethanesulfonyl fluoride (PMSF). Cells were disrupted in a French press and debris was removed by centrifugation at 32,000×g for 20 min. Cell lysates were stored on ice at 4° C.

Desulfurization and enzyme assays

Cell-free desulfurization assays was performed by incubating a crude lysate with 200 βM dibenzothiophene (DBT), 10 μM FMN, and 4 μM NADH in buffer containing 25 mM sodium phosphate buffer, pH 7.4, containing 100 mM NaCl and 0.5 MM DTT. 2-(2-hydroxyphenyl)benzenesulfinate (HPBS) desulfinase activity was determined by incubating a crude lysate with 200 μM HPBS in buffer. The reaction mixtures were shaken at 250 rpm at 30° C. At designated time points aliquots were removed and the reaction was quenched with acetonitrile. Substrate and product concentrations were quantitated by high-pressure liquid chromatography (HPLC) analysis.

Flavin reductase activity was measured by the FMN-dependent oxidation of NADH monitored at 340 nm as previously described (Gray et al., *Nature Biotechnology*, 14: 1705–1709 (1996))).

Single phase, in vivo desulfurization assays were performed by first diluting the cells to be tested into buffer consisting of 50 mM potassium phosphate buffer (pH 7.2)+ 1% glucose to an OD$_{600}$=0.5. The cell suspension was equilibrated in a 30° C. shaker bath (250 rpm) for several minutes before the addition of DBT (final concentration)= 200 μM). Aliquots were removed during the 60 minute incubation period, quenched with an equal volume of acetonitrile and centrifuged to remove the cell debris. Substrate and product concentrations were quantitated by HPLC analysis.

Whole cell, two phase desulfurization assays were performed by resuspending cell paste (the equivalent of 0.005 grams dry cell weight) in buffer consisting of 156 mM potassium phosphate (pH 7.2)+1% glucose. Following equilibration in a 30° C. shaker bath (250 rpm), one third volume of 0.6 wt % DBT in hexadecane was added. Samples of the aqueous phase were removed after 60 minutes, quenched with acetonitrile and analyzed as described above. The hexadecane phase was recovered after 24 hrs. and analyzed by gas chromatography (GC) for DBT and 2-HBP. Specific activity is reported as moles product/min/gram dry cell weight (gDCW).

Expression Studies *P. fluorescens* strains harboring the dsz expression plasmids pEX108Z or pDA121 (see below) were inoculated into 250 ml shake flasks containing 2YT medium+ tetracycline and allowed to grow with shaking at 30° C. At an $OD_{600}$ of approximately 0.9, the culture was induced by the addition of sodium salicylate (final conc. 250 µM) and allowed to grow for an additional 3–5 hrs. Alternatively, the strains were grown in a 1-liter fermentor

```
5'-AATTATCGATGAATTCCCGGGCCTGAGGAGATCTTCGAACTAGTA
     TAGCTACTTAAGGGCCCGGACTCCTCTAGAAGCTTGATCATTCGA-5'
``` with a basal salts glucose medium containing tetracycline. The cultures were harvested by centrifugation and the resulting biomass was used to perform in vivo (i.e., whole cell) assays or to generate cell-free lysates for in vitro desulfurization assays. SDS-PAGE and Western Blot Analysis Protein separations were done with Novex (San Diego, Calif.) precast 10% polyacylamide gels with Tris-Glycine-sodium dodecyl sulfate (SDS) (Laemmli) running buffer. Western blot analysis was carried out by first transferring the proteins electrophoretically to nitrocellulose membranes as recommended by Biorad (Hercules, Calif.) Blots were treated with antisera raised against the purified IGTS8 Dsz proteins (primary antibody) and then with goat anti-rabbit antisera conjugated to horseradish peroxidase as the second antibody. Finally, the proteins were detected with a horseradish peroxidase catalyzed chemiluminescence reaction.

Example 1
Construction of recombinant plasmids

A number of broad host range expression vectors have been described for use in gram-negative bacteria (Mermod et al., in R. Sokatch and L. N. Ornston, ed., *The Bacteria* vol. 10, p. 325–355, 1986), however, plasmids that contain the $P_G$ promoter, which is regulated by nan R, have proven to be very useful in the overexpression of several genes in Pseudomonas hosts (Frazee et al., *J. Bacteriol.* 175:6194–6202 (1993); Yen, K.,W., *J. Bacteriol.* 173:5328–5335 (1991)). This vector/promoter system was chosen to express the Rhodococcus IGTS8 desulfurization genes (dsz) in gram-negative hosts.

Enzyme kinetic analysis has shown that the rate of the second oxygenation step, which is catalyzed by $DBTO_2$-MO (i.e., DszA), is about ten times faster than the rate of the first oxygenation step which is carried out by DBT-MO (i.e. DszC)(Gray et al., *Nature Biotechnology*, 14:1705–1709 (1996)). In the present studies organization of the dsz genes on the plasmid in the order dszCAB gives improved expression of DszC.

A. pEX1087

The broad-host range plasmid pEX1087, which contains the dsz genes in the order dszCAB, was constructed in several cloning steps.

1. A synthetic duplex DNA oligonucleotide adaptor with the sequence shown below (SEQ ID NOS: 13and 14) was ligated into the EcoRI and HindIII sites of pUC18 and the resulting plasmid was designated pEX82.

2. The plasmid pEX14 was constructed as described in U.S. patent application Ser. No. 08/662,810, incorporated herein by reference. An ApoI/Bsu311 restriction fragment from pEX14 (described in U.S. patent application Ser. No. 08/351,754, incorporated herein by reference) containing a portion of 3' end of dszB and the complete dszC was ligated with pEX82 that had been digested with EcoRI and Bsu361, resulting in pEX83, which is shown in FIG. 7.

3. A portion of the dszB gene was synthesized by PCR with two oligonucleotides, (B1 and B2, shown below) as the primers and denatured pTOXI1, disclosed in U.S. Pat. No. 5,356,801, as the template.

Primer B1:

```
5'ATCGGAATTCTCTAGAAGATCTGATCGTGGAGGATGATTAAATGACAAGCCGCGTCG  (SEQ ID NO.: 15)
  ACCCCGCAAAC3'
```

Primer B2:

```
5'-TAATAAGCTTACTAGTTTAGCGATGTCGGTTCAGAGAATTATTGA-  (SEQ ID NO.: 16)
  GGAACTCCGGAGCGTTGGGTACCGGGCAGTTGCTGTAG3'
```

Figure 8:
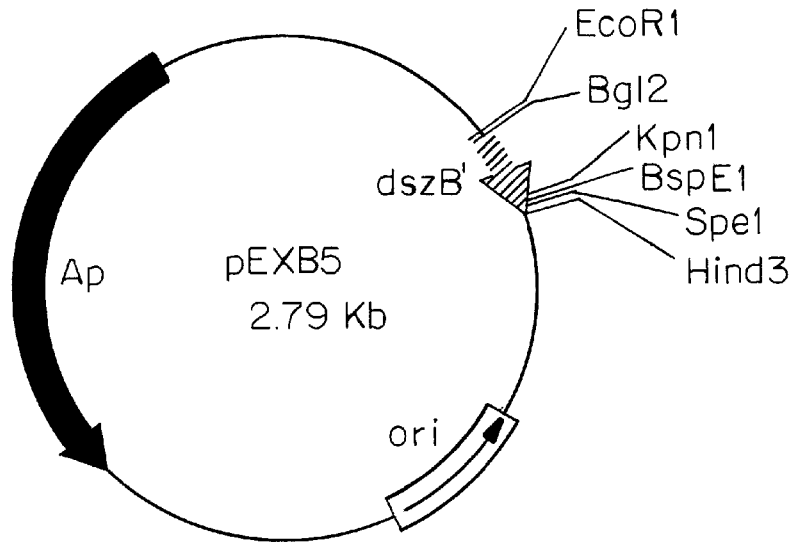
FIG. 8 is a physical map of plasmid pEXB5.

The 0.17 kb product was digested with EcoRI and HindIII and ligated into pUC19 that has been digested with EcoRI and HindIII, resulting in pEXB5, as presented in FIG. 8. The insert was confirmed by DNA sequence analysis.

Figure 9:
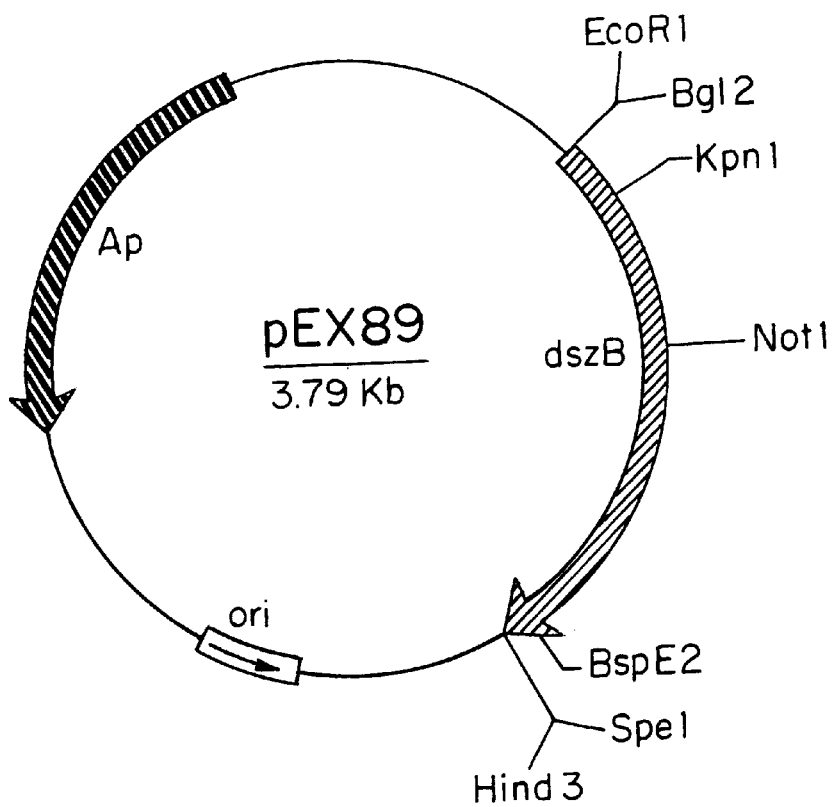
FIG. 9 is a physical map of plasmid pEXB9.

4. The larger KpnI-BspEI fragment from pEXB5 was ligated with a 0.97 kb fragment containing a portion of dszB isolated from pTOXi1 that had been digested with Kpn I and BspEI. The resulting plasmid was designed pEXB9 and is shown in FIG. 9.

Figure 10:
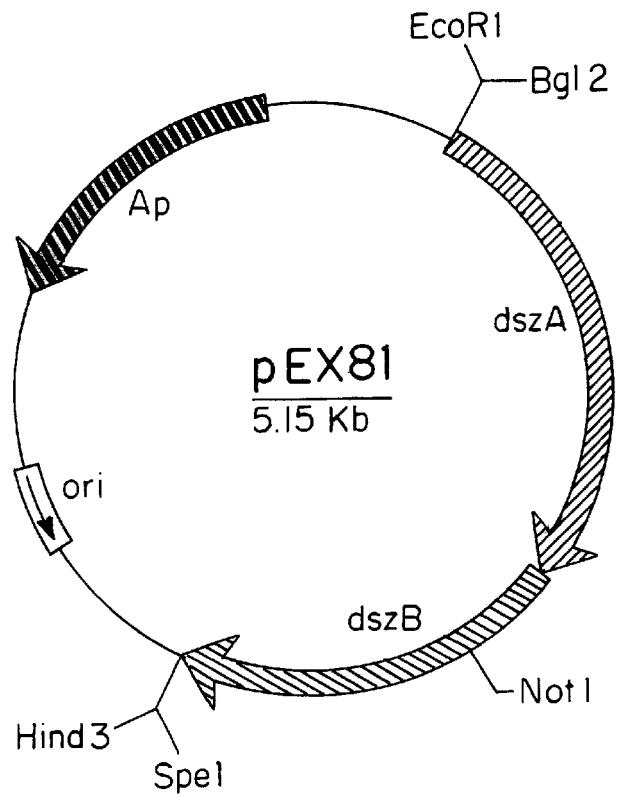
FIG. 10 is a physical map of plasmid pEX81.

5. A Bgl II-Not I fragment containing dszA and 5' end of dszB isolated from pEX14 was ligated with the largest Bgl II-Not I fragment isolated from pEXB9 to form plasmid pEX81, as shown in FIG. 10.

Figure 11:
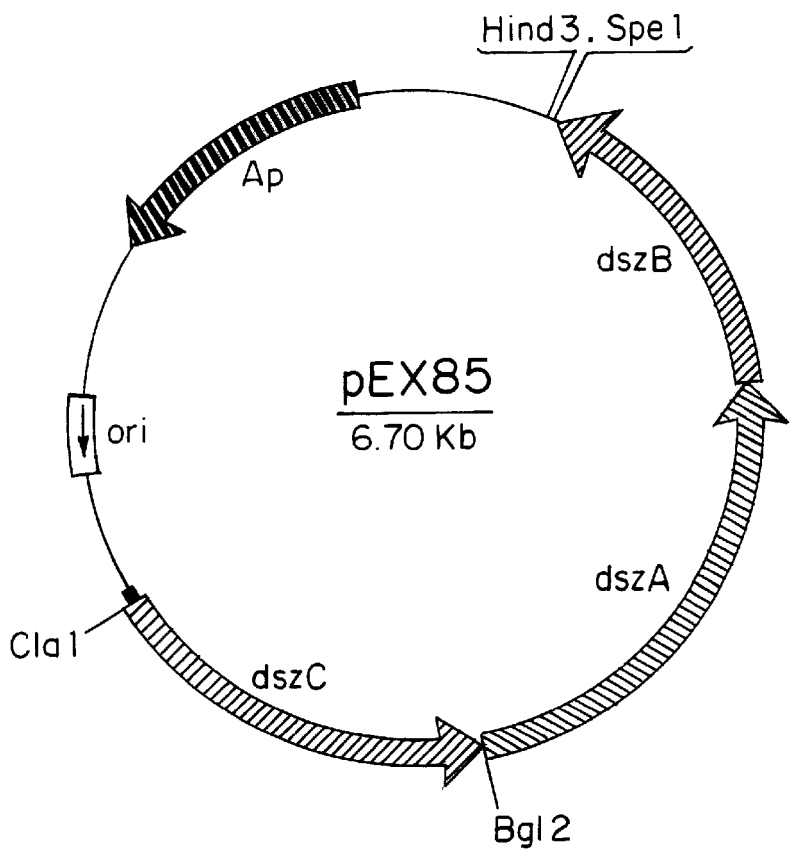
FIG. 11 is a physical map of plasmid pEX85.

6. The 2.2 kb BglII-HindIII fragment containing dszA and dszB from pEX81 was isolated and inserted into the Bgl II and HindIII sites of pEX83, resulting in plasmid pEX85, as shown in FIG. 11.

7. A synthetic duplex DNA oligonucleotide adaptor with the following sequence (SEQ ID NOS: 17 and 18)

```
5'AATTCTAGAGAGGAACTCCATGCCAATCAATTGCAAAGCCCGGGACTAGTA
    GATCTCTCCTTGAGGTACGGTTAGTTAACGTTTCGGGCCCTGATCATTCGA5'
``` was ligated into pUC18 that had been digested with EcoRI and HindIII, resulting in pEX91.

Figure 12:
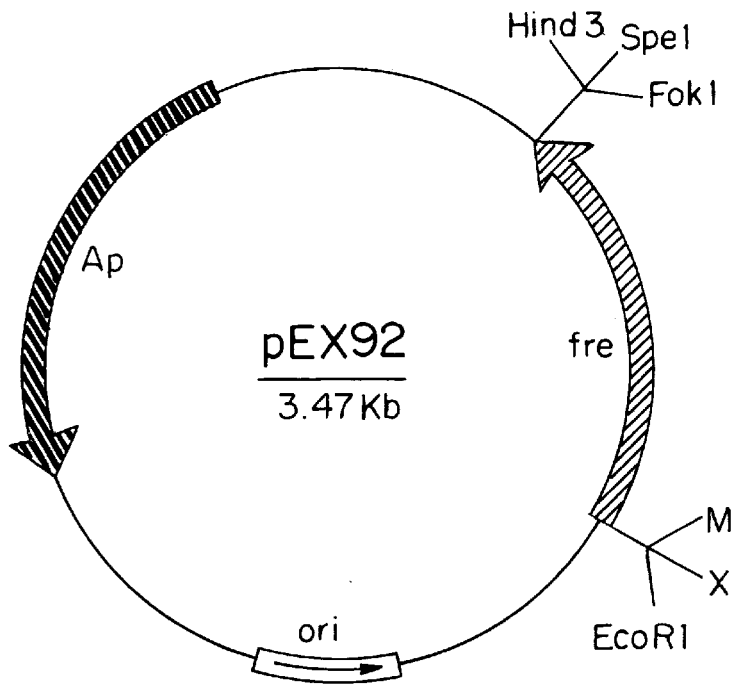
FIG. 12 is a physical map of plasmid pEX92.

8. A 0.7 kb MunI/blunted-Fok1I restriction fragment containing the 31'-end of fre, from plasmid pfFRI (Zenno, S. & Saigo, K., *J. Bacteriol.* 176:3544–3551, (1994)) was ligated with MunI-SmaI-digested pEX91. The resulting plasmid was designated pEX92 (FIG. 12).

9. The pacHG genes were removed from pRWF113 (Frazee, R.W.J. et al., *J. Bacteriol.* 175:6194–6202 (1993)), a derivative plasmid from pKMY319 (Yen, K.-W., *J. Bacteriol.* 173:5328–5335, (1991)), be digesting with ClaI and XhoI. This fragment was replaced by ligation with a synthetic duplex DNA adaptor with structure shown below (SEQ ID NOS: 19 and 20).

```
5'-CGATCTAGAGGAGGCTTCATATGTTTAAACTAGTC
    TAGATCTCCTCCGAAGTATACAAATTTGATCAGAGCT-5'
```

Figure 13:
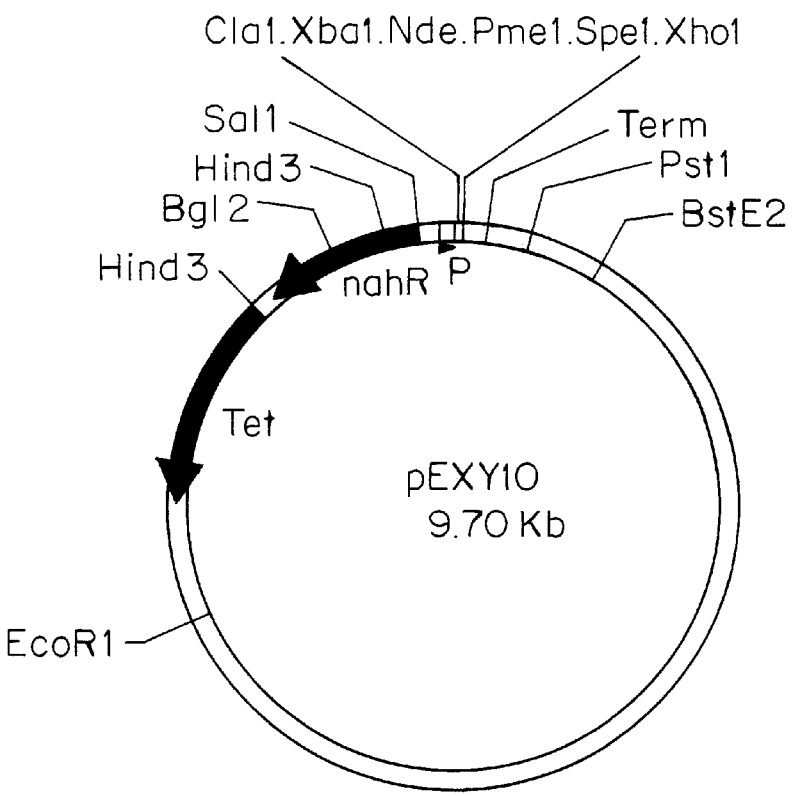
FIG. 13 is a physical map of plasmid pEXY10.

The resulting expresion vector, pEXY10, is shown in FIG. 13.

Figure 14:
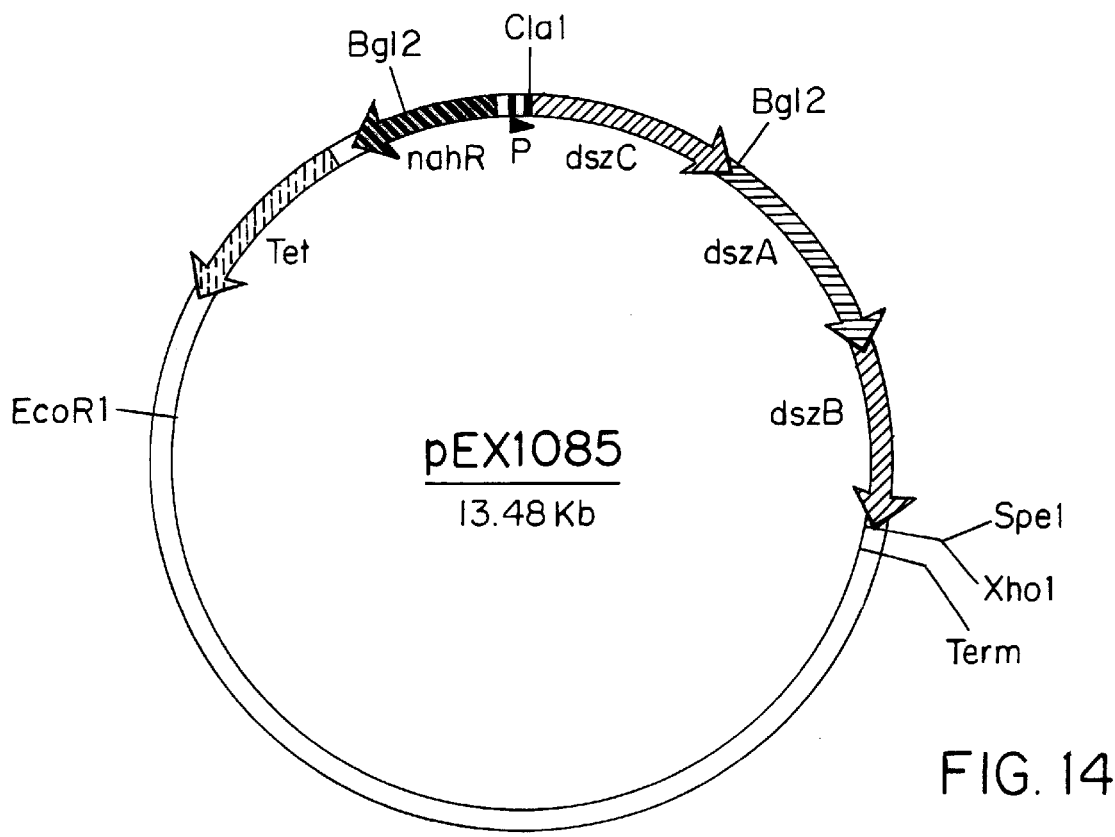
FIG. 14 is a physical map of plasmid pEX1085.

10. The ClaI-SpeI fragment containing the dszCBA genes from pEX85 was subcloned into the ClaISpeI sites of pEXY10. The resulting plasmid, pEX1085, is shown in FIG. 14.

Figure 15:
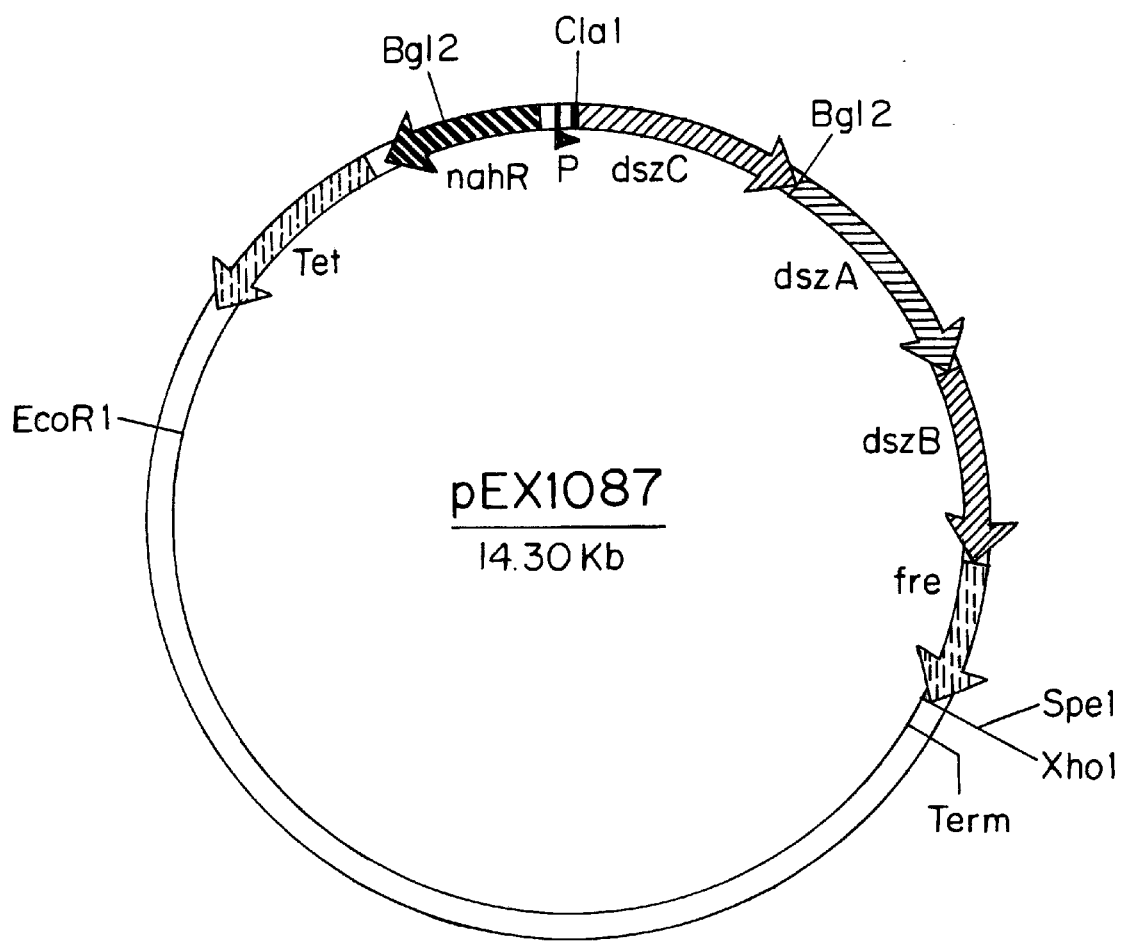
FIG. 15 is a physical map of plasmid pEX1087.

11. A SpeI-XbaI fragment containing the fre gene was isolated from pEX92 and ligated into the SpeI site of pEX1085. The resulting plasmid, designated pEX1087, is shown in FIG. 15.

B. pDA121

Figure 16:
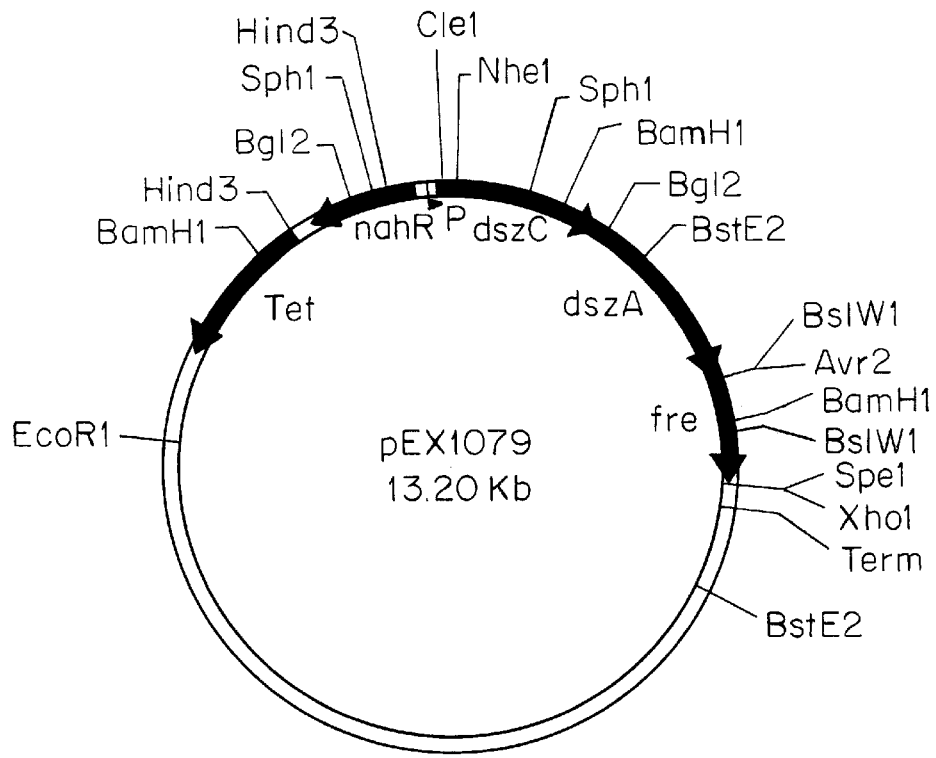
FIG. 16 is a physical map of plasmid pEX1079.
Figure 17:
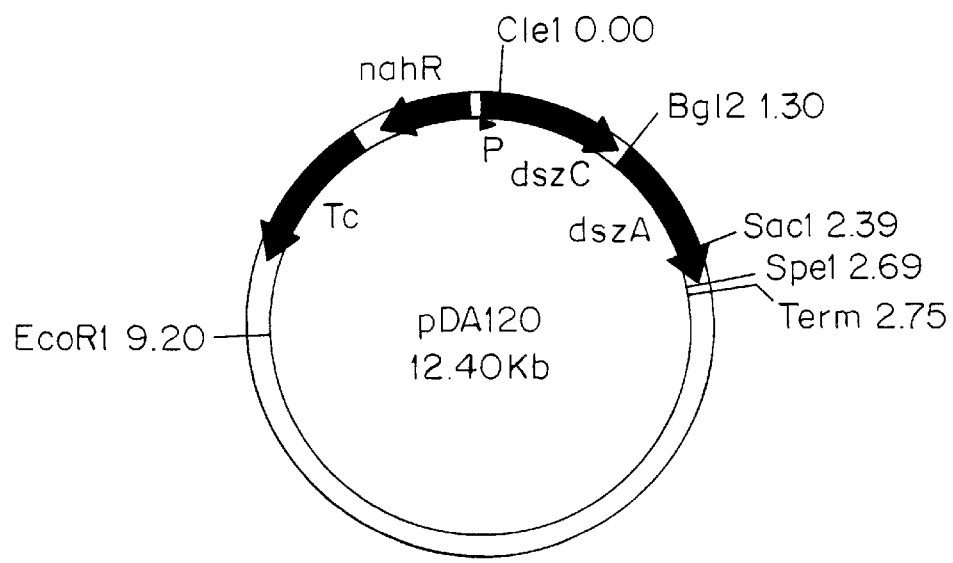
FIG. 17 is a physical map of plasmid pDA120.

Plasmid pDA121 (dszCA frda), which is based on plasmid pEX1079 (dszCAfre; FIG. 16), was constructed in two cloning steps. The first step involved replacing the Vibrio NADH-FMN oxidoreductase gene (fre) in pEX1079 with the Rhodococcus IGTS8 flavin reductase gene (freA). A SacI-SpeI fragment containing the 3' portion of the (dszCA fre gene was removed from plasmid pEX1079 (dszCA fre). This fragment was replaced with a 200 bp SacI-SpeI-fragment containing the 3' portion of the dszA gene from pEBC443. Plasmid pEBC443 contains the dszA gene cloned into the tac promoter expression vector pT3XI2). The ligation of the 200 bp SacI-SpeI fragment from pEBC443 into pEX1079, thereby recreated the dszA gene. The resulting plasmid designated, pDA120 (FIG. 17), contains intact dszC and A genes and a unique SpeI site immediately downstream of dszA.

Figure 20:
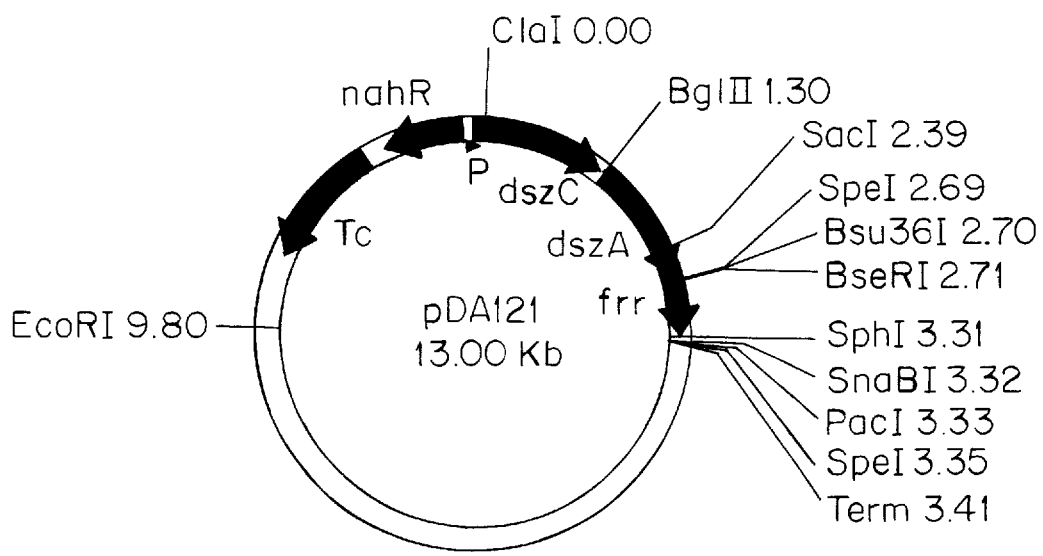
FIG. 20 is a physical map of plasmid pDA121.

In the second step, the Rhodococcus IGTS8 frdA gene was inserted downstream of the dszA gene in pDA120. Before this was done, however, the native frdA gene was first modified to improve translation in a recombinant host. Specifically, the uncommon TTG initiation codon of frdA gene was replaced with an ATG start codon and the native ribosome binding site (RBS) was replaced with the RBS of thcE gene, as described in U.S. patent application No. 08/583,118, the contents of which are incorporated herein by reference. A DNA linker. (FIG. 18 SEQ ID NOS: 21 and 23) containing these modifications and the coding region for the first 7 amino acids residues (SEQ ID NOS: 22) of the frda gene including the BsmI site, was cloned into the BamHI and HindIII sites of pUC19. Following DNA sequence verification of the linker, a BsmI-SnaB1 fragment of the frda which lacked a RBS, initiation codon and coding region for the first 7 amino acids was cloned into the BsmI-SnaB1 sites of the pUC19-linker clone. The resulting plasmid was designated pECB615. The frdA gene was removed from pEBC615 as a SpeI fragment and inserted into the SpeI site of pDA120. Following transformation and characterization of the resulting transformants, one construct, designated pDA121 (dszCAfrdA: FIG. 20), which contains frda in the correct transcriptional orientation with respect to the promoter $P_G$ was chosen for further analysis.

Example 2

Expression of the dsz genes in *P. fluorescens* ATCC 13525

Plasmid pEX1087 was introduced into *P. fluorescens* ATCC 13525. A single tetracycline-resistant transconjugant from each mating was selected for further analysis.

The tetracycline-resistant *P. fluorescens* ATCC 13525/pEX1087 transconjugant was able to produce a zone of clearing on a BSM Glucose $DBTO_2$ plate indicating the presence of the dsz genes. The production of clearing zones was salicylate independent. The parent strain without pEX1087 was not capable of producing clearing zones. Induction of a *P. fluorescens* ATCC 13525/pEX1087 culture with salicylate resulted in significant whole cell desulfurization activity (14.9 $\mu$moles HPBS/min/gdcw, (gdcw=gram dry cell weight) as determined in single phase assays. Significantly more HPBS than 2-HBP was produced in this assay and is consistent with previous data that the last step in the pathway (catalyzed by HPBS desulfinase) is rate limiting (Gray et al., *Nature Biotechnology* 14 :1707–1709 (1996)). In the absence of inducer very little desulfurization activity (0.7 $\mu$moles HPBS/min/gdcw) was detected indicating that the transcription of the dsz genes in this host was tightly regulated.

Figure 19:
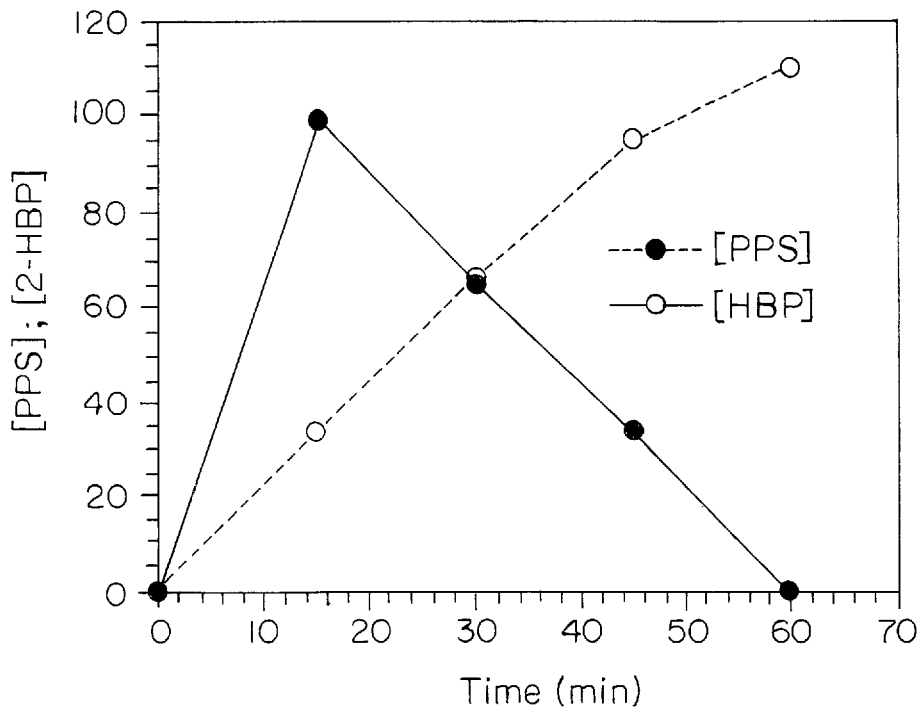
FIG. 19 presents the results of an in vitro desulfurization assay using a cell-free lysate prepared from a salicylate induced culture of P. fluorescens ATCC 13525/pEX1087.

Conversion of DBT to HPBS and 2-HBP was also demonstrated in cell free extracts prepared from a salicylate induced culture of *P. fluorescens*/pEX1087, as presented in FIG. 19. The level of HPBS increased over the first 15 min. but then decreased to near baseline levels by 60 min., whereas the levels of 2-HBP steadily increased over the length of the assay. This product accumulation profile is consistent with that previously seen with Rhodocossus IGTS8 cell free extracts (Gray et al., *Nature Biotechnology* 14:1707–1709 (1996). Western blot analysis of this cell-free lysate revealed the presence of all three Dsz proteins.

Example 3

Expression of the dsz genes in *P. fluorescens* NCIB 11764/pDA121

Plasmid pDA121 was introduced into *P. fluorescens* NCIB 11764. A single tetracycline-resistant transconjugant from each mating was selected for further analysis.

The tetracycline-resistant *P. fluorescens* NCIB 11764/pDA121 transconjugant was also able to produce clearing zones on a BSM Glucose $DBTO_2$ plate indicating the presense of the dsz genes. The production of clearing zones was salicylate independent. Cells obtained from several *P. fluorescens* NCIB 11764/pDA121 salicylate-induced cultures produced significant levels of HPBS in single phase, whole cell assays. This corresponded to an in vivo activity of 2.5–6.0 ($\mu$moles/min/gdcw). In the absence of the inducer, however, little or no activity was detected, indicating that the transcription of the dsz genes in this host was tightly regulated. There was also significant levels of HPBS produced in two-phase desulfurization assays. The amount of HPBS produced corresponded to a specific activity of 9.5 $\mu$moles/min/gdcw).

Cell-free lysates prepared from salicylate induced cultures of P. fluorescens NCIB 11764/pDA121 contained significant FMN reductase activity (9700 to 12,500 nmol NADH oxidized/min/mg). This is compared to FMN reductase activities of 600–1000 for P. fluorescens NCIB 11764 harboring pEX1079 (dszCAfre). SDS-PAGE analysis of this lysate also revealed the presense of prominent FrdA, DszC and DszA protein bands. When compared to a known amount of the purified Rhodoccus reductase, it was estimated that FrdA represents a significant portion of the total cytoplasmic protein. This was the first evidence that co-expression of the dsz genes with frda in a non-Rhodococcus host results in measureable in vivo desulfurization activity.

Plasmid pEX1087, pDA121 or its various derivatives (e.g., pEX1079) have been successfully introduced into a variety of Gram-negative species using the general methods outlined above. These include, but are not limited to Burkholderia cepacia, Comomonas testosteroni, P. aeruginosa, P. aureofaciens, P. alcaligenes, P. chlororaphis, P. denitrifcans, P. fluorescens, P. mendocina, P. oleovorans, P. putida, P. stutzeri, and Sphingomonas paucimobilis. The results presented using P. fluorescens as an expression host are provided as an example. Desulfurization activity was demonstrated for all of the listed recombinants.

EQUIVALENTS

Those skilled in the art will know, or be able to ascertain, using no more than routine experimentation, many equivalents to the specific embodiments of the invention described herein. These and all other equivalents are intended to be encompassed by the following claims.

We claim:

1. A recombinant pseudomonad comprising a heterologous nucleic acid molecule which encodes one or more desulfurization enzymes.

2. The recombinant pseudomonad of claim 1, wherein the pseudomonad is selected from the group consisting of *Pseudomonas fluorescens, Burkholderia cepacia, Comomonas testosteroni, Pseudomonas aeruginosa, Pseudomonas aureofaciens, Pseudomonas alcaligenes, Pseudomonas chlororaphis, Pseudomonas denitrifcans, Pseudomonas fluorescens, Pseudomonas mendocina, Pseudomonas oleovorans, Pseudomonas putida, Pseudomonas stutzeri,* and *Sphingomonas paucimobilis.*

3. The recombinant pseudomonad of claim 2 wherein the host organism is *Pseudomonas fluorescens* ATCC 13525 or *Pseudomonas fluorescens* NCIB 11764.

4. The recombinant pseudomonad of claim 1 wherein the heterologous nucleic acid molecule encodes one or more enzymes presented in SEQ ID NO:2, SEQ ID NO:4 and SEQ ID NO:6, or an active homologue or active fragment thereof.

5. The recombinant pseudomonad of claim 4 wherein the heterologous nucleic acid molecule comprises at least one of the nucleotide sequences set forth in SEQ ID NO:1, SEQ ID NO:3 and SEQ ID NO:5.

6. The recombinant pseudomonad of claim 4 wherein the heterologous nucleic acid molecule comprises a nucleotide sequence which is mutated from the nucleotide sequence set forth in SEQ ID NO:1, SEQ ID NO:3, or SEQ ID NO:5 by the replacement of one or more codons with a degenerate codon.

7. The recombinant pseudomonad of claim 1 wherein the heterologous nucleic acid molecule encodes at least one of the enzymes having an amino acid sequence set forth in SEQ ID NO:8, SEQ ID NO:10 or SEQ ID NO:12; or an active fragment thereof.

8. The recombinant pseudomonad of claim 7 wherein the heterologous nucleic acid molecule includes one or more of the nucleotide sequences set forth in SEQ ID NO:7, SEQ ID NO:9, and SEQ ID NO:11.

9. The recombinant pseudomonad of claim 7 wherein the heterologous nucleic acid molecule comprises a nucleotide sequence which is mutated from the nucleotide sequence set forth in SEQ ID NO:1, SEQ ID NO:3, or SEQ ID NO:5 by the replacement of one or more codons with a degenerate codon.

10. The recombinant pseudomonad of claim 1 wherein the heterologous nucleic acid molecule is of Rhodococcus origin.

11. The recombinant pseudomonad of claim 1 wherein the heterologous nucleic acid molecule is of Sphingomonas origin.

12. The recombinant pseudomonad of claim 1 wherein the heterologous nucleic acid molecule encodes a desulfurization enzyme which is a mutation of the enzyme set forth in SEQ ID NO:2, SEQ ID NO:4, or SEQ ID NO:6.

13. The recombinant pseudomonad of claim 12 wherein the heterologous nucleic acid molecule encodes an enzyme having an amino acid sequence which is mutated from the amino acid sequence set forth in SEQ ID NO:2, SEQ ID NO:4 or SEQ ID NO:6 by conservative substitution of one or more amino acid residues.

14. The recombinant pseudomonad of claim 1 wherein the heterologous nucleic acid molecule encodes a desulfurization enzyme which is a mutation of an enzyme set forth in SEQ ID NO:8, SEQ ID NO:10 or SEQ ID NO:12.

15. The recombinant pseudomonad of claim 14 wherein the heterologous nucleic acid molecule encodes an enzyme having an amino acid sequence which is mutated from the amino acid sequence set forth in SEQ ID NO:8, SEQ ID NO:10 or SEQ ID NO:12 by conservative substitution of one or more amino acid residues.

16. The recombinant pseudomonad of claim 1 wherein the heterologous nucleic acid molecule encodes an amino acid sequence comprising the amino acid residues which are conserved in SEQ ID NO:2 and SEQ ID NO:8.

17. The recombinant pseudomonad of claim 1 wherein the heterologous nucleic acid molecule encodes an amino acid sequence which comprises the amino acid residues which are conserved in SEQ ID NO:4 and SEQ ID NO:10.

18. The recombinant pseudomonad of claim 1 wherein the heterologous nucleic acid molecule encodes an amino acid sequence comprising the amino acid residues which are conserved in SEQ ID NO:6 and SEQ ID NO:12.

19. The recombinant pseudomonad of claim 1 wherein the heterologous nucleic acid molecule further encodes a flavoprotein.

20. The recombinant pseudomonad of claim 19 wherein the flavoprotein is a flavin reductase.

21. A method for desulfurizing a carbonaceous material which includes organosulfur compounds, comprising the steps of:

(a) contacting the carbonaceous material with an aqueous phase containing a recombinant pseudomonad biocatalyst comprising at least one heterologous enzyme capable of catalyzing at least one step in the oxidative cleavage of carbon-sulfur bonds, thereby forming a carbonaceous material and aqueous phase mixture;

(b) maintaining the mixture of step (a) under conditions sufficient for biocatalysis, thereby resulting in a carbonaceous material having a reduced organic sulfur content; and (c) separating the carbonaceous material having a reduced organic sulfur content from the resulting aqueous phase.

22. The method of claim 21 wherein the recombinant pseudomonad biocatalyst is a recombinant pseudomonad containing a heterologous nucleic acid molecule which encodes one or more desulfurization enzymes; or an enzyme preparation derived therefrom.

23. The method of claim 22 wherein the recombinant pseudomonad is selected from the group consisting of *Pseudomonas fluorescens, Burkholderia cepacia, Comomonas testosteroni, Pseudomonas aeruginosa, Pseudomonas aureofaciens, Pseudomonas alcaligenes, Pseudomonas chlororaphis, Pseudomonas denitrifcans, Pseudomonas fluorescens, Pseudomonas mendocina, Pseudomonas oleovorans, Pseudomonas putida, Pseudomonas stutzeri,* and *Sphingomonas paucimobilis.*

24. The method of claim 23 wherein the pseudomonad is *Pseudomonas fluorescens* NCIB 11764 or *Pseudomonas fluorescens* ATCC 13525.

25. The method of claim 21 wherein the carbonaceous material is a fossil fuel.

26. The method of claim 25 wherein the fossil fuel is petroleum or a petroleum distillate fraction.

27. The method of claim 22 wherein the heterologous nucleic acid molecule encodes one or more of the enzymes presented in SEQ ID NO:2, SEQ ID NO:4 and SEQ ID NO:6.

28. The method of claim 27 wherein the heterologous nucleic acid molecule includes one or more of the nucleotide sequences set forth in SEQ ID NO:1, SEQ ID NO:3, and SEQ ID NO:5.

29. The method of claim 27 wherein the heterologous nucleic acid molecule comprises a nucleotide sequence which is mutated from the nucleotide sequence set forth in SEQ ID NO:1, SEQ ID NO:3, or the full coding region corresponding to SEQ ID NO:5 by the replacement of one or more codons with a degenerate codon.

30. The method of claim 22 wherein the heterologous nucleic acid molecule encodes one or more of the enzymes set forth in SEQ ID NO:8, SEQ ID NO:10 and SEQ ID NO:12.

31. The method of claim 30 wherein the heterologous nucleic acid molecule comprises at least one of the nucleotide sequences set forth in SEQ ID NO:7, SEQ ID NO:9 and SEQ ID NO:11.

32. The method of claim 30 wherein the heterologous nucleic acid molecule comprises a nucleotide sequence which is mutated from the nucleotide sequence set forth in SEQ ID NO:7, SEQ ID NO:9, or SEQ ID NO:11 by the replacement of one or more codons with a degenerate codon.

33. The method of claim 22 wherein the heterologous nucleic acid molecule encodes an enzyme which is a mutant of the enzyme set forth in SEQ ID NO:2, SEQ ID NO:4 or SEQ ID NO:6.

34. The method of claim 33 wherein the heterologous nucleic acid molecule encodes an enzyme which is mutated from the enzyme set forth in SEQ ID NO:2, SEQ ID NO:4 or SEQ ID NO:6 by conservative substitution of one or more amino acid residues.

35. The method of claim 22 wherein the heterologous nucleic acid molecule encodes an enzyme which is a mutant of the enzyme set forth in SEQ ID NO:8 or SEQ ID NO:10, or the enzyme having the N-terminal sequence set forth in SEQ ID NO:12.

36. The method of claim 35 wherein the heterologous nucleic acid molecule encodes an enzyme which is mutated from the enzyme set forth in SEQ ID NO:8 or SEQ ID NO:10 or an enzyme having an N-terminal sequence set forth in SEQ ID NO:12 by conservative substitution of one or more amino acid residues.

37. The method of claim 22 wherein the heterologous nucleic acid molecule encodes an enzyme having an amino acid sequence comprising the amino acid residues which are conserved in SEQ ID NO:2 and SEQ ID NO:8.

38. The method of claim 22 wherein the heterologous nucleic acid molecule encodes an enzyme having an amino acid sequence comprising the amino acid residues which are conserved in SEQ ID NO:4 and SEQ ID NO:10.

39. The method of claim 22 wherein the heterologous nucleic acid molecule encodes an enzyme having an amino acid sequence comprising the amino acid residues which are conserved in SEQ ID NO:6 and SEQ ID NO:12.

40. The method of claim 22 wherein the heterologous nucleic acid molecule further encodes a flavoprotein.

41. The method of claim 40 wherein the flavoprotein is a flavin reductase.

42. The method of claim 22 wherein the heterologous nucleic acid molecule is of Rhodococcus origin.

43. The method of claim 42 wherein the heterologous nucleic acid molecule is isolated from Rhodococcus sp. strain IGTS8.

44. The method of claim 22 wherein the heterologous nucleic acid molecule is of Sphingomonas origin.

45. The method of claim 44 wherein the heterologous nucleic acid molecule is derived from Sphingomonas sp. strain AD109.

46. A method of oxidizing an organic compound, comprising the steps of:

(a) contacting the organic compound with an aqueous phase containing a recombinant pseudomonad biocatalyst capable of oxidizing organosulfur compounds, thereby forming an organosulfur compound and aqueous phase mixture; and (b) maintaining the mixture under conditions sufficient for oxidation of the organic compound by the biocatalyst, thereby forming an oxidized organosulfur compound.

47. The method of claim 46 wherein the biocatalyst comprises the enzyme set forth in SEQ ID NO:2, an active mutant or active fragment thereof; the enzyme set forth in SEQ ID NO:6, an active mutant or active fragment thereof; or a combination thereof.

48. The method of claim 46 wherein the biocatalyst comprises the enzyme set forth in SEQ ID NO:8, a mutant or active fragment thereof; an enzyme having the N-terminal sequence set forth in SEQ ID NO:12, an active mutant or active fragment thereof; or a combination thereof.

49. The method of claim 46 wherein the organic compound is an organosulfur compound which is a component of a fossil fuel.

50. The method of claim 46 wherein the organosulfur compound is a substituted or unsubstituted dibenzothiophene.

51. The method of claim 46 wherein the organosulfur compound is a substituted or unsubstituted dibenzothiophene-5-5-dioxide.

52. The method of claim 46 wherein the recombinant pseudomonad contains a heterologous nucleic acid molecule which is derived from Sphingomonas sp. strain AD109.

53. The method of claim 46 wherein the recombinant pseudomonad contains a heterologous nucleic acid molecule which is derived from Rhodococcus sp. strain IGTS8.

* * * * *